United States Patent
Yamada et al.

(10) Patent No.: US 7,691,810 B2
(45) Date of Patent: Apr. 6, 2010

(54) METHOD OF PRODUCING RECOMBINANT ANTITHROMBIN III COMPOSITION

(75) Inventors: Tsuyoshi Yamada, Machida (JP); Mitsuo Satoh, Machida (JP); Yutaka Kanda, Machida (JP); Kazuya Yamano, Machida (JP)

(73) Assignee: Kyowa Hakko Kirin Co., Ltd, Tokyo (JP)

( * ) Notice: Subject to any disclaimer, the term of this patent is extended or adjusted under 35 U.S.C. 154(b) by 366 days.

(21) Appl. No.: 10/959,322

(22) Filed: Oct. 7, 2004

(65) Prior Publication Data

US 2006/0024793 A1  Feb. 2, 2006

Related U.S. Application Data

(60) Provisional application No. 60/572,898, filed on May 21, 2004.

(30) Foreign Application Priority Data

Oct. 9, 2003  (JP)  ............................. 2003-350164

(51) Int. Cl.
*A61K 38/36* (2006.01)
*C07K 14/81* (2006.01)
*C07K 14/475* (2006.01)

(52) U.S. Cl. ........................... 514/8; 530/393; 435/358; 435/362

(58) Field of Classification Search ....................... None
See application file for complete search history.

(56) References Cited

U.S. PATENT DOCUMENTS

| | | | |
|---|---|---|---|
| 4,816,567 | A | 3/1989 | Cabilly |
| 5,453,363 | A | 9/1995 | Rudolph |
| 5,728,568 | A | 3/1998 | Sullivan |
| 5,858,983 | A | 1/1999 | Seed et al. |
| 6,054,304 | A | 4/2000 | Taniguchi et al. |
| 6,602,684 | B1 | 8/2003 | Umana et al. |
| 6,946,292 | B2 | 9/2005 | Kanda et al. |
| 2003/0157108 | A1 | 8/2003 | Presta |
| 2003/0170813 | A1 | 9/2003 | Suga et al. |
| 2004/0072290 | A1 | 4/2004 | Umana et al. |
| 2004/0110704 | A1* | 6/2004 | Yamane et al. ............... 514/44 |
| 2005/0262593 | A1 | 11/2005 | Kanda et al. |
| 2005/0272916 | A1 | 12/2005 | Hanai et al. |
| 2005/0276805 | A1 | 12/2005 | Hanai et al. |
| 2005/0287138 | A1 | 12/2005 | Iida et al. |
| 2006/0024800 | A1 | 2/2006 | Hanai et al. |
| 2006/0063254 | A1 | 3/2006 | Kanda et al. |
| 2006/0064781 | A1 | 3/2006 | Kanda et al. |
| 2006/0078990 | A1 | 4/2006 | Kanda et al. |
| 2006/0078991 | A1 | 4/2006 | Kanda et al. |

FOREIGN PATENT DOCUMENTS

| | | | |
|---|---|---|---|
| CA | 2424602 | * | 4/2002 |
| EP | 623352 | | 11/1994 |
| EP | 0816503 A1 | | 1/1998 |
| EP | 882794 | | 9/1998 |
| JP | 2005-058111 A | | 3/2005 |
| WO | WO 91/19501 | | 12/1991 |
| WO | WO 94/16094 | | 7/1994 |
| WO | 96/26268 A1 | | 8/1996 |
| WO | 97/27303 | | 7/1997 |
| WO | 97/30087 | | 8/1997 |
| WO | 97/37683 | | 10/1997 |
| WO | 98/54964 | | 12/1998 |
| WO | 99/54342 | | 10/1999 |
| WO | 99/64618 | | 12/1999 |
| WO | 00/61739 | | 10/2000 |
| WO | 02/02793 | * | 1/2002 |
| WO | 02/31140 | * | 4/2002 |
| WO | WO 03/035835 | | 5/2003 |

OTHER PUBLICATIONS

L. Franzen et al. "Structural Studies on the Carbohydrate Portion of Human Antithrombin III", J. Biol. Chem, 255(11): 5090-5093. (Jun. 1980).*
E. Ersdal-Badju et al. "Elimination of Glycosylation Heterogeneity Affecting Heparin Affinity of Recombinant Human Antithrombin III By Expression of a Beta-like Variant in Baculovirus-Infected Insect Cells", Biocem. J. 310: 323-330. (1995).*
S.T. Olson et al. "Effect of Individula Carbohydrate Chains of Recombinant Antithrombin on Heparin Affinity and on the Generation of Glycoforms Differing in Heparin Affinity", Arch. Biochem. Biophys. 341(2): 212-221 (May 1997).*
L. Garone et al. "Antithrombin-Heparin Affinity Reduced By Fucosylation of Carbohydrate at Asparagine 155", Biochem. 35: 8881-8889. (1996).*
G. Zettlmeissl et al., "Characterization of Recombinant Human Antithrombin III Synthesized in Chinese Hamster Ovary Cells", J. Biol. Chem. 264(35): 21153-21159. (Dec. 1989).*
U.S. Appl. No. 11/279,748, filed Apr. 2006, Kanda et al.
U.S. Appl. No. 09/958,307, filed Oct. 2001, Kanda et al.
Maly et al, Cell, vol. 86, 643-653, Aug. 23, 1996.
Wright et al. Tibtech, 15, 26-32 (1997).
Breton et al, Glycobiology, 8, No. 1, 87-94 (1998).
Asano et al, The EMBO Journal, vol. 16, No. 8, pp. 1850-1857 (1997).
Shitara et al. Journal of Immunological Methods, 167, 271-278 (1994).
Oriol et al. Glycobiology, 9, No. 4, 323-334 (1999).

(Continued)

*Primary Examiner*—Rebecca Prouty
(74) *Attorney, Agent, or Firm*—Sughrue Mion, PLLC

(57) ABSTRACT

The present invention provides a process for producing an antithrombin III composition comprising an antithrombin III molecule having complex type N-glycoside-linked sugar chains, wherein the complex type N-glycoside-linked sugar chains have a structure in which fucose is not bound to N-acetylglucosamine in the reducing end in the sugar chains.

3 Claims, 6 Drawing Sheets

OTHER PUBLICATIONS

Raju, et al. (2000) Glycobiology, 10(5): 477-86.
Stryer (1988) Biochemistry, 3rd Ed., Freeman and Co., New York, NY, pp. 35-37.
Shinkawa, et al. (2003) J. Biol. Chem., 278(5): 3466-73.
Jones, et al. (2001) Pharmacogenomics J., 1(2): 126-34.
Lifely, et al. (1995) Glycobiology, 5(8): 813-22.
U.S. Appl. No. 60/337,642, filed Oct. 2001, Presta.
U.S. Appl. No. 60/347,694, filed Jan. 2002, Presta.
U.S. Appl. No. 60/082,581, filed Apr. 1998, Umana et al.
Wilson et al, "Structural analysis of N-glycans from allergenic grass, ragweed and tree pollens: Core 1, 3-linked fucose and xylose present in all pollens examined", Glycoconjugate Journal 15(11):1055-1070 (1998).
Boyd et al, Molecular Immunology, 1995, vol. 32, No. 17/18, pp. 1311-1318.
Clark, Chem. Immunol. 1997, vol. 65, pp. 88-110.
Ohyama et al, The Journal of Biological Chemistry, 1998, vol. 273, No. 23, pp. 14582-14587.
Sullivan et al, The Journal of Biological Chemistry, 1998, vol. 273, No. 14, pp. 8193-8202.
Ripka et al, Archives of Biochemistry and Biophysics, 1986, vol. 249, No. 2, pp. 533-545.
Ripka et al, Somatic Cell and Molecular Genetics, 1986, vol. 12, No. 1 pp. 51-62.
Shields et al, The Journal of Biological Chemistry, 2002, vol. 277, No. 30, pp. 26733-26740.
Jefferies et al (BioChem J. 268 :529-537 (1990).
Potelligent™ Technology, BioWa, Inc, internet address: biowa.com/news/pdf/Bio2003%20&%20Anti-Cancer%20BioWa%20Non%20Confidential.pdf#search=%22 Potelligent%20Technology%20BioWa%2C%20Inc.%20pdf%22, Jul. 21, 2004.
Yamane-Ohnuki et al, Biotechnology & Bioengineering, vol. 87, No. 5, Sep. 5, 2004.
Rituxan product insert, 2 pages, © 2004 IDEC Pharmaceuticals Corporation and Genentech Inc.
Nose, J Immunology (1990) vol. 145, No. 3, 910-914.
Kiyoshi Furukawa, "Study on the Functions of Glycoprotein Sugar Chains in Mammalian Development: Functions and Expression of the β1,4-Linked Galactose Residues", Protein Nucleic Acid Enzyme, 1998, 43(16): 2309-2317.
Supplemental European Search Report dated Nov. 27, 2008, in EP 04773775.
Tim Edmunds et al., "Transgenically Produced Human Antithrombin: Structural and Functional Comparison to Human Plasma-Derived Antithrombin", Blood, 1998, 91(12): 4561-4571.
Masaaki Hirose et al., "Recombinant human antithrombin expressed in Chinese hamster ovary cells shows in vivo efficacy on rat DIC model similarly to plasma-derived antithrombin regardless of different N-glycosylation", Thrombosis Research, 2007, 119: 631-641.
Takeshi Omasa et al., "Decrease in Antithrombin III Fucosylation by Expressing GDP-fucose Transporter siRNA in Chinese Hamster Ovary Cells", Journal of Bioscience and Bioengineering, 2008, 106(2): 168-173.
Yutaka Kanda et al., "Establishment of a GDP-mannose 4,6-dehydratase (GMD) knockout host cell line: A new strategy for generating completely non-fucosylated recombinant therapeutics", Journal of Biotechnology, 2007, 130: 300-310.
Bing MA et al., "Fucosylation in prokaryotes and eukaryotes", Glycobiology, 2006, 16(12): 158R-184R.
Japanese Office Action issued Oct. 28, 2008 in JP 2005-514674.
Abstracts of Speech at Convention of the Society for Biotechnology, Japan, vol. 2002, 2002, p. 205.

* cited by examiner

SEQUENCE LISTING

<160> NUMBER OF SEQ ID NOS: 40

<210> SEQ ID NO 1
<211> LENGTH: 1395
<212> TYPE: DNA
<213> ORGANISM: Homo sapiens

<220> FEATURE:
<221> NAME/KEY: CDS
<222> LOCATION: (1)..(1395)

<400> SEQUENCE: 1

```
atg tat tcc aat gtg ata gga act gta acc tct gga aaa agg aag gtt      48
Met Tyr Ser Asn Val Ile Gly Thr Val Thr Ser Gly Lys Arg Lys Val
 1               5                  10                  15 tat ctt ttg tcc ttg ctg ctc att ggc ttc tgg gac tgc gtg acc tgt      96
Tyr Leu Leu Ser Leu Leu Leu Ile Gly Phe Trp Asp Cys Val Thr Cys
             20                  25                  30 cac ggg agc cct gtg gac atc tgc aca gcc aag ccg cgg gac att ccc     144
His Gly Ser Pro Val Asp Ile Cys Thr Ala Lys Pro Arg Asp Ile Pro
         35                  40                  45 atg aat ccc atg tgc att tac cgc tcc ccg gag aag aag gca act gag     192
Met Asn Pro Met Cys Ile Tyr Arg Ser Pro Glu Lys Lys Ala Thr Glu
     50                  55                  60 gat gag ggc tca gaa cag aag atc ccg gag gcc acc aac cgg cgt gtc     240
Asp Glu Gly Ser Glu Gln Lys Ile Pro Glu Ala Thr Asn Arg Arg Val
 65                  70                  75                  80 tgg gaa ctg tcc aag gcc aat tcc cgc ttt gct acc act ttc tat cag     288
Trp Glu Leu Ser Lys Ala Asn Ser Arg Phe Ala Thr Thr Phe Tyr Gln
                 85                  90                  95 cac ctg gca gat tcc aag aat gac aat gat aac att ttc ctg tca ccc     336
His Leu Ala Asp Ser Lys Asn Asp Asn Asp Asn Ile Phe Leu Ser Pro
            100                 105                 110 ctg agt atc tcc acg gct ttt gct atg acc aag ctg ggt gcc tgt aat     384
Leu Ser Ile Ser Thr Ala Phe Ala Met Thr Lys Leu Gly Ala Cys Asn
        115                 120                 125 gac acc ctc cag caa ctg atg gag gta ttt aag ttt gac acc ata tct     432
Asp Thr Leu Gln Gln Leu Met Glu Val Phe Lys Phe Asp Thr Ile Ser
    130                 135                 140 gag aaa aca tct gat cag atc cac ttc ttc ttt gcc aaa ctg aac tgc     480
Glu Lys Thr Ser Asp Gln Ile His Phe Phe Phe Ala Lys Leu Asn Cys
145                 150                 155                 160 cga ctc tat cga aaa gcc aac aaa tcc tcc aag tta gta tca gcc aat     528
Arg Leu Tyr Arg Lys Ala Asn Lys Ser Ser Lys Leu Val Ser Ala Asn
                165                 170                 175 cgc ctt ttt gga gac aaa tcc ctt acc ttc aat gag acc tac cag gac     576
Arg Leu Phe Gly Asp Lys Ser Leu Thr Phe Asn Glu Thr Tyr Gln Asp
            180                 185                 190 atc agt gag ttg gta tat gga gcc aag ctc cag ccc ctg gac ttc aag     624
Ile Ser Glu Leu Val Tyr Gly Ala Lys Leu Gln Pro Leu Asp Phe Lys
        195                 200                 205 gaa aat gca gag caa tcc aga gcg gcc atc aac aaa tgg gtg tcc aat     672
Glu Asn Ala Glu Gln Ser Arg Ala Ala Ile Asn Lys Trp Val Ser Asn
    210                 215                 220 aag acc gaa ggc cga atc acc gat gtc att ccc tcg gaa gcc atc aat     720
Lys Thr Glu Gly Arg Ile Thr Asp Val Ile Pro Ser Glu Ala Ile Asn
225                 230                 235                 240 gag ctc act gtt ctg gtg ctg gtt aac acc att tac ttc aag ggc ctg     768
Glu Leu Thr Val Leu Val Leu Val Asn Thr Ile Tyr Phe Lys Gly Leu
                245                 250                 255 tgg aag tca aag ttc agc cct gag aac aca agg aag gaa ctg ttc tac     816
Trp Lys Ser Lys Phe Ser Pro Glu Asn Thr Arg Lys Glu Leu Phe Tyr
            260                 265                 270 aag gct gat gga gag tcg tgt tca gca tct atg atg tac cag gaa ggc     864
Lys Ala Asp Gly Glu Ser Cys Ser Ala Ser Met Met Tyr Gln Glu Gly
        275                 280                 285 aag ttc cgt tat cgg cgc gtg gct gaa ggc acc cag gtg ctt gag ttg     912
```

```
Lys Phe Arg Tyr Arg Arg Val Ala Glu Gly Thr Gln Val Leu Glu Leu
        290                 295                 300 ccc ttc aaa ggt gat gac atc acc atg gtc ctc atc ttg ccc aag cct      960
Pro Phe Lys Gly Asp Asp Ile Thr Met Val Leu Ile Leu Pro Lys Pro
305                 310                 315                 320 gag aag agc ctg gcc aag gtg gag aag gaa ctc acc cca gag gtg ctg     1008
Glu Lys Ser Leu Ala Lys Val Glu Lys Glu Leu Thr Pro Glu Val Leu
                325                 330                 335 cag gag tgg ctg gat gaa ttg gag gag atg atg ctg gtg gtt cac atg     1056
Gln Glu Trp Leu Asp Glu Leu Glu Glu Met Met Leu Val Val His Met
            340                 345                 350 ccc cgc ttc cgc att gag gac ggc ttc agt ttg aag gag cag ctg caa     1104
Pro Arg Phe Arg Ile Glu Asp Gly Phe Ser Leu Lys Glu Gln Leu Gln
        355                 360                 365 gac atg ggc ctt gtc gat ctg ttc agc cct gaa aag tcc aaa ctc cca     1152
Asp Met Gly Leu Val Asp Leu Phe Ser Pro Glu Lys Ser Lys Leu Pro
370                 375                 380 ggt att gtt gca gaa ggc cga gat gac ctc tat gtc tca gat gca ttc     1200
Gly Ile Val Ala Glu Gly Arg Asp Asp Leu Tyr Val Ser Asp Ala Phe
385                 390                 395                 400 cat aag gca ttt ctt gag gta aat gaa gaa ggc agt gaa gca gct gca     1248
His Lys Ala Phe Leu Glu Val Asn Glu Glu Gly Ser Glu Ala Ala Ala
                405                 410                 415 agt acc gct gtt gtg att gct ggc cgt tcg cta aac ccc aac agg gtg     1296
Ser Thr Ala Val Val Ile Ala Gly Arg Ser Leu Asn Pro Asn Arg Val
            420                 425                 430 act ttc aag gcc aac agg ccc ttc ctg gtt ttt ata aga gaa gtt cct     1344
Thr Phe Lys Ala Asn Arg Pro Phe Leu Val Phe Ile Arg Glu Val Pro
        435                 440                 445 ctg aac act att atc ttc atg ggc aga gta gcc aac cct tgt gtt aag     1392
Leu Asn Thr Ile Ile Phe Met Gly Arg Val Ala Asn Pro Cys Val Lys
450                 455                 460 taa                                                                 1395

<210> SEQ ID NO 2
<211> LENGTH: 1398
<212> TYPE: DNA
<213> ORGANISM: Mus musculus
<220> FEATURE:
<221> NAME/KEY: CDS
<222> LOCATION: (1)..(1398)

<400> SEQUENCE: 2 atg tat tcc cct ggg gca gga agt ggg gct gct ggt gag agg aag ctt      48
Met Tyr Ser Pro Gly Ala Gly Ser Gly Ala Ala Gly Glu Arg Lys Leu
1               5                   10                  15 tgt ctc ctc tct ctg ctc ctc atc ggt gcc ttg ggc tgt gct atc tgt      96
Cys Leu Leu Ser Leu Leu Leu Ile Gly Ala Leu Gly Cys Ala Ile Cys
            20                  25                  30 cac gga aac cct gtg gac gac atc Tgc ata gcg aag ccc cga gac atc     144
His Gly Asn Pro Val Asp Asp Ile Cys Ile Ala Lys Pro Arg Asp Ile
        35                  40                  45 ccc gtg aat ccc ttg tgc att tac Cgc tcc cct ggg aag aag gcc acc     192
Pro Val Asn Pro Leu Cys Ile Tyr Arg Ser Pro Gly Lys Lys Ala Thr
50                  55                  60 gag gag gat ggc tca gag cag aag Gtt cca gaa gcc acc aac cgg cgg     240
Glu Glu Asp Gly Ser Glu Gln Lys Val Pro Glu Ala Thr Asn Arg Arg
65                  70                  75                  80 gtc tgg gaa ctg tcc aag gcc aat tcg cga ttt gcc act aac ttc tac     288
Val Trp Glu Leu Ser Lys Ala Asn Ser Arg Phe Ala Thr Asn Phe Tyr
                85                  90                  95
```

```
cag cac ctg gca gac tcc aag aat gac aac gac aac att ttc ctg tca        336
Gln His Leu Ala Asp Ser Lys Asn Asp Asn Asp Asn Ile Phe Leu Ser
        100                 105                 110 ccc ttg agc atc tcc act gct ttt gct atg acc aag ctg ggt gcc tgt        384
Pro Leu Ser Ile Ser Thr Ala Phe Ala Met Thr Lys Leu Gly Ala Cys
        115                 120                 125 aac gac act ctc aag cag ctg atg gag gtt ttt aaa ttt gat acc atc        432
Asn Asp Thr Leu Lys Gln Leu Met Glu Val Phe Lys Phe Asp Thr Ile
    130                 135                 140 tcc gag aag aca tcc gac cag atc cac ttc ttc ttt gcc aaa ctg aac        480
Ser Glu Lys Thr Ser Asp Gln Ile His Phe Phe Phe Ala Lys Leu Asn
145                 150                 155                 160 tgc cga ctc tat cga aaa gcc aac aag tcc tct gac ttg gta tca gcc        528
Cys Arg Leu Tyr Arg Lys Ala Asn Lys Ser Ser Asp Leu Val Ser Ala
                165                 170                 175 aac cgc ctt ttt gga gac aaa tcc ctc acc ttc aac gag agc tat caa        576
Asn Arg Leu Phe Gly Asp Lys Ser Leu Thr Phe Asn Glu Ser Tyr Gln
            180                 185                 190 gat gtt agt gag gtt gtc tat gga gcc aag ctc cag ccc ctg gac ttc        624
Asp Val Ser Glu Val Val Tyr Gly Ala Lys Leu Gln Pro Leu Asp Phe
        195                 200                 205 aag gag aat ccg gag caa tcc aga gtg acc atc aac aac tgg gta gct        672
Lys Glu Asn Pro Glu Gln Ser Arg Val Thr Ile Asn Asn Trp Val Ala
    210                 215                 220 aat aag act gaa ggc cgc atc aaa gat gtc atc cca cag ggc gcc att        720
Asn Lys Thr Glu Gly Arg Ile Lys Asp Val Ile Pro Gln Gly Ala Ile
225                 230                 235                 240 aac gag ctc act gcc ctg gtt ctg gtt aac acc att tac ttc aag ggc        768
Asn Glu Leu Thr Ala Leu Val Leu Val Asn Thr Ile Tyr Phe Lys Gly
                245                 250                 255 ctg tgg aag tca aag ttc agc cct gag aac aca agg aag gaa ccg ttc        816
Leu Trp Lys Ser Lys Phe Ser Pro Glu Asn Thr Arg Lys Glu Pro Phe
            260                 265                 270 tat aag gtc gat ggg cag tca tgc cca gtg cct atg atg tac cag gaa        864
Tyr Lys Val Asp Gly Gln Ser Cys Pro Val Pro Met Met Tyr Gln Glu
        275                 280                 285 ggc aaa ttc aaa tac cgg cgc gtg gca gag ggc acc cag gtg cta gag        912
Gly Lys Phe Lys Tyr Arg Arg Val Ala Glu Gly Thr Gln Val Leu Glu
    290                 295                 300 ctg ccc ttc aag ggg gat gac atc acc atg gtg ctc atc ctg ccc aag        960
Leu Pro Phe Lys Gly Asp Asp Ile Thr Met Val Leu Ile Leu Pro Lys
305                 310                 315                 320 cct gag aag agc ctg gcc aag gtg gag cag gag ctc acc cca gag ctg       1008
Pro Glu Lys Ser Leu Ala Lys Val Glu Gln Glu Leu Thr Pro Glu Leu
                325                 330                 335 ctg cag gag tgg ctg gat gag ctg tca gag act atg ctt gtg gtc cac       1056
Leu Gln Glu Trp Leu Asp Glu Leu Ser Glu Thr Met Leu Val Val His
            340                 345                 350 atg ccc cgc ttc cgc acc gag gat ggc ttc agt ctg aag gag cag ctg       1104
Met Pro Arg Phe Arg Thr Glu Asp Gly Phe Ser Leu Lys Glu Gln Leu
        355                 360                 365 caa gac atg ggc ctc att gat ctc ttc agc cct gaa aag tcc caa ctc       1152
Gln Asp Met Gly Leu Ile Asp Leu Phe Ser Pro Glu Lys Ser Gln Leu
    370                 375                 380 cca ggg atc gtt gct gga ggc agg gac gac ctc tat gtc tcc gac gca       1200
Pro Gly Ile Val Ala Gly Gly Arg Asp Asp Leu Tyr Val Ser Asp Ala
385                 390                 395                 400 ttc cac aaa gca ttt ctt gag gta aat gag gaa ggc agt gaa gca gca       1248
Phe His Lys Ala Phe Leu Glu Val Asn Glu Glu Gly Ser Glu Ala Ala
```

-continued

```
                  405                 410                 415
gcg agt act tct gtc gtg att act ggc cgg tca ctg aac ccc aat agg     1296
Ala Ser Thr Ser Val Val Ile Thr Gly Arg Ser Leu Asn Pro Asn Arg
            420                 425                 430 gtg acc ttc aag gcc aac agg ccc ttc ctg gtt ctt ata agg gaa gtt     1344
Val Thr Phe Lys Ala Asn Arg Pro Phe Leu Val Leu Ile Arg Glu Val
            435                 440                 445 gca ctg aac act att ata ttc atg ggg aga gtg gct aat cct tgt gtg     1392
Ala Leu Asn Thr Ile Ile Phe Met Gly Arg Val Ala Asn Pro Cys Val
        450                 455                 460 aac taa                                                             1398
Asn
465

<210> SEQ ID NO 3
<211> LENGTH: 687
<212> TYPE: DNA
<213> ORGANISM: Sus scrofa
<220> FEATURE:
<221> NAME/KEY: CDS
<222> LOCATION: (65)..(687)

<400> SEQUENCE: 3
ttcagaggga ttgcctcaga ccacactatc tccactcgcc cagacctgtg gaagattagc    60 gacc atg ttt tcc agt ggg ata gga act gta gct gct aga aaa agg        106
     Met Phe Ser Ser Gly Ile Gly Thr Val Ala Ala Arg Lys Arg
     1               5                   10 agg gag tgt ctt ctc tcc ttg ctg att att ggc ctc tgg ggc tgt gtg     154
Arg Glu Cys Leu Leu Ser Leu Leu Ile Ile Gly Leu Trp Gly Cys Val
 15                  20                  25                  30 acc tgt cat tgg agc cct gtg gag gac atc tgc aca gcc aag cct cgg     202
Thr Cys His Trp Ser Pro Val Glu Asp Ile Cys Thr Ala Lys Pro Arg
                 35                  40                  45 gac att ccc gtg aat ccc atg tgc att tac cgt tcc cca gag aag aag     250
Asp Ile Pro Val Asn Pro Met Cys Ile Tyr Arg Ser Pro Glu Lys Lys
             50                  55                  60 gcc act gag ggc gag ggc tca gag cag aag atc cct gag gcc acc aac     298
Ala Thr Glu Gly Glu Gly Ser Glu Gln Lys Ile Pro Glu Ala Thr Asn
         65                  70                  75 cgg cgg gtc tgg gaa ctg tcc aag gcc aat tcc cac ttt gtc acc atc     346
Arg Arg Val Trp Glu Leu Ser Lys Ala Asn Ser His Phe Val Thr Ile
     80                  85                  90 ttc tat cag cac ttg gca gac tcc aag aat gac aat gac aac att ttc     394
Phe Tyr Gln His Leu Ala Asp Ser Lys Asn Asp Asn Asp Asn Ile Phe
 95                 100                 105                 110 ctg tca ccc ctg agt atc tcc aca gct ttt gct atg acc aag ctg ggt     442
Leu Ser Pro Leu Ser Ile Ser Thr Ala Phe Ala Met Thr Lys Leu Gly
                115                 120                 125 gcc tgt gac aac acc ctc aag cag ctg atg gag gtg ttt aag ttt gat     490
Ala Cys Asp Asn Thr Leu Lys Gln Leu Met Glu Val Phe Lys Phe Asp
            130                 135                 140 acc atc tct gag aaa aca tct gat cag gtc cac ttt ttc ttt gcc aaa     538
Thr Ile Ser Glu Lys Thr Ser Asp Gln Val His Phe Phe Phe Ala Lys
        145                 150                 155 ctg aac tgc cga ctc tat cga aaa gcc aac aag tcc tct gag ttg gtg     586
Leu Asn Cys Arg Leu Tyr Arg Lys Ala Asn Lys Ser Ser Glu Leu Val
    160                 165                 170 tca gcc aac cgc ctt ttt gga gac aaa tcc ctt acc ttc aat gag acc     634
Ser Ala Asn Arg Leu Phe Gly Asp Lys Ser Leu Thr Phe Asn Glu Thr
175                 180                 185                 190
```

```
tac cag gaa atc agt gag gtg gta tat gga gcc aag ctc cag ccc ctg    682
Tyr Gln Glu Ile Ser Glu Val Val Tyr Gly Ala Lys Leu Gln Pro Leu
                195             200                 205 gac tt                                                              687
Asp

<210> SEQ ID NO 4
<211> LENGTH: 464
<212> TYPE: PRT
<213> ORGANISM: Homo sapiens

<400> SEQUENCE: 4

Met Tyr Ser Asn Val Ile Gly Thr Val Thr Ser Gly Lys Arg Lys Val
  1               5                  10                  15

Tyr Leu Leu Ser Leu Leu Leu Ile Gly Phe Trp Asp Cys Val Thr Cys
                 20                  25                  30

His Gly Ser Pro Val Asp Ile Cys Thr Ala Lys Pro Arg Asp Ile Pro
             35                  40                  45

Met Asn Pro Met Cys Ile Tyr Arg Ser Pro Glu Lys Lys Ala Thr Glu
         50                  55                  60

Asp Glu Gly Ser Glu Gln Lys Ile Pro Glu Ala Thr Asn Arg Arg Val
 65                  70                  75                  80

Trp Glu Leu Ser Lys Ala Asn Ser Arg Phe Ala Thr Thr Phe Tyr Gln
                 85                  90                  95

His Leu Ala Asp Ser Lys Asn Asp Asn Asp Asn Ile Phe Leu Ser Pro
            100                 105                 110

Leu Ser Ile Ser Thr Ala Phe Ala Met Thr Lys Leu Gly Ala Cys Asn
        115                 120                 125

Asp Thr Leu Gln Gln Leu Met Glu Val Phe Lys Phe Asp Thr Ile Ser
    130                 135                 140

Glu Lys Thr Ser Asp Gln Ile His Phe Phe Ala Lys Leu Asn Cys
145                 150                 155                 160

Arg Leu Tyr Arg Lys Ala Asn Lys Ser Ser Lys Leu Val Ser Ala Asn
                165                 170                 175

Arg Leu Phe Gly Asp Lys Ser Leu Thr Phe Asn Glu Thr Tyr Gln Asp
            180                 185                 190

Ile Ser Glu Leu Val Tyr Gly Ala Lys Leu Gln Pro Leu Asp Phe Lys
        195                 200                 205

Glu Asn Ala Glu Gln Ser Arg Ala Ala Ile Asn Lys Trp Val Ser Asn
    210                 215                 220

Lys Thr Glu Gly Arg Ile Thr Asp Val Ile Pro Ser Glu Ala Ile Asn
225                 230                 235                 240

Glu Leu Thr Val Leu Val Leu Val Asn Thr Ile Tyr Phe Lys Gly Leu
                245                 250                 255

Trp Lys Ser Lys Phe Ser Pro Glu Asn Thr Arg Lys Glu Leu Phe Tyr
            260                 265                 270

Lys Ala Asp Gly Glu Ser Cys Ser Ala Ser Met Met Tyr Gln Glu Gly
        275                 280                 285

Lys Phe Arg Tyr Arg Arg Val Ala Glu Gly Thr Gln Val Leu Glu Leu
    290                 295                 300

Pro Phe Lys Gly Asp Asp Ile Thr Met Val Leu Ile Leu Pro Lys Pro
305                 310                 315                 320

Glu Lys Ser Leu Ala Lys Val Glu Lys Glu Leu Thr Pro Glu Val Leu
                325                 330                 335

Gln Glu Trp Leu Asp Glu Leu Glu Glu Met Met Leu Val Val His Met
```

```
                    340               345                350
Pro Arg Phe Arg Ile Glu Asp Gly Phe Ser Leu Lys Glu Gln Leu Gln
                355                 360                 365
Asp Met Gly Leu Val Asp Leu Phe Ser Pro Glu Lys Ser Lys Leu Pro
            370                 375                 380
Gly Ile Val Ala Glu Gly Arg Asp Asp Leu Tyr Val Ser Asp Ala Phe
385                 390                 395                 400
His Lys Ala Phe Leu Glu Val Asn Glu Glu Gly Ser Glu Ala Ala Ala
                    405                 410                 415
Ser Thr Ala Val Val Ile Ala Gly Arg Ser Leu Asn Pro Asn Arg Val
                420                 425                 430
Thr Phe Lys Ala Asn Arg Pro Phe Leu Val Phe Ile Arg Glu Val Pro
            435                 440                 445
Leu Asn Thr Ile Ile Phe Met Gly Arg Val Ala Asn Pro Cys Val Lys
        450                 455                 460

<210> SEQ ID NO 5
<211> LENGTH: 464
<212> TYPE: PRT
<213> ORGANISM: Mus musculus

<400> SEQUENCE: 5

Met Tyr Ser Pro Gly Ala Gly Ser Gly Ala Ala Gly Glu Arg Lys Leu
 1               5                  10                  15
Cys Leu Leu Ser Leu Leu Leu Ile Gly Ala Leu Gly Cys Ala Ile Cys
                20                  25                  30
His Gly Asn Pro Val Asp Asp Ile Cys Ile Ala Lys Pro Arg Asp Ile
            35                  40                  45
Pro Val Asn Pro Leu Cys Ile Tyr Arg Ser Pro Gly Lys Lys Ala Thr
        50                  55                  60
Glu Glu Asp Gly Ser Glu Gln Lys Val Pro Glu Ala Thr Asn Arg Arg
65                  70                  75                  80
Val Trp Glu Leu Ser Lys Ala Asn Ser Arg Phe Ala Thr Asn Phe Tyr
                85                  90                  95
Gln His Leu Ala Asp Ser Lys Asn Asp Asn Asp Asn Ile Phe Leu Ser
            100                 105                 110
Pro Leu Ser Ile Ser Thr Ala Phe Ala Met Thr Lys Leu Gly Ala Cys
        115                 120                 125
Asn Asp Thr Leu Lys Gln Leu Met Glu Val Phe Lys Phe Asp Thr Ile
    130                 135                 140
Ser Glu Lys Thr Ser Asp Gln Ile His Phe Phe Ala Lys Leu Asn
145                 150                 155                 160
Cys Arg Leu Tyr Arg Lys Ala Asn Lys Ser Ser Asp Leu Val Ser Ala
                165                 170                 175
Asn Arg Leu Phe Gly Asp Lys Ser Leu Thr Phe Asn Glu Ser Tyr Gln
            180                 185                 190
Asp Val Ser Glu Val Val Tyr Gly Ala Lys Leu Gln Pro Leu Asp Phe
        195                 200                 205
Lys Glu Asn Pro Glu Gln Ser Arg Val Thr Ile Asn Asn Trp Val Ala
    210                 215                 220
Asn Lys Thr Glu Gly Arg Ile Lys Asp Val Ile Pro Gln Gly Ala Ile
225                 230                 235                 240
Asn Glu Leu Thr Ala Leu Val Leu Val Asn Thr Ile Tyr Phe Lys Gly
                245                 250                 255
```

```
Leu Trp Lys Ser Lys Phe Ser Pro Glu Asn Thr Arg Lys Glu Pro Phe
            260                 265                 270

Tyr Lys Val Asp Gly Gln Ser Cys Pro Val Pro Met Met Tyr Gln Glu
            275                 280                 285

Gly Lys Phe Lys Tyr Arg Arg Val Ala Glu Gly Thr Gln Val Leu Glu
            290                 295                 300

Leu Pro Phe Lys Gly Asp Asp Ile Thr Met Val Leu Ile Leu Pro Lys
305                 310                 315                 320

Pro Glu Lys Ser Leu Ala Lys Val Glu Gln Glu Leu Thr Pro Glu Leu
                325                 330                 335

Leu Gln Glu Trp Leu Asp Glu Leu Ser Glu Thr Met Leu Val Val His
            340                 345                 350

Met Pro Arg Phe Arg Thr Glu Asp Gly Phe Ser Leu Lys Glu Gln Leu
            355                 360                 365

Gln Asp Met Gly Leu Ile Asp Leu Phe Ser Pro Glu Lys Ser Gln Leu
        370                 375                 380

Pro Gly Ile Val Ala Gly Gly Arg Asp Asp Leu Tyr Val Ser Asp Ala
385                 390                 395                 400

Phe His Lys Ala Phe Leu Glu Val Asn Glu Glu Gly Ser Glu Ala Ala
                405                 410                 415

Ala Ser Thr Ser Val Val Ile Thr Gly Arg Ser Leu Asn Pro Asn Arg
            420                 425                 430

Val Thr Phe Lys Ala Asn Arg Pro Phe Leu Val Leu Ile Arg Glu Val
            435                 440                 445

Ala Leu Asn Thr Ile Ile Phe Met Gly Arg Val Ala Asn Pro Cys Val
450                 455                 460

<210> SEQ ID NO 6
<211> LENGTH: 207
<212> TYPE: PRT
<213> ORGANISM: Sus scrofa

<400> SEQUENCE: 6

Met Phe Ser Ser Gly Ile Gly Thr Val Ala Ala Arg Lys Arg Arg Glu
 1               5                  10                  15

Cys Leu Leu Ser Leu Leu Ile Ile Gly Leu Trp Gly Cys Val Thr Cys
            20                  25                  30

His Trp Ser Pro Val Glu Asp Ile Cys Thr Ala Lys Pro Arg Asp Ile
        35                  40                  45

Pro Val Asn Pro Met Cys Ile Tyr Arg Ser Pro Glu Lys Lys Ala Thr
    50                  55                  60

Glu Gly Glu Gly Ser Gln Lys Ile Pro Glu Ala Thr Asn Arg Arg
65                  70                  75                  80

Val Trp Glu Leu Ser Lys Ala Asn Ser His Phe Val Thr Ile Phe Tyr
                85                  90                  95

Gln His Leu Ala Asp Ser Lys Asn Asp Asn Asp Ile Phe Leu Ser
            100                 105                 110

Pro Leu Ser Ile Ser Thr Ala Phe Ala Met Thr Lys Leu Gly Ala Cys
            115                 120                 125

Asp Asn Thr Leu Lys Gln Leu Met Glu Val Phe Lys Phe Asp Thr Ile
        130                 135                 140

Ser Glu Lys Thr Ser Asp Gln Val His Phe Phe Ala Lys Leu Asn
145                 150                 155                 160

Cys Arg Leu Tyr Arg Lys Ala Asn Lys Ser Ser Glu Leu Val Ser Ala
                165                 170                 175
```

```
Asn Arg Leu Phe Gly Asp Lys Ser Leu Thr Phe Asn Glu Thr Tyr Gln
            180                 185                 190
Glu Ile Ser Glu Val Val Tyr Gly Ala Lys Leu Gln Pro Leu Asp
        195                 200                 205

<210> SEQ ID NO 7
<211> LENGTH: 1504
<212> TYPE: DNA
<213> ORGANISM: Cricetulus griseus
<220> FEATURE:
<221> NAME/KEY: CDS
<222> LOCATION: (1)..(1119)

<400> SEQUENCE: 7 atg gct cac gct ccc gct agc tgc ccg agc tcc agg aac tct ggg gac      48
Met Ala His Ala Pro Ala Ser Cys Pro Ser Ser Arg Asn Ser Gly Asp
  1               5                  10                  15 ggc gat aag ggc aag ccc agg aag gtg gcg ctc atc acg ggc atc acc      96
Gly Asp Lys Gly Lys Pro Arg Lys Val Ala Leu Ile Thr Gly Ile Thr
             20                  25                  30 ggc cag gat ggc tca tac ttg gca gaa ttc ctg ctg gag aaa gga tac     144
Gly Gln Asp Gly Ser Tyr Leu Ala Glu Phe Leu Leu Glu Lys Gly Tyr
         35                  40                  45 gag gtt cat gga att gta cgg cga tcc agt tca ttt aat aca ggt cga     192
Glu Val His Gly Ile Val Arg Arg Ser Ser Ser Phe Asn Thr Gly Arg
     50                  55                  60 att gaa cat tta tat aag aat cca cag gct cat att gaa gga aac atg     240
Ile Glu His Leu Tyr Lys Asn Pro Gln Ala His Ile Glu Gly Asn Met
 65                  70                  75                  80 aag ttg cac tat ggt gac ctc acc gac agc acc tgc cta gta aaa atc     288
Lys Leu His Tyr Gly Asp Leu Thr Asp Ser Thr Cys Leu Val Lys Ile
                 85                  90                  95 atc aat gaa gtc aaa cct aca gag atc tac aat ctt ggt gcc cag agc     336
Ile Asn Glu Val Lys Pro Thr Glu Ile Tyr Asn Leu Gly Ala Gln Ser
            100                 105                 110 cat gtc aag att tcc ttt gac tta gca gag tac act gca gat gtt gat     384
His Val Lys Ile Ser Phe Asp Leu Ala Glu Tyr Thr Ala Asp Val Asp
        115                 120                 125 gga gtt ggc acc ttg cgg ctt ctg gat gca att aag act tgt ggc ctt     432
Gly Val Gly Thr Leu Arg Leu Leu Asp Ala Ile Lys Thr Cys Gly Leu
    130                 135                 140 ata aat tct gtg aag ttc tac cag gcc tca act agt gaa ctg tat gga     480
Ile Asn Ser Val Lys Phe Tyr Gln Ala Ser Thr Ser Glu Leu Tyr Gly
145                 150                 155                 160 aaa gtg caa gaa ata ccc cag aaa gag acc acc cct ttc tat cca agg     528
Lys Val Gln Glu Ile Pro Gln Lys Glu Thr Thr Pro Phe Tyr Pro Arg
                165                 170                 175 tcg ccc tat gga gca gcc aaa ctt tat gcc tat tgg att gta gtg aac     576
Ser Pro Tyr Gly Ala Ala Lys Leu Tyr Ala Tyr Trp Ile Val Val Asn
            180                 185                 190 ttt cga gag gct tat aat ctc ttt gcg gtg aac ggc att ctc ttc aat     624
Phe Arg Glu Ala Tyr Asn Leu Phe Ala Val Asn Gly Ile Leu Phe Asn
        195                 200                 205 cat gag agt cct aga aga gga gct aat ttt gtt act cga aaa att agc     672
His Glu Ser Pro Arg Arg Gly Ala Asn Phe Val Thr Arg Lys Ile Ser
    210                 215                 220 cgg tca gta gct aag att tac ctt gga caa ctg gaa tgt ttc agt ttg     720
Arg Ser Val Ala Lys Ile Tyr Leu Gly Gln Leu Glu Cys Phe Ser Leu
225                 230                 235                 240 gga aat ctg gac gcc aaa cga gac tgg ggc cat gcc aag gac tat gtc     768
```

-continued

```
Gly Asn Leu Asp Ala Lys Arg Asp Trp Gly His Ala Lys Asp Tyr Val
            245                 250                 255 gag gct atg tgg ctg atg tta caa aat gat gaa cca gag gac ttt gtc      816
Glu Ala Met Trp Leu Met Leu Gln Asn Asp Glu Pro Glu Asp Phe Val
            260                 265                 270 ata gct act ggg gaa gtt cat agt gtc cgt gaa ttt gtt gag aaa tca      864
Ile Ala Thr Gly Glu Val His Ser Val Arg Glu Phe Val Glu Lys Ser
        275                 280                 285 ttc atg cac att gga aag acc att gtg tgg gaa gga aag aat gaa aat      912
Phe Met His Ile Gly Lys Thr Ile Val Trp Glu Gly Lys Asn Glu Asn
    290                 295                 300 gaa gtg ggc aga tgt aaa gag acc ggc aaa att cat gtg act gtg gat      960
Glu Val Gly Arg Cys Lys Glu Thr Gly Lys Ile His Val Thr Val Asp
305                 310                 315                 320 ctg aaa tac tac cga cca act gaa gtg gac ttc ctg cag gga gac tgc     1008
Leu Lys Tyr Tyr Arg Pro Thr Glu Val Asp Phe Leu Gln Gly Asp Cys
            325                 330                 335 tcc aag gcg cag cag aaa ctg aac tgg aag ccc cgc gtt gcc ttt gac     1056
Ser Lys Ala Gln Gln Lys Leu Asn Trp Lys Pro Arg Val Ala Phe Asp
        340                 345                 350 gag ctg gtg agg gag atg gtg caa gcc gat gtg gag ctc atg aga acc     1104
Glu Leu Val Arg Glu Met Val Gln Ala Asp Val Glu Leu Met Arg Thr
    355                 360                 365 aac ccc aac gcc tga gcacctctac aaaaaaattc gcgagacatg gactatggtg     1159
Asn Pro Asn Ala
370 cagagccagc caaccagagt ccagccactc ctgagaccat cgaccataaa ccctcgactg    1219 cctgtgtcgt ccccacagct aagagctggg ccacaggttt gtgggcacca ggacggggac    1279 actccagagc taaggccact tcgcttttgt caaaggctcc tctcaatgat tttgggaaat    1339 caagaagttt aaaatcacat actcatttta cttgaaatta tgtcactaga caacttaaat    1399 ttttgagtct tgagattgtt tttctctttt cttattaaat gatctttcta tgacccagca    1459 aaaaaaaaaa aaaaaaggga tataaaaaaa aaaaaaaaaa aaaaa                    1504

<210> SEQ ID NO 8
<211> LENGTH: 372
<212> TYPE: PRT
<213> ORGANISM: Cricetulus griseus

<400> SEQUENCE: 8

Met Ala His Ala Pro Ala Ser Cys Pro Ser Arg Asn Ser Gly Asp
 1               5                  10                  15

Gly Asp Lys Gly Lys Pro Arg Lys Val Ala Leu Ile Thr Gly Ile Thr
            20                  25                  30

Gly Gln Asp Gly Ser Tyr Leu Ala Glu Phe Leu Leu Glu Lys Gly Tyr
        35                  40                  45

Glu Val His Gly Ile Val Arg Arg Ser Ser Phe Asn Thr Gly Arg
     50                  55                  60

Ile Glu His Leu Tyr Lys Asn Pro Gln Ala His Ile Glu Gly Asn Met
 65                  70                  75                  80

Lys Leu His Tyr Gly Asp Leu Thr Asp Ser Thr Cys Leu Val Lys Ile
                85                  90                  95

Ile Asn Glu Val Lys Pro Thr Glu Ile Tyr Asn Leu Gly Ala Gln Ser
               100                 105                 110

His Val Lys Ile Ser Phe Asp Leu Ala Glu Tyr Thr Ala Asp Val Asp
           115                 120                 125
```

```
Gly Val Gly Thr Leu Arg Leu Leu Asp Ala Ile Lys Thr Cys Gly Leu
            130                 135                 140
Ile Asn Ser Val Lys Phe Tyr Gln Ala Ser Thr Glu Leu Tyr Gly
145                 150                 155                 160
Lys Val Gln Glu Ile Pro Gln Lys Glu Thr Thr Pro Phe Tyr Pro Arg
                165                 170                 175
Ser Pro Tyr Gly Ala Ala Lys Leu Tyr Ala Tyr Trp Ile Val Val Asn
            180                 185                 190
Phe Arg Glu Ala Tyr Asn Leu Phe Ala Val Asn Gly Ile Leu Phe Asn
        195                 200                 205
His Glu Ser Pro Arg Arg Gly Ala Asn Phe Val Thr Arg Lys Ile Ser
    210                 215                 220
Arg Ser Val Ala Lys Ile Tyr Leu Gly Gln Leu Glu Cys Phe Ser Leu
225                 230                 235                 240
Gly Asn Leu Asp Ala Lys Arg Asp Trp Gly His Ala Lys Asp Tyr Val
                245                 250                 255
Glu Ala Met Trp Leu Met Leu Gln Asn Asp Glu Pro Glu Asp Phe Val
            260                 265                 270
Ile Ala Thr Gly Glu Val His Ser Val Arg Glu Phe Val Glu Lys Ser
        275                 280                 285
Phe Met His Ile Gly Lys Thr Ile Val Trp Glu Gly Lys Asn Glu Asn
    290                 295                 300
Glu Val Gly Arg Cys Lys Glu Thr Gly Lys Ile His Val Thr Val Asp
305                 310                 315                 320
Leu Lys Tyr Tyr Arg Pro Thr Glu Val Asp Phe Leu Gln Gly Asp Cys
                325                 330                 335
Ser Lys Ala Gln Gln Lys Leu Asn Trp Lys Pro Arg Val Ala Phe Asp
            340                 345                 350
Glu Leu Val Arg Glu Met Val Gln Ala Asp Val Glu Leu Met Arg Thr
        355                 360                 365
Asn Pro Asn Ala
    370

<210> SEQ ID NO 9
<211> LENGTH: 1316
<212> TYPE: DNA
<213> ORGANISM: Cricetulus griseus

<400> SEQUENCE: 9
gccccgcccc ctccacctgg accgagagta gctggagaat tgtgcaccgg aagtagctct      60
tggactggtg gaaccctgcg caggtgcagc aacaatgggt gagccccagg gatccaggag     120
gatcctagtg acagggggct ctggactggt gggcagagct atccagaagg tggtcgcaga     180
tggcgctggc ttacccggag aggaatgggt gtttgtctcc tccaaagatg cagatctgac     240
ggatgcagca caaacccaag ccctgttcca gaaggtacag cccacccatg tcatccatct     300
tgctgcaatg gtaggaggcc ttttccggaa tatcaaatac aacttggatt tctggaggaa     360
gaatgtgcac atcaatgaca acgtcctgca ctcagctttc gaggtgggca ctcgcaaggt     420
ggtctcctgc ctgtccacct gtatcttccc tgacaagacc cctatcccta ttgatgaaac     480
aatgatccac aatggtccac cccacagcag caatttttggg tactcgtatg ccaagaggat     540
gattgacgtg cagaacaggg cctacttcca gcagcatggc tgcaccttca ctgctgtcat     600
ccctaccaat gtctttggac tcatgacaac cttcaacatt gaagatggcc atgtgctgcc     660
tggcctcatc cataaggtgc atctggccaa gagtaatggt tcagccttga ctgtttgggg     720
```

-continued

```
tacagggaaa ccacggaggc agttcatcta ctcactggac ctagcccggc tcttcatctg    780
ggtcctgcgg gagtacaatg aagttgagcc catcatcctc tcagtgggcg aggaagatga    840
agtctccatt aaggaggcag ctgaggctgt agtggaggcc atggacttct gtggggaagt    900 cactttgat tcaacaaagt cagatgggca gtataagaag acagccagca atggcaagct    960
tcgggcctac ttgcctgatt ccgtttcac acccttcaag caggctgtga aggagacctg   1020
tgcctggttc accgacaact atgagcaggc ccggaagtga agcatgggac aagcgggtgc   1080
tcagctggca atgcccagtc agtaggctgc agtctcatca tttgcttgtc aagaactgag   1140
gacagtatcc agcaacctga gccacatgct ggtctctctg ccagggggct tcatgcagcc   1200
atccagtagg gccatgtttt gtccatcctc gggggaaggc cagaccaaca ccttgtttgt   1260
ctgcttctgc cccaacctca gtgcatccat gctggtcctg ctgtcccttg tctaga       1316
```

<210> SEQ ID NO 10
<211> LENGTH: 321
<212> TYPE: PRT
<213> ORGANISM: Cricetulus griseus

<400> SEQUENCE: 10

```
Met Gly Glu Pro Gln Gly Ser Arg Arg Ile Leu Val Thr Gly Gly Ser
  1               5                  10                  15

Gly Leu Val Gly Arg Ala Ile Gln Lys Val Val Ala Asp Gly Ala Gly
             20                  25                  30

Leu Pro Gly Glu Glu Trp Val Phe Val Ser Ser Lys Asp Ala Asp Leu
         35                  40                  45

Thr Asp Ala Ala Gln Thr Gln Ala Leu Phe Gln Lys Val Gln Pro Thr
     50                  55                  60

His Val Ile His Leu Ala Ala Met Val Gly Gly Leu Phe Arg Asn Ile
 65                  70                  75                  80

Lys Tyr Asn Leu Asp Phe Trp Arg Lys Asn Val His Ile Asn Asp Asn
                 85                  90                  95

Val Leu His Ser Ala Phe Glu Val Gly Thr Arg Lys Val Ser Cys
            100                 105                 110

Leu Ser Thr Cys Ile Phe Pro Asp Lys Thr Thr Tyr Pro Ile Asp Glu
        115                 120                 125

Thr Met Ile His Asn Gly Pro Pro His Ser Ser Asn Phe Gly Tyr Ser
    130                 135                 140

Tyr Ala Lys Arg Met Ile Asp Val Gln Asn Arg Ala Tyr Phe Gln Gln
145                 150                 155                 160

His Gly Cys Thr Phe Thr Ala Val Ile Pro Thr Asn Val Phe Gly Pro
                165                 170                 175

His Asp Asn Phe Asn Ile Glu Asp Gly His Val Leu Pro Gly Leu Ile
            180                 185                 190

His Lys Val His Leu Ala Lys Ser Asn Gly Ser Ala Leu Thr Val Trp
        195                 200                 205

Gly Thr Gly Lys Pro Arg Arg Gln Phe Ile Tyr Ser Leu Asp Leu Ala
    210                 215                 220

Arg Leu Phe Ile Trp Val Leu Arg Glu Tyr Asn Glu Val Glu Pro Ile
225                 230                 235                 240

Ile Leu Ser Val Gly Glu Glu Asp Glu Val Ser Ile Lys Glu Ala Ala
                245                 250                 255

Glu Ala Val Val Glu Ala Met Asp Phe Cys Gly Glu Val Thr Phe Asp
            260                 265                 270
```

```
Ser Thr Lys Ser Asp Gly Gln Tyr Lys Lys Thr Ala Ser Asn Gly Lys
        275                 280                 285

Leu Arg Ala Tyr Leu Pro Asp Phe Arg Phe Thr Pro Phe Lys Gln Ala
    290                 295                 300

Val Lys Glu Thr Cys Ala Trp Phe Thr Asp Asn Tyr Glu Gln Ala Arg
305                 310                 315                 320

Lys

<210> SEQ ID NO 11
<211> LENGTH: 2008
<212> TYPE: DNA
<213> ORGANISM: Cricetulus griseus

<400> SEQUENCE: 11
aacagaaact tattttcctg tgtggctaac tagaaccaga gtacaatgtt tccaattctt      60
tgagctccga aagacagaa gggagttgaa actctgaaaa tgcgggcatg gactggttcc     120
tggcgttgga ttatgctcat tcttttgcc tggggacct tattgtttta tataggtggt      180
catttggttc gagataatga ccaccctgac cattctagca gagaactctc caagattctt    240
gcaaagctgg agcgcttaaa acaacaaaat gaagacttga ggagaatggc tgagtctctc    300
cgaataccag aaggccctat tgatcagggg acagctacag aagagtccg tgttttagaa     360 gaacagcttg ttaaggccaa agaacagatt gaaaattaca gaaacaagc taggaatgat    420 ctgggaaagg atcatgaaat cttaaggagg aggattgaaa atggagctaa agagctctgg    480 tttttctac aaagtgaatt gaagaaatta agaaattag aaggaaacga actccaaaga     540
catgcagatg aaattctttt ggatttagga catcatgaaa ggtctatcat acagatcta    600 tactacctca gtcaaacaga tggagcaggt gagtggcggg aaaaagaagc caaagatctg    660
acagagctgg tccagcggag aataacatat ctgcagaatc ccaaggactg cagcaaagcc    720
agaaagctgg tatgtaatat caacaaaggc tgtggctatg gatgtcaact ccatcatgtg    780
gtttactgct tcatgattgc ttatggcacc cagcgaacac tcatcttgga atctcagaat    840
tggcgctatg ctactggagg atgggagact gtgtttagac ctgtaagtga gacatgcaca    900
gacaggtctg gcctctccac tggacactgg tcaggtgaag tgaaggacaa aaatgttcaa    960
gtggtcgagc tccccattgt agacagcctc catcctcgtc ctccttactt acccttggct   1020
gtaccagaag accttgcaga tcgactcctg agagtccatg gtgatcctgc agtgtggtgg   1080
gtatcccagt ttgtcaaata cttgatccgt ccacaaccct ggctggaaag ggaaatagaa   1140
gaaaccacca gaagcttggg cttcaaacat ccagttattg gagtccatgt cagacgcact   1200
gacaaagtgg gaacagaagc agccttccat cccattgagg aatacatggt acacgttgaa   1260 gaacatttc agcttctcga acgcagaatg aaagtggata aaaaagagt gtatctggcc    1320 actgatgacc cttcttttgtt aaaggaggca agacaaagt actccaatta tgaatttat    1380 agtgataact ctatttcttg gtcagctgga ctacacaacc gatacacaga aaattcactt   1440
cggggcgtga tcctggatat acactttctc tcccaggctg acttccttgt gtgtactttt   1500
tcatcccagg tctgtagggt tgcttatgaa atcatgcaaa cactgcatcc tgatgcctct   1560
gcaaacttcc attctttaga tgacatctac tattttggag ccaaaatgc ccacaaccag   1620 attgcagttt atcctcacca acctcgaact aaagaggaaa tccccatgga acctggagat   1680
atcattggtg tggctggaaa ccattggaat ggttactcta aggtgtcaa cagaaaacta   1740 ggaaaaacag gcctgtaccc ttcctacaaa gtccgagaga agatagaaac agtcaaatac   1800
```

| | |
|---|---:|
| cctacatatc ctgaagctga aaaatagaga tggagtgtaa gagattaaca acagaattta | 1860 |
| gttcagacca tctcagccaa gcagaagacc cagactaaca tatggttcat tgacagacat | 1920 |
| gctccgcacc aagagcaagt gggaaccctc agatgctgca ctggtggaac gcctctttgt | 1980 |
| gaagggctgc tgtgccctca agcccatg | 2008 |

<210> SEQ ID NO 12
<211> LENGTH: 1728
<212> TYPE: DNA
<213> ORGANISM: Mus musculus

<400> SEQUENCE: 12

| | |
|---|---:|
| atgcgggcat ggactggttc ctggcgttgg attatgctca ttcttttgc ctgggggacc | 60 |
| ttgttatttt atataggtgg tcatttggtt cgagataatg accaccctga tcactccagc | 120 |
| agagaactct ccaagattct tgcaaagctt gaacgcttaa acagcaaaa tgaagacttg | 180 |
| aggcgaatgg ctgagtctct ccgaatacca gaaggcccca ttgaccaggg gacagctaca | 240 |
| ggaagagtcc gtgttttaga gaacagcttg gttaaggcca agaacagat tgaaaattac | 300 |
| aagaaacaag ctagaaatgg tctggggaag gatcatgaaa tcttaagaag gaggattgaa | 360 |
| aatggagcta agagctctg gtttttttcta caaagcgaac tgaagaaatt aaagcattta | 420 |
| gaaggaaatg aactccaaag acatgcagat gaaattcttt tggatttagg acaccatgaa | 480 |
| aggtctatca tgacagatct atactacctc agtcaaacag atggagcagg ggattggcgt | 540 |
| gaaaagagg ccaagatct gacagagctg gtccagcgga gaataacata tctccagaat | 600 |
| cctaaggact gcagcaaagc caggaagctg gtgtgtaaca tcaataaagg ctgtggctat | 660 |
| ggttgtcaac tccatcacgt ggtctactgt ttcatgattg cttatggcac ccagcgaaca | 720 |
| ctcatcttgg aatctcagaa ttggcgctat gctactggtg gatgggagac tgtgtttaga | 780 |
| cctgtaagtg agacatgtac agacagatct ggcctctcca ctggacactg gtcaggtgaa | 840 |
| gtaaatgaca aaaacattca agtggtcgag ctccccattg tagacagcct ccatcctcgg | 900 |
| cctcctact taccactggc tgttccagaa gaccttgcag accgactcct aagagtccat | 960 |
| ggtgaccctg cagtgtggtg ggtgtcccag tttgtcaaat acttgattcg tccacaacct | 1020 |
| tggctggaaa aggaaataga agaagccacc aagaagcttg gcttcaaaca tccagttatt | 1080 |
| ggagtccatg tcagacgcac agacaaagtg ggaacagaag cagccttcca ccccatcgag | 1140 |
| gagtacatgg tacacgttga agaacatttt cagcttctcg cacgcagaat gcaagtggat | 1200 |
| aaaaaaagag tatatctggc tactgatgat cctactttgt taaggaggc aaagacaaag | 1260 |
| tactccaatt atgaatttat tagtgataac tctatttctt ggtcagctgg actacacaat | 1320 |
| cggtacacag aaaattcact tcggggtgtg atcctggata tacactttct ctcacaggct | 1380 |
| gactttctag tgtgtacttt ttcatcccag gtctgtcggg ttgcttatga atcatgcaa | 1440 |
| accctgcatc ctgatgcctc tgcgaacttc cattctttgg atgacatcta ctattttgga | 1500 |
| ggccaaaatg cccacaatca gattgctgtt tatcctcaca aacctcgaac tgaagaggaa | 1560 |
| attccaatgg aacctggaga tatcattggt gtggctgaa accattggga tggttattct | 1620 |
| aaaggtatca acagaaaact tggaaaaaca ggcttatatc cctcctacaa agtccgagag | 1680 |
| aagatagaaa cagtcaagta tcccacatat cctgaagctg aaaaatag | 1728 |

<210> SEQ ID NO 13
<211> LENGTH: 575
<212> TYPE: PRT

<213> ORGANISM: Cricetulus griseus

<400> SEQUENCE: 13

```
Met Arg Ala Trp Thr Gly Ser Trp Arg Trp Ile Met Leu Ile Leu Phe
 1               5                  10                  15

Ala Trp Gly Thr Leu Leu Phe Tyr Ile Gly Gly His Leu Val Arg Asp
            20                  25                  30

Asn Asp His Pro Asp His Ser Ser Arg Glu Leu Ser Lys Ile Leu Ala
        35                  40                  45

Lys Leu Glu Arg Leu Lys Gln Gln Asn Glu Asp Leu Arg Arg Met Ala
50                  55                  60

Glu Ser Leu Arg Ile Pro Glu Gly Pro Ile Asp Gln Gly Thr Ala Thr
65                  70                  75                  80

Gly Arg Val Arg Val Leu Glu Glu Gln Leu Val Lys Ala Lys Glu Gln
                85                  90                  95

Ile Glu Asn Tyr Lys Lys Gln Ala Arg Asn Asp Leu Gly Lys Asp His
            100                 105                 110

Glu Ile Leu Arg Arg Arg Ile Glu Asn Gly Ala Lys Glu Leu Trp Phe
        115                 120                 125

Phe Leu Gln Ser Glu Leu Lys Lys Leu Lys Lys Leu Glu Gly Asn Glu
130                 135                 140

Leu Gln Arg His Ala Asp Glu Ile Leu Leu Asp Leu Gly His His Glu
145                 150                 155                 160

Arg Ser Ile Met Thr Asp Leu Tyr Tyr Leu Ser Gln Thr Asp Gly Ala
                165                 170                 175

Gly Glu Trp Arg Glu Lys Glu Ala Lys Asp Leu Thr Glu Leu Val Gln
            180                 185                 190

Arg Arg Ile Thr Tyr Leu Gln Asn Pro Lys Asp Cys Ser Lys Ala Arg
        195                 200                 205

Lys Leu Val Cys Asn Ile Asn Lys Gly Cys Gly Tyr Gly Cys Gln Leu
210                 215                 220

His His Val Val Tyr Cys Phe Met Ile Ala Tyr Gly Thr Gln Arg Thr
225                 230                 235                 240

Leu Ile Leu Glu Ser Gln Asn Trp Arg Tyr Ala Thr Gly Gly Trp Glu
                245                 250                 255

Thr Val Phe Arg Pro Val Ser Glu Thr Cys Thr Asp Arg Ser Gly Leu
            260                 265                 270

Ser Thr Gly His Trp Ser Gly Glu Val Lys Asp Lys Asn Val Gln Val
        275                 280                 285

Val Glu Leu Pro Ile Val Asp Ser Leu His Pro Arg Pro Pro Tyr Leu
290                 295                 300

Pro Leu Ala Val Pro Glu Asp Leu Ala Asp Arg Leu Leu Arg Val His
305                 310                 315                 320

Gly Asp Pro Ala Val Trp Trp Val Ser Gln Phe Val Lys Tyr Leu Ile
                325                 330                 335

Arg Pro Gln Pro Trp Leu Glu Arg Glu Ile Glu Glu Thr Thr Lys Lys
            340                 345                 350

Leu Gly Phe Lys His Pro Val Ile Gly Val His Val Arg Arg Thr Asp
        355                 360                 365

Lys Val Gly Thr Glu Ala Ala Phe His Pro Ile Glu Glu Tyr Met Val
370                 375                 380

His Val Glu Glu His Phe Gln Leu Leu Glu Arg Arg Met Lys Val Asp
385                 390                 395                 400
```

```
Lys Lys Arg Val Tyr Leu Ala Thr Asp Asp Pro Ser Leu Leu Lys Glu
                405                 410                 415

Ala Lys Thr Lys Tyr Ser Asn Tyr Glu Phe Ile Ser Asp Asn Ser Ile
            420                 425                 430

Ser Trp Ser Ala Gly Leu His Asn Arg Tyr Thr Glu Asn Ser Leu Arg
        435                 440                 445

Gly Val Ile Leu Asp Ile His Phe Leu Ser Gln Ala Asp Phe Leu Val
    450                 455                 460

Cys Thr Phe Ser Ser Gln Val Cys Arg Val Ala Tyr Glu Ile Met Gln
465                 470                 475                 480

Thr Leu His Pro Asp Ala Ser Ala Asn Phe His Ser Leu Asp Asp Ile
                485                 490                 495

Tyr Tyr Phe Gly Gly Gln Asn Ala His Asn Gln Ile Ala Val Tyr Pro
            500                 505                 510

His Gln Pro Arg Thr Lys Glu Glu Ile Pro Met Glu Pro Gly Asp Ile
        515                 520                 525

Ile Gly Val Ala Gly Asn His Trp Asn Gly Tyr Ser Lys Gly Val Asn
    530                 535                 540

Arg Lys Leu Gly Lys Thr Gly Leu Tyr Pro Ser Tyr Lys Val Arg Glu
545                 550                 555                 560

Lys Ile Glu Thr Val Lys Tyr Pro Thr Tyr Pro Glu Ala Glu Lys
                565                 570                 575

<210> SEQ ID NO 14
<211> LENGTH: 575
<212> TYPE: PRT
<213> ORGANISM: Mus musculus

<400> SEQUENCE: 14

Met Arg Ala Trp Thr Gly Ser Trp Arg Trp Ile Met Leu Ile Leu Phe
  1               5                  10                  15

Ala Trp Gly Thr Leu Leu Phe Tyr Ile Gly His Leu Val Arg Asp
             20                  25                  30

Asn Asp His Pro Asp His Ser Ser Arg Glu Leu Ser Lys Ile Leu Ala
         35                  40                  45

Lys Leu Glu Arg Leu Lys Gln Gln Asn Glu Asp Leu Arg Arg Met Ala
     50                  55                  60

Glu Ser Leu Arg Ile Pro Glu Gly Pro Ile Asp Gln Gly Thr Ala Thr
 65                  70                  75                  80

Gly Arg Val Arg Val Leu Glu Glu Gln Leu Val Lys Ala Lys Glu Gln
                 85                  90                  95

Ile Glu Asn Tyr Lys Lys Gln Ala Arg Asn Gly Leu Gly Lys Asp His
            100                 105                 110

Glu Ile Leu Arg Arg Arg Ile Glu Asn Gly Ala Lys Glu Leu Trp Phe
        115                 120                 125

Phe Leu Gln Ser Glu Leu Lys Lys Leu Lys His Leu Glu Gly Asn Glu
    130                 135                 140

Leu Gln Arg His Ala Asp Glu Ile Leu Leu Asp Leu Gly His His Glu
145                 150                 155                 160

Arg Ser Ile Met Thr Asp Leu Tyr Tyr Leu Ser Gln Thr Asp Gly Ala
                165                 170                 175

Gly Asp Trp Arg Glu Lys Glu Ala Lys Asp Leu Thr Glu Leu Val Gln
            180                 185                 190

Arg Arg Ile Thr Tyr Leu Gln Asn Pro Lys Asp Cys Ser Lys Ala Arg
        195                 200                 205
```

```
Lys Leu Val Cys Asn Ile Asn Lys Gly Cys Gly Tyr Gly Cys Gln Leu
    210                 215                 220

His His Val Val Tyr Cys Phe Met Ile Ala Tyr Gly Thr Gln Arg Thr
225                 230                 235                 240

Leu Ile Leu Glu Ser Gln Asn Trp Arg Tyr Ala Thr Gly Gly Trp Glu
                245                 250                 255

Thr Val Phe Arg Pro Val Ser Glu Thr Cys Thr Asp Arg Ser Gly Leu
            260                 265                 270

Ser Thr Gly His Trp Ser Gly Glu Val Asn Asp Lys Asn Ile Gln Val
        275                 280                 285

Val Glu Leu Pro Ile Val Asp Ser Leu His Pro Arg Pro Pro Tyr Leu
    290                 295                 300

Pro Leu Ala Val Pro Glu Asp Leu Ala Asp Arg Leu Leu Arg Val His
305                 310                 315                 320

Gly Asp Pro Ala Val Trp Trp Val Ser Gln Phe Val Lys Tyr Leu Ile
                325                 330                 335

Arg Pro Gln Pro Trp Leu Glu Lys Glu Ile Glu Glu Ala Thr Lys Lys
            340                 345                 350

Leu Gly Phe Lys His Pro Val Ile Gly Val His Val Arg Arg Thr Asp
        355                 360                 365

Lys Val Gly Thr Glu Ala Ala Phe His Pro Ile Glu Glu Tyr Met Val
    370                 375                 380

His Val Glu Glu His Phe Gln Leu Leu Ala Arg Arg Met Gln Val Asp
385                 390                 395                 400

Lys Lys Arg Val Tyr Leu Ala Thr Asp Asp Pro Thr Leu Leu Lys Glu
                405                 410                 415

Ala Lys Thr Lys Tyr Ser Asn Tyr Glu Phe Ile Ser Asp Asn Ser Ile
            420                 425                 430

Ser Trp Ser Ala Gly Leu His Asn Arg Tyr Thr Glu Asn Ser Leu Arg
        435                 440                 445

Gly Val Ile Leu Asp Ile His Phe Leu Ser Gln Ala Asp Phe Leu Val
    450                 455                 460

Cys Thr Phe Ser Ser Gln Val Cys Arg Val Ala Tyr Glu Ile Met Gln
465                 470                 475                 480

Thr Leu His Pro Asp Ala Ser Ala Asn Phe His Ser Leu Asp Asp Ile
                485                 490                 495

Tyr Tyr Phe Gly Gly Gln Asn Ala His Asn Gln Ile Ala Val Tyr Pro
            500                 505                 510

His Lys Pro Arg Thr Glu Glu Ile Pro Met Glu Pro Gly Asp Ile
        515                 520                 525

Ile Gly Val Ala Gly Asn His Trp Asp Gly Tyr Ser Lys Gly Ile Asn
    530                 535                 540

Arg Lys Leu Gly Lys Thr Gly Leu Tyr Pro Ser Tyr Lys Val Arg Glu
545                 550                 555                 560

Lys Ile Glu Thr Val Lys Tyr Pro Thr Tyr Pro Glu Ala Glu Lys
                565                 570                 575

<210> SEQ ID NO 15
<211> LENGTH: 383
<212> TYPE: DNA
<213> ORGANISM: Cricetulus griseus

<400> SEQUENCE: 15
gttaactggg gctcttttaa accctgaatt tttctaaatc cccacctcca agagtttggt    60
```

```
ttaaactgat ttttttaatg aatacctttt gaagaataga gcattgtctc atcatgcaaa      120
gcttctcagg gattcagcta gcatgttgaa gaaacataag ggtgttaaat tgtttgtcac      180
aagtgctgaa taaatattga cgtagtcttc agctattcta tactggaagt agatgatatt      240
ctcattggaa attctgttag gaagtaaccc ttcttgtctt cttacctgca tagaatccca      300
ggatataaaa cttgtgcttg tcgcccttgc cattgtctct cactggtggc ctttattgca      360
tctcatatct gccttctctt tcc                                              383

<210> SEQ ID NO 16
<211> LENGTH: 564
<212> TYPE: DNA
<213> ORGANISM: Cricetulus griseus

<400> SEQUENCE: 16
taagaattcc tgtgcccagc tgtatgtgag gctctctgca ggtgtaggga tgtttctgct       60
ttctttctgc acatgcttca cagctgaagt cctttgggtg tgagattgac attcagatag      120
actaaagtga ctggacttgt tgggaaacat actgtatgca ttattgccgt tgcctccagg      180
tgaaattaac acctcattca ccaatccctg ttcatccaaa ctttctaccc acatcacttt      240
aaatagaaat tagacccaat atgactcctt ttttcctaag ctgtttatag agattgtgct      300
ggagcagtga gcttttgtgt ttgtttgttt gttttgtaat tttccccatg aaaatttctc      360
taaactcaaa cctaagaggg aaaaaaaaaa aacagactta tatgtgccac acttgtaaaa      420
aaaaatcatg aaagatgtat atgatatttt taaacagttt gaatattaag atcacaattt      480
ctattttaaa aacaatcttg ttttacatat caatcaccca attcccttgc cttcccatcc      540
tcccattccc cccactgatc cccc                                             564

<210> SEQ ID NO 17
<211> LENGTH: 120
<212> TYPE: DNA
<213> ORGANISM: Cricetulus griseus

<400> SEQUENCE: 17
atgaatgttc attctttggg tatatgccca agagtagaat tgctaaatat tgaggtagac       60
tgattcccat tttcttgagg agtcgccata ttgatttcca aagtgactgt acaagttaac      120

<210> SEQ ID NO 18
<211> LENGTH: 274
<212> TYPE: DNA
<213> ORGANISM: Cricetulus griseus

<400> SEQUENCE: 18
aggcactagg taaatatttt tgaagaaaga atgagtatct cctatttcag aaaaactttt       60
attgacttaa atttaggata tcagaattag aaaacagtaa aaatttatag gagagttttt      120
aatgaatgtt atttttaaggt tccatacaaa tagtaattaa aacttacaca aactatttgt      180
agtaatgatt cagtctggta taccctgatg agcattatac acttttaaat tcttttttgta      240 aattttttta ttagttcaaa ttaggaacaa gctt                                  274

<210> SEQ ID NO 19
<211> LENGTH: 9196
<212> TYPE: DNA
<213> ORGANISM: Cricetulus griseus

<400> SEQUENCE: 19
```

```
tctagaccag gctggtctcg aactcacaga gaaccacctg cctctgccac ctgagtgctg      60
ggattaaagg tgtgcaccac caccgcccgg cgtaaaatca tattttttgaa tattgtgata   120 atttacatta taattgtaag taaaaatttt cagcctattt tgttatacat ttttgcgtaa   180
attattcttt tttgaaagtt tgttgtcca taatagtcta gggaaacata aagttataat    240
ttttgtctat gtatttgcat atatatctat ttaatctcct aatgtccagg aaataaatag   300
ggtatgtaat agcttcaaca tgtggtatga tagaattttt cagtgctata taagttgtta   360
cagcaaagtg ttattaattc atatgtccat atttcaattt tttatgaatt attaaattga   420
atccttaagc tgccagaact agaatttat tttaatcagg aagccccaaa tctgttcatt    480 cttctatat atgtggaaag gtaggcctca ctaactgatt cttcacctgt tttagaacat    540
ggtccaagaa tggagttatg taaggggaat tacaagtgtg agaaaactcc tagaaaacaa   600
gatgagtctt gtgaccttag tttctttaaa aacacaaaat tcttggaatg tgttttcatg   660
ttcctcccag gtggatagga gtgagtttat ttcagattat ttattacaac tggctgttgt   720
tacttgtttc tatgtcttta tagaaaaaca tattttttttt gccacatgca gcttgtcctt  780
atgattttat acttgtgtga ctcttaactc tcagagtata aattgtctga tgctatgaat   840
aaagttggct attgtatgag acttcagccc acttcaatta ttggcttcat tctctcagat   900
cccaccacct ccagagtggt aaacaacttg aaccattaaa cagactttag tctttatttg   960
aatgatagat ggggatatca gatttatagg cacagggttt tgagaaaggg agaaggtaaa  1020
cagtagagtt taacaacaac aaaaagtata ctttgtaaac gtaaaactat ttattaaagt  1080
agtagacaag acattaaata ttccttggga ttagtgcttt ttgaattttg ctttcaaata  1140
atagtcagtg agtatacccc tcccccattc tatattttag cagaaatcag aataaatggt  1200
gtttctggta cattcttttg tagagaattt attttctttg ggttttttgtg catttaaagt 1260 caataaaaat taaggttcag taatagaaaa aaaactctga ttttttggaat cccctttctt 1320 cagcttttct atttaatctc ttaatgataa tttaatttgt ggccatgtgg tcaaagtata  1380
tagccttgta tatgtaaatg ttttaaccaa cctgccttta cagtaactat ataatttat   1440 tctataatat atgactttc ttccatagct ttagagttgc ccagtcactt taagttacat   1500
tttcatatat gttctttgtg ggaggagata attttatttc taagagaatc ctaagcatac  1560
tgattgagaa atggcaaaca aaacacataa ttaaagctga taaagaacga acatttggag  1620
tttaaaatac atagccaccc taagggttta actgttgtta gccttctttt ggaattttta  1680
ttagttcata tagaaaaatg gatttatcg tgacatttcc atatatgtat ataatatatt   1740
tacatcatat ccacctgtaa ttattagtgt ttttaaatat atttgaaaaa ataatggtct  1800
ggtttgatcc atttgaacct tttgatgttt ggtgtggttg ccaattggtt gatggttatg  1860
ataacctttg cttctctaag gttcaagtca gtttgagaat atgtcctcta aaaatgacag  1920
gttgcaagtt aagtagtgag atgacagcga gatggagtga tgagaatttg tagaaatgaa  1980
ttcacttata ctgagaactt gttttgcttt tagataatga acatattagc ctgaagtaca  2040
tagccgaatt gattaattat tcaaagatat aatcttttaa tccctataaa agaggtatta  2100
cacaacaatt caagaaagat agaattagac ttccagtatt ggagtgaacc atttgttatc  2160
aggtagaacc ctaacgtgtg tggttgactt aaagtgttta cttttacct gatactgggt   2220 agctaattgt ctttcagcct cctggccaaa gataccatga aagtcaactt acgttgtatt  2280
ctatatctca aacaactcag ggtgtttctt actctttcca cagcatgtag agcccaggaa  2340
gcacaggaca agaaagctgc ctccttgtat caccaggaag atcttttttgt aagagtcatc 2400
```

-continued

```
acagtatacc agagagacta attttgtctg aagcatcatg tgttgaaaca acagaaactt    2460
attttcctgt gtggctaact agaaccagag tacaatgttt ccaattcttt gagctccgag    2520
aagacagaag ggagttgaaa ctctgaaaat gcgggcatgg actggttcct ggcgttggat    2580
tatgctcatt cttttgcct gggggacctt attgttttat ataggtggtc atttggttcg    2640
agataatgac caccctgacc attctagcag agaactctcc aagattcttg caaagctgga    2700
gcgcttaaaa caacaaaatg aagacttgag gagaatggct gagtctctcc ggtaggtttg    2760
aaatactcaa ggatttgatg aaatactgtg cttgaccttt aggtataggg tctcagtctg    2820
ctgttgaaaa atataatttc tacaaaccgt ctttgtaaaa ttttaagtat tgtagcagac    2880
tttttaaaag tcagtgatac atctatatag tcaatatagg tttacatagt tgcaatctta    2940
ttttgcatat gaatcagtat atagaagcag tggcatttat atgcttatgt tgcatttaca    3000
attatgttta gacgaacaca aactttatgt gatttggatt agtgctcatt aaatttttt    3060 attctatgga ctacaacaga gacataaatt ttgaaaggct tagttactct taaattctta    3120
tgatgaaaag caaaaattca ttgttaaata gaacagtgca tccggaatgt gggtaattat    3180
tgccatattt ctagtctact aaaaattgtg gcataactgt tcaaagtcat cagttgtttg    3240
gaaagccaaa gtctgattta aatggaaaac ataaacaatg atatctattt ctagataccct    3300 ttaacttgca gttactgagt ttacaagttg tctgacaact ttggattctc ttacttcata    3360
tctaagaatg atcatgtgta cagtgcttac tgtcacttta aaaaactgca gggctagaca    3420
tgcagatatg aagactttga cattagatgt ggtaattggc actaccagca agtggtatta    3480
agatacagct gaatatatta cttttgagg aacataattc atgaatggaa agtggagcat    3540
tagagaggat gccttctggc tctcccacac cactgtttgc atccattgca tttcacactg    3600
cttttagaac tcagatgttt catatggtat attgtgtaac tcaccatcag ttttatcttt    3660 aaaatgtctat ggatgataat gttgtatgtt aacacttta caaaaacaaa tgaagccata    3720
tcctcggtgt gagttgtgat ggtggtaatt gtcacaatag gattattcag caaggaacta    3780
agtcagggac aagaagtggg cgatactttg ttggattaaa tcattttact ggaagttcat    3840
cagggagggt tatgaaagtt gtggtctttg aactgaaatt atatgtgatt cattattctt    3900
gatttaggcc ttgctaatag taactatcat ttattgggaa tttgtcatat gtgccaattt    3960
gtcatgggcc agacagcgtg ttttactgaa tttctagata tctttatgag attctagtac    4020
tgttttcagc cattttacag atgaagaatc ttaaaaaatg ttaaataatt tagttttgccc    4080 aagattatac gttaacaaat ggtagaacct tctttgaatt ctggcagtat ggctacacag    4140
tccgaactct tatcttccta agctgaaaac agaaaaagca atgacccaga aaattttatt    4200
taaaagtctc aggagagact tcccatcctg agaagatctc ttttcccttt tataatttag    4260
gctcctgaat aatcactgaa ttttctccat gttccatcta tagtactgtt atttctgttt    4320 tcctttttc ttaccacaaa gtatcttgtt tttgctgtat gaaagaaaat gtgttattgt    4380
aatgtgaaat tctctgtccc tgcagggtcc cacatccgcc tcaatcccaa ataaacacac    4440
agaggctgta ttaattatga aactgttggt cagttggcta gggcttctta ttggctagct    4500
ctgtcttaat tattaaacca taactactat tgtaagtatt ccatgtggt cttatcttac    4560 caaggaaagg gtccagggac ctcttactcc tctggcgtgt tggcagtgaa gaggagagag    4620
cgatttccta tttgtctctg cttatttct gattctgctc agctatgtca cttcctgcct    4680
ggccaatcag ccaatcagtg ttttattcat tagccaataa aagaaacatt tacacagaag    4740
```

```
gacttccccc atcatgttat ttgtatgagt tcttcagaaa atcatagtat cttttaatac    4800
taattttat aaaaaattaa ttgtattgaa aattatgtgt atatgtgtct gtgtgtcgat     4860
ttgtgctcat aagtagcatg gagtgcagaa gagggaatca gatctttttt taagggacaa   4920
agagtttatt cagattacat tttaaggtga taatgtatga ttgcaaggtt atcaacatgg   4980
cagaaatgtg aagaagctgg tcacattaca tccagagtca agagtagaga gcaatgaatt   5040
gatgcatgca ttcctgtgct cagctcactt ttcctggagc tgagctgatt gtaagccatc   5100
tgatgtcttt gctgggaact aactcaaagg caagttcaaa acctgttctt aagtataagc   5160
catctctcca gtccctcata tggtctctta agacactttc tttatattct tgtacataga   5220
aattgaattc ctaacaactg cattcaaatt acaaatagt ttttaaaagc tgatataata    5280
aatgtaaata caatctagaa cattttata aataagcata ttaactcagt aaaaataaat    5340
gcatggttat tttccttcat tagggaagta tgtctcccca ggctgttctc tagattctac   5400
tagtaatgct gtttgtacac catccacagg ggttttattt taaagctaag acatgaatga   5460
tggacatgct tgttagcatt tagactttt tccttactat aattgagcta gtattttgt     5520
gctcagtttg atatctgtta attcagataa atgtaatagt aggtaatttc tttgtgataa   5580
aggcatataa attgaagttg gaaaacaaaa gcctgaaatg acagttttta agattcagaa   5640
caataatttt caaaagcagt tacccaactt tccaaataca atctgcagtt ttcttgatat   5700
gtgataaatt tagacaaaga aatagcacat tttaaaatag ctatttactc ttgattttt    5760
tttcaaattt aggctagttc actagttgtg tgtaaggtta tggctgcaaa catcttgac    5820
tcttggttag ggaatccagg atgatttacg tgtttggcca aaatcttgtt ccattctggg   5880
tttcttctct atctaggtag ctagcacaag ttaaaggtgt ggtagtattg gaaggctctc   5940
aggtatatat ttctatattc tgtattttt tcctctgtca tatatttgct ttctgtttta   6000
ttgatttcta ctgttagttt gatacttact ttcttacact ttctttggga tttattttgc   6060
tgttctaaga tttcttagca agttcatatc actgattta acagttgctt cttttgtaat    6120
atagactgaa tgccccttat ttgaaatgct tgggatcaga aactcagatt tgaactttc    6180
tttttaata tttccatcaa gtttaccagc tgaatgtcct gatccaagaa tatgaaatct    6240
gaaatgcttt gaaatctgaa acttttagag tgataaagct tcccttaaa ttaatttgtg    6300
ttctatattt tttgacaatg tcaacctttc attgttatcc aatgagtgaa catattttca   6360
atttttttgt ttgatctgtt atattttgat ctgaccatat ttataaaatt ttatttaatt   6420
tgaatgttgt gctgttactt atctttatta ttattttgc ttattttcta gccaaatgaa    6480
attatattct gtattatttt agtttgaatt ttacttttgtg gcttagtaac tgccttttgt   6540
tggtgaatgc ttaagaaaaa cgtgtggtct actgatattg gttctaatct tatatagcat   6600
gttgtttgtt aggtagttga ttatgctggt cagattgtct tgagtttatg caaatgtaaa   6660
atatttagat gcttgttttg ttgtctaaga acaaagtatg cttgctgtct cctatccggtt   6720
ctggttttc cattcatctc ttcaagctgt tttgtgtgtt gaatactaac tccgtactat    6780
cttgttttct gtgaattaac ccctttcaa aggtttcttt tcttttttt tttaagggac     6840
aacaagttta ttcagattac attttaagct gataatgtat gattgcaagg ttatcaacat   6900
ggcagaaatg tgaagaagct aggcacatta catccacatg gagtcaagag cagagagcag   6960
tgaattaatg catgcattcc tgtggtcagc tcactttcc tattcttaga tagtctagga    7020
tcataaacct ggggaatagt gctaccacaa tgggcatatc cacttacttc agttcatgca   7080
atcaaccaag gcacatccac aggaaaaact gatttagaca acctctcatt gagactcttc   7140
```

```
ccagatgatt agactgtgtc aagttgacaa ttaaaactat cacacctgaa gccatcacta    7200
gtaaatataa tgaaaatgtt gattatcacc ataattcatc tgtatcccct tgttattgta    7260
gattttgtga agttcctatt caagtccctg ttccttcctt aaaaacctgt tttttagtta    7320
aataggtttt ttagtgttcc tgtctgtaaa tactttttta aagttagata ttattttcaa    7380
gtatgttctc ccagtctttg gcttgtattt tcatcccttc aatacatata tttttgtaat    7440 ttatttttt tatttaaatt agaaacaaag ctgcttttac atgtcagtct cagttccctc    7500 tccctccct cctccctgc tccccaccta agcccaatt ccaactcctt tcttctcccc    7560
aggaagggtg aggccctcca tgggggaaat cttcaatgtc tgtcatatca tttggagcag    7620
ggcctagacc ctccccagtg tgtctaggct gagagagtat ccctctatgt ggagagggct    7680
cccaaagttc atttgtgtac taggggtaaa tactgatcca ctatcagtgg ccccatagat    7740
tgtccggacc tccaaactga cttcctcctt cagggagtct ggaacagttc tatgctggtt    7800
tcccagatat cagtctgggg tccatgagca accccttgtt caggtcagtt gtttctgtag    7860
gtttccccag cccggtcttg accccttttgc tcatcacttc tccctctctg caactggatt    7920
ccagagttca gctcagtgtt tagctgtggg tgtctgcatc tgcttccatc agctactgga    7980
tgagggctct aggatggcat ataaggtagt catcagtctc attatcagag aagggctttt    8040
aaggtagcct cttgattatt gcttagattg ttagttgggg tcaaccttgt aggtctctgg    8100
acagtgacag aattctcttt aaacctataa tggctccctc tgtggtggta tcccttttct    8160
tgctctcatc cgttcctccc ctgactagat cttcctgctc cctcatgtcc tcctctcccc    8220 tcccctctc cccttctctt tcttctaact ccctctcccc tccacccacg atcccccatta    8280 gcttatgaga tcttgtcctt attttagcaa aaccttttg gctataaaat taattaattt    8340
aatatgctta tatcaggttt attttggcta gtatttgtat gtgtttggtt agtgttttta    8400
accttaattg acatgtatcc ttatatttag acacagattt aaatatttga agttttttt    8460 ttttttttt ttaaagattt atttattttt tatgtcttct gcctgcatgc cagaagaggg    8520
caccagatct cattcaaggt ggttgtgagc caccatgtgg ttgctgggaa ttgaactcag    8580
gacctctgga agaacagtca gtgctcttaa ccgctgagcc atctctccag ccctgaagt    8640 gttctttta aagaggatag cagtgcatca tttttccctt tgaccaatga ctcctacctt    8700
actgaattgt tttagccatt tatatgtaat gctgttacca ggtttacatt ttcttttatc    8760
ttgctaaatt tcttccctgt ttgtctcatc tcttattttt gtctgttgga ttatataggc    8820
tttttatttt ctgtttttac agtaagttat atcaaattaa aattattta tggaatgggt    8880 gtgttgacta catgtatgtc tgtgcaccat gtgctgacct ggtcttggcc agaagaaggt    8940
gtcatattct ctgaaactgg tattgtggat gttacgaact gccatagggt gctaggaatc    9000 aaacccagc tcctctggaa aagcagccac tgctctgagc cactgagtcc tctcttcaag    9060
caggtgatgc caacttttaa tggttaccag tggataagag tgcttgtatc tctagcaccc    9120
atgaaaattt atgcattgct atatgggctt gtcacttcag cattgtgtga cagagacagg    9180
aggatcccaa gagctc                                                    9196
```

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA primer

```
<400> SEQUENCE: 20
gagacttcag cccacttcaa ttattggc                                              28

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA primer

<400> SEQUENCE: 21
cttgtgtgac tcttaactct cagag                                                 25

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Primer
      binding with vector

<400> SEQUENCE: 22
gaggccactt gtgtagcgcc aagtg                                                 25

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Primer
      binding with vector

<400> SEQUENCE: 23
ccctcgagat aacttcgtat agc                                                   23

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      DNA primer

<400> SEQUENCE: 24
ggtaggcctc actaactg                                                         18

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA primer

<400> SEQUENCE: 25
catagaaaca agtaacaaca gccag                                                 25

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA primer
```

```
<400> SEQUENCE: 26
gtgagtccat ggctgtcact g                                              21

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA primer

<400> SEQUENCE: 27
cctgacttgg ctattctcag                                                20

<210> SEQ ID NO 28
<211> LENGTH: 43
<212> TYPE: DNA
<213> ORGANISM: Artificial Sequence
<220> FEATURE:
<223> OTHER INFORMATION: Description of Artificial Sequence: Synthetic
      DNA primer

<400> SEQUENCE: 28
cggaattcgc caccatgtat tccaatgtga taggaactgt aac                      43

<210> SEQ ID NO 29
<211> LENGTH: 36
<212> TYPE: DNA
<213> ORGANISM: Artificial Sequence
<220> FEATURE:
<223> OTHER INFORMATION: Description of Artificial Sequence: Synthetic
      DNA primer

<400> SEQUENCE: 29
cgggatcctt acttaacaca agggttggct actctg                              36

<210> SEQ ID NO 30
<211> LENGTH: 34
<212> TYPE: DNA
<213> ORGANISM: Artificial Sequence
<220> FEATURE:
<223> OTHER INFORMATION: Description of Artificial Sequence: Synthetic
      DNA primer

<400> SEQUENCE: 30
ctctatcgaa agcccagaa atcctccaag ttag                                 34

<210> SEQ ID NO 31
<211> LENGTH: 34
<212> TYPE: DNA
<213> ORGANISM: Artificial Sequence
<220> FEATURE:
<223> OTHER INFORMATION: Description of Artificial Sequence: Synthetic
      DNA primer

<400> SEQUENCE: 31
ctaacttgga ggatttctgg gcttttcgat agag                                34

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA primer

<400> SEQUENCE: 32
```
gatatcgctg cgctcgttgt cgac                                          24

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA primer

<400> SEQUENCE: 33
caggaaggaa ggctggaaaa gagc                                          24

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA primer

<400> SEQUENCE: 34
aagcccagga aggtggcgct catcac                                        26

<210> SEQ ID NO 35
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA primer

<400> SEQUENCE: 35
cactagttga ggcctggtag aacttcac                                      28

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA primer

<400> SEQUENCE: 36
tcctttgact tagctgagta caccg                                         25

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA primer

<400> SEQUENCE: 37
catagggtga cctcggatag aaagg                                         25

<210> SEQ ID NO 38
<211> LENGTH: 1504
<212> TYPE: DNA
<213> ORGANISM: Cricetulus griseus
<220> FEATURE:
<221> NAME/KEY: CDS
<222> LOCATION: (1)..(1119)

<400> SEQUENCE: 38

```
atg gct cac gct ccc gct agc tgc ccg agc tcc agg aac tct ggg gac    48
Met Ala His Ala Pro Ala Ser Cys Pro Ser Ser Arg Asn Ser Gly Asp
 1               5                  10                  15 ggc gat aag ggc aag ccc agg aag gtg gcg ctc atc acg ggc atc acc    96
Gly Asp Lys Gly Lys Pro Arg Lys Val Ala Leu Ile Thr Gly Ile Thr
             20                  25                  30 ggc cag gat ggc tca tac ttg gca gaa ttc ctg ctg gag aaa gga tac   144
Gly Gln Asp Gly Ser Tyr Leu Ala Glu Phe Leu Leu Glu Lys Gly Tyr
         35                  40                  45 gag gtt cat gga att gta cgg cga tcc agt tca ttt aat aca ggt cga   192
Glu Val His Gly Ile Val Arg Arg Ser Ser Ser Phe Asn Thr Gly Arg
     50                  55                  60 att gaa cat tta tat aag aat cca cag gct cat att gaa gga aac atg   240
Ile Glu His Leu Tyr Lys Asn Pro Gln Ala His Ile Glu Gly Asn Met
 65                  70                  75                  80 aag ttg cac tat ggt gac ctc acc gac agc acc tgc cta gta aaa atc   288
Lys Leu His Tyr Gly Asp Leu Thr Asp Ser Thr Cys Leu Val Lys Ile
                 85                  90                  95 atc aat gaa gtc aaa cct aca gag atc tac aat ctt ggt gcc cag agc   336
Ile Asn Glu Val Lys Pro Thr Glu Ile Tyr Asn Leu Gly Ala Gln Ser
            100                 105                 110 cat gtc aag att tcc ttt gac tta gca gag tac act gca gat gtt gat   384
His Val Lys Ile Ser Phe Asp Leu Ala Glu Tyr Thr Ala Asp Val Asp
        115                 120                 125 gga gtt ggc acc ttg cgg ctt ctg gat gca att aag act tgt ggc ctt   432
Gly Val Gly Thr Leu Arg Leu Leu Asp Ala Ile Lys Thr Cys Gly Leu
    130                 135                 140 ata aat tct gtg aag ttc tac cag gcc tca act agt gaa ctg tat gga   480
Ile Asn Ser Val Lys Phe Tyr Gln Ala Ser Thr Ser Glu Leu Tyr Gly
145                 150                 155                 160 aaa gtg caa gaa ata ccc cag aaa gag acc acc cct ttc tat cca agg   528
Lys Val Gln Glu Ile Pro Gln Lys Glu Thr Thr Pro Phe Tyr Pro Arg
                165                 170                 175 tcg ccc tat gga gca gcc aaa ctt tat gcc tat tgg att gta gtg aac   576
Ser Pro Tyr Gly Ala Ala Lys Leu Tyr Ala Tyr Trp Ile Val Val Asn
            180                 185                 190 ttt cga gag gct tat aat ctc ttt gcg gtg aac ggc att ctc ttc aat   624
Phe Arg Glu Ala Tyr Asn Leu Phe Ala Val Asn Gly Ile Leu Phe Asn
        195                 200                 205 cat gag agt cct aga aga gga gct aat ttt gtt act cga aaa att agc   672
His Glu Ser Pro Arg Arg Gly Ala Asn Phe Val Thr Arg Lys Ile Ser
    210                 215                 220 cgg tca gta gct aag att tac ctt gga caa ctg gaa tgt ttc agt ttg   720
Arg Ser Val Ala Lys Ile Tyr Leu Gly Gln Leu Glu Cys Phe Ser Leu
225                 230                 235                 240 gga aat ctg gac gcc aaa cga gac tgg ggc cat gcc aag gac tat gtc   768
Gly Asn Leu Asp Ala Lys Arg Asp Trp Gly His Ala Lys Asp Tyr Val
                245                 250                 255 gag gct atg tgg ctg atg tta caa aat gat gaa cca gag gac ttt gtc   816
Glu Ala Met Trp Leu Met Leu Gln Asn Asp Glu Pro Glu Asp Phe Val
            260                 265                 270 ata gct act ggg gaa gtt cat agt gtc cgt gaa ttt gtt gag aaa tca   864
Ile Ala Thr Gly Glu Val His Ser Val Arg Glu Phe Val Glu Lys Ser
        275                 280                 285 ttc atg cac att gga aag acc att gtg tgg gaa gga aag aat gaa aat   912
Phe Met His Ile Gly Lys Thr Ile Val Trp Glu Gly Lys Asn Glu Asn
    290                 295                 300 gaa gtg ggc aga tgt aaa gag acc ggc aaa att cat gtg act gtg gat   960
Glu Val Gly Arg Cys Lys Glu Thr Gly Lys Ile His Val Thr Val Asp
305                 310                 315                 320
```

-continued

```
ctg aaa tac tac cga cca act gaa gtg gac ttc ctg cag gga gac tgc      1008
Leu Lys Tyr Tyr Arg Pro Thr Glu Val Asp Phe Leu Gln Gly Asp Cys
            325                 330                 335 tcc aag gcg cag cag aaa ctg aac tgg aag ccc cgc gtt gcc ttt gac      1056
Ser Lys Ala Gln Gln Lys Leu Asn Trp Lys Pro Arg Val Ala Phe Asp
        340                 345                 350 gag ctg gtg agg gag atg gtg caa gcc gat gtg gag ctc atg aga acc      1104
Glu Leu Val Arg Glu Met Val Gln Ala Asp Val Glu Leu Met Arg Thr
    355                 360                 365 aac ccc aac gcc tga gcacctctac aaaaaaattc gcgagacatg gactatggtg      1159
Asn Pro Asn Ala
    370 cagagccagc caaccagagt ccagccactc ctgagaccat cgaccataaa ccctcgactg      1219 cctgtgtcgt ccccacagct aagagctggg ccacaggttt gtgggcacca ggacggggac      1279 actccagagc taaggccact cgcttttgt caaaggctcc tctcaatgat tttgggaaat       1339 caagaagttt aaaatcacat actcatttta cttgaaatta tgtcactaga caacttaaat      1399 ttttgagtct tgagattgtt tttctctttt cttattaaat gatctttcta tgacccagca      1459 aaaaaaaaaa aaaaaaggga tataaaaaaa aaaaaaaaaa aaaaa                      1504

<210> SEQ ID NO 39
<211> LENGTH: 1119
<212> TYPE: DNA
<213> ORGANISM: Homo sapiens
<220> FEATURE:
<221> NAME/KEY: CDS
<222> LOCATION: (1)..(1119)

<400> SEQUENCE: 39 atg gca cac gca ccg gca cgc tgc ccc agc gcc cgg ggc tcc ggg gac       48
Met Ala His Ala Pro Ala Arg Cys Pro Ser Ala Arg Gly Ser Gly Asp
1               5                   10                  15 ggc gag atg ggc aag ccc agg aac gtg gcg ctc atc acc ggt atc aca       96
Gly Glu Met Gly Lys Pro Arg Asn Val Ala Leu Ile Thr Gly Ile Thr
            20                  25                  30 ggc cag gat ggt tcc tac ctg gct gag ttc ctg ctg gag aaa ggc tat      144
Gly Gln Asp Gly Ser Tyr Leu Ala Glu Phe Leu Leu Glu Lys Gly Tyr
        35                  40                  45 gag gtc cat gga att gta cgg cgg tcc agt tca ttt aat acg ggt cga      192
Glu Val His Gly Ile Val Arg Arg Ser Ser Ser Phe Asn Thr Gly Arg
    50                  55                  60 att gag cat ctg tat aag aat ccc cag gct cac att gaa gga aac atg      240
Ile Glu His Leu Tyr Lys Asn Pro Gln Ala His Ile Glu Gly Asn Met
65                  70                  75                  80 aag ttg cac tat ggc gat ctc act gac agt acc tgc ctt gtg aag atc      288
Lys Leu His Tyr Gly Asp Leu Thr Asp Ser Thr Cys Leu Val Lys Ile
                85                  90                  95 att aat gaa gta aag ccc aca gag atc tac aac ctt gga gcc cag agc      336
Ile Asn Glu Val Lys Pro Thr Glu Ile Tyr Asn Leu Gly Ala Gln Ser
            100                 105                 110 cac gtc aaa att tcc ttt gac ctc gct gag tac act gcg gac gtt gac      384
His Val Lys Ile Ser Phe Asp Leu Ala Glu Tyr Thr Ala Asp Val Asp
        115                 120                 125 gga gtt ggc act cta cga ctt cta gat gca gtt aag act tgt ggc ctt      432
Gly Val Gly Thr Leu Arg Leu Leu Asp Ala Val Lys Thr Cys Gly Leu
    130                 135                 140 atc aac tct gtg aag ttc tac caa gcc tca aca agt gaa ctt tat ggg      480
Ile Asn Ser Val Lys Phe Tyr Gln Ala Ser Thr Ser Glu Leu Tyr Gly
145                 150                 155                 160
```

```
aaa gtg cag gaa ata ccc cag aag gag acc acc cct ttc tat ccc cgg      528
Lys Val Gln Glu Ile Pro Gln Lys Glu Thr Thr Pro Phe Tyr Pro Arg
            165                 170                 175 tca ccc tat ggg gca gca aaa ctc tat gcc tat tgg att gtg gtg aac      576
Ser Pro Tyr Gly Ala Ala Lys Leu Tyr Ala Tyr Trp Ile Val Val Asn
        180                 185                 190 ttc cgt gag gcg tat aat ctc ttt gca gtg aac ggc att ctc ttc aat      624
Phe Arg Glu Ala Tyr Asn Leu Phe Ala Val Asn Gly Ile Leu Phe Asn
    195                 200                 205 cat gag agt ccc aga aga gga gct aat ttc gtt act cga aaa att agc      672
His Glu Ser Pro Arg Arg Gly Ala Asn Phe Val Thr Arg Lys Ile Ser
210                 215                 220 cgg tca gta gct aag att tac ctt gga caa ctg gaa tgt ttc agt ttg      720
Arg Ser Val Ala Lys Ile Tyr Leu Gly Gln Leu Glu Cys Phe Ser Leu
225                 230                 235                 240 gga aat ctg gat gcc aaa cga gat tgg ggc cat gcc aag gac tat gtg      768
Gly Asn Leu Asp Ala Lys Arg Asp Trp Gly His Ala Lys Asp Tyr Val
                245                 250                 255 gag gct atg tgg ttg atg ttg cag aat gat gag ccg gag gac ttc gtt      816
Glu Ala Met Trp Leu Met Leu Gln Asn Asp Glu Pro Glu Asp Phe Val
            260                 265                 270 ata gct act ggg gag gtc cat agt gtc cgg gaa ttt gtc gag aaa tca      864
Ile Ala Thr Gly Glu Val His Ser Val Arg Glu Phe Val Glu Lys Ser
        275                 280                 285 ttc ttg cac att gga aaa acc att gtg tgg gaa gga aag aat gaa aat      912
Phe Leu His Ile Gly Lys Thr Ile Val Trp Glu Gly Lys Asn Glu Asn
    290                 295                 300 gaa gtg ggc aga tgt aaa gag acc ggc aaa gtt cac gtg act gtg gat      960
Glu Val Gly Arg Cys Lys Glu Thr Gly Lys Val His Val Thr Val Asp
305                 310                 315                 320 ctc aag tac tac cgg cca act gaa gtg gac ttt ctg cag ggc gac tgc     1008
Leu Lys Tyr Tyr Arg Pro Thr Glu Val Asp Phe Leu Gln Gly Asp Cys
                325                 330                 335 acc aaa gcg aaa cag aag ctg aac tgg aag ccc cgg gtc gct ttc gat     1056
Thr Lys Ala Lys Gln Lys Leu Asn Trp Lys Pro Arg Val Ala Phe Asp
            340                 345                 350 gag ctg gtg agg gag atg gtg cac gcc gac gtg gag ctc atg agg aca     1104
Glu Leu Val Arg Glu Met Val His Ala Asp Val Glu Leu Met Arg Thr
        355                 360                 365 aac ccc aat gcc tga                                                  1119
Asn Pro Asn Ala
        370

<210> SEQ ID NO 40
<211> LENGTH: 1299
<212> TYPE: DNA
<213> ORGANISM: Homo sapiens
<220> FEATURE:
<221> NAME/KEY: CDS
<222> LOCATION: (1)..(1299)

<400> SEQUENCE: 40 cac ggg agc cct gtg gac atc tgc aca gcc aag ccg cgg gac att ccc       48
His Gly Ser Pro Val Asp Ile Cys Thr Ala Lys Pro Arg Asp Ile Pro
  1               5                  10                  15 atg aat ccc atg tgc att tac cgc tcc ccg gag aag aag gca act gag       96
Met Asn Pro Met Cys Ile Tyr Arg Ser Pro Glu Lys Lys Ala Thr Glu
             20                  25                  30 gat gag ggc tca gaa cag aag atc ccg gag gcc acc aac cgg cgt gtc      144
Asp Glu Gly Ser Glu Gln Lys Ile Pro Glu Ala Thr Asn Arg Arg Val
         35                  40                  45
```

```
tgg gaa ctg tcc aag gcc aat tcc cgc ttt gct acc act ttc tat cag      192
Trp Glu Leu Ser Lys Ala Asn Ser Arg Phe Ala Thr Thr Phe Tyr Gln
     50                  55                  60 cac ctg gca gat tcc aag aat gac aat gat aac att ttc ctg tca ccc      240
His Leu Ala Asp Ser Lys Asn Asp Asn Asp Asn Ile Phe Leu Ser Pro
 65                  70                  75                  80 ctg agt atc tcc acg gct ttt gct atg acc aag ctg ggt gcc tgt aat      288
Leu Ser Ile Ser Thr Ala Phe Ala Met Thr Lys Leu Gly Ala Cys Asn
                 85                  90                  95 gac acc ctc cag caa ctg atg gag gta ttt aag ttt gac acc ata tct      336
Asp Thr Leu Gln Gln Leu Met Glu Val Phe Lys Phe Asp Thr Ile Ser
             100                 105                 110 gag aaa aca tct gat cag atc cac ttc ttc ttt gcc aaa ctg aac tgc      384
Glu Lys Thr Ser Asp Gln Ile His Phe Phe Phe Ala Lys Leu Asn Cys
         115                 120                 125 cga ctc tat cga aaa gcc cag aaa tcc tcc aag tta gta tca gcc aat      432
Arg Leu Tyr Arg Lys Ala Gln Lys Ser Ser Lys Leu Val Ser Ala Asn
 130                 135                 140 cgc ctt ttt gga gac aaa tcc ctt acc ttc aat gag acc tac cag gac      480
Arg Leu Phe Gly Asp Lys Ser Leu Thr Phe Asn Glu Thr Tyr Gln Asp
145                 150                 155                 160 atc agt gag ttg gta tat gga gcc aag ctc cag ccc ctg gac ttc aag      528
Ile Ser Glu Leu Val Tyr Gly Ala Lys Leu Gln Pro Leu Asp Phe Lys
                 165                 170                 175 gaa aat gca gag caa tcc aga gcg gcc atc aac aaa tgg gtg tcc aat      576
Glu Asn Ala Glu Gln Ser Arg Ala Ala Ile Asn Lys Trp Val Ser Asn
             180                 185                 190 aag acc gaa ggc cga atc acc gat gtc att ccc tcg gaa gcc atc aat      624
Lys Thr Glu Gly Arg Ile Thr Asp Val Ile Pro Ser Glu Ala Ile Asn
         195                 200                 205 gag ctc act gtt ctg gtg ctg gtt aac acc att tac ttc aag ggc ctg      672
Glu Leu Thr Val Leu Val Leu Val Asn Thr Ile Tyr Phe Lys Gly Leu
     210                 215                 220 tgg aag tca aag ttc agc cct gag aac aca agg aag gaa ctg ttc tac      720
Trp Lys Ser Lys Phe Ser Pro Glu Asn Thr Arg Lys Glu Leu Phe Tyr
225                 230                 235                 240 aag gct gat gga gag tcg tgt tca gca tct atg atg tac cag gaa ggc      768
Lys Ala Asp Gly Glu Ser Cys Ser Ala Ser Met Met Tyr Gln Glu Gly
                 245                 250                 255 aag ttc cgt tat cgg cgc gtg gct gaa ggc acc cag gtg ctt gag ttg      816
Lys Phe Arg Tyr Arg Arg Val Ala Glu Gly Thr Gln Val Leu Glu Leu
             260                 265                 270 ccc ttc aaa ggt gat gac atc acc atg gtc ctc atc ttg ccc aag cct      864
Pro Phe Lys Gly Asp Asp Ile Thr Met Val Leu Ile Leu Pro Lys Pro
         275                 280                 285 gag aag agc ctg gcc aag gtg gag aag gaa ctc acc cca gag gtg ctg      912
Glu Lys Ser Leu Ala Lys Val Glu Lys Glu Leu Thr Pro Glu Val Leu
     290                 295                 300 cag gag tgg ctg gat gaa ttg gag gag atg atg ctg gtg gtt cac atg      960
Gln Glu Trp Leu Asp Glu Leu Glu Glu Met Met Leu Val Val His Met
305                 310                 315                 320 ccc cgc ttc cgc att gag gac ggc ttc agt ttg aag gag cag ctg caa     1008
Pro Arg Phe Arg Ile Glu Asp Gly Phe Ser Leu Lys Glu Gln Leu Gln
                 325                 330                 335 gac atg ggc ctt gtc gat ctg ttc agc cct gaa aag tcc aaa ctc cca     1056
Asp Met Gly Leu Val Asp Leu Phe Ser Pro Glu Lys Ser Lys Leu Pro
             340                 345                 350 ggt att gtt gca gaa ggc cga gat gac ctc tat gtc tca gat gca ttc     1104
Gly Ile Val Ala Glu Gly Arg Asp Asp Leu Tyr Val Ser Asp Ala Phe
```

-continued

| | 355 | | | | 360 | | | | | 365 | | | | |
|---|---|---|---|---|---|---|---|---|---|---|---|---|---|---|
| cat | aag | gca | ttt | ctt | gag | gta | aat | gaa | gaa | ggc | agt | gaa | gca | gct | gca | 1152 |
| His | Lys | Ala | Phe | Leu | Glu | Val | Asn | Glu | Glu | Gly | Ser | Glu | Ala | Ala | Ala | |
| | 370 | | | | | 375 | | | | | 380 | | | | |
| agt | acc | gct | gtt | gtg | att | gct | ggc | cgt | tcg | cta | aac | ccc | aac | agg | gtg | 1200 |
| Ser | Thr | Ala | Val | Val | Ile | Ala | Gly | Arg | Ser | Leu | Asn | Pro | Asn | Arg | Val | |
| 385 | | | | | 390 | | | | | 395 | | | | | 400 | |
| act | ttc | aag | gcc | aac | agg | ccc | ttc | ctg | gtt | ttt | ata | aga | gaa | gtt | cct | 1248 |
| Thr | Phe | Lys | Ala | Asn | Arg | Pro | Phe | Leu | Val | Phe | Ile | Arg | Glu | Val | Pro | |
| | | | | 405 | | | | | 410 | | | | | 415 | | |
| ctg | aac | act | att | atc | ttc | atg | ggc | aga | gta | gcc | aac | cct | tgt | gtt | aag | 1296 |
| Leu | Asn | Thr | Ile | Ile | Phe | Met | Gly | Arg | Val | Ala | Asn | Pro | Cys | Val | Lys | |
| | | | 420 | | | | | 425 | | | | | 430 | | | |
| taa | | | | | | | | | | | | | | | | 1299 |

US 7,691,810 B2

METHOD OF PRODUCING RECOMBINANT ANTITHROMBIN III COMPOSITION

The present application is based on and claims benefit of U.S. provisional application Ser. No. 60/572,898, filed 21 May 2004, and JP 2003-3501 64, filed 9 Oct. 2003, the entire contents of each of which is hereby incorporated by reference.

BACKGROUND OF THE INVENTION

1. Field of the Invention

The present invention relates to a process for producing an antithrombin III composition comprising an antithrombin III molecule having complex type N-glycoside-linked sugar chains, wherein the complex type N-glycoside-linked sugar chains have a structure in which fucose is not bound to N-acetylglucosamine in the reducing end in the sugar chains.

2. Brief Description of the Background Art

Thrombus formation accompanies a danger of stopping blood flow. Since cutoff of blood flow by the formation of thrombi becomes a lethal factor, the living body has several mechanisms to control and regulate blood coagulation. That is, direct inactivation of activated coagulation factors by serine protease [*The Thrombin*, Volume I (Machovich R., ed.), pp. 1-21, CRC Press, Boca Raton (1982)], a regulatory mechanism based on the degradation of factor V and factor VIII by activated protein C [*Progress in Hemostais and Thrombosis*, Volume 7 (Spaet T. H., ed.), pp. 25-54, Grune & Stratton, New York (1984)] and an inhibitory mechanism of activated coagulation factors by various serine protease inhibitors in blood. In addition, the presence of a tissue factor inhibitor which inhibits activation of factor VII in an activated factor X-dependent manner [*Journal of Japanese Society on Thrombosis and Hemostasis*, 2, 550 (1991)] has also been found. The most important mechanism among these is the inhibitory mechanism of activated coagulation factors by various serine protease inhibitors in blood.

Various serine protease inhibitors are present in blood, and their amount reaches 10% of the total plasma protein. It is known that 4 inhibitors among these inhibitors, namely antithrombin III, α1 proteinase inhibitor, α2 macroglobulin and heparin cofactor II, are important in regulating blood coagulation. Among such inhibitors, antithrombin III is particularly important and occupies 70% of the antithrombin activity in plasma.

Antithrombin III is a glycoprotein comprising 432 amino acids and having a molecular weight of approximately 59,000 to 65,000, and has three disulfide bonds, Cys8-Cys128, Cys21-Cys95 and Cys247-Cys430, in its molecule [*Proc. Natl. Acad. Sci., USA*, 80, 1845 (1983)). By these bonds, a large loop structure is formed on the C-terminal, and an Arg393-Ser394 bond is present as the active center in this loop structure (FIG. 1). Human antithrombin III has an isoelectric point of 5.11. N-Glycoside-linked sugar chains are added to 4 positions, the 96th, 135th, 155th and 192nd asparagine residues counting from the N-terminus (hereinafter referred to as Asn96, Asn135, Asn155 and Asn192, respectively) of antithrombin III. The antithrombin III in human plasma exists in two kinds of isoforms, an α type having four N-glycoside-linked sugar chains and a β type having only three N-glycoside-linked sugar chains but not having a sugar chain to the Asn135 [*Pathophysiol. Haemost. Thromb.*, 32, 143 (2002)), and in the antithrombin III in human plasma, 90 to 95% is the α type and the remaining 5 to 10% is the β type.

The complex type N-glycoside-linked sugar chains added to antithrombin III are constituted by N-acetylglucosamine, sialic acid, galactose and mannose (FIG. 2). One of the characteristics of the antithrombin III distributing in human plasma is that its sugar chain structure is free from the fucose modification.

Antithrombin III has been developed as a blood coagulation inhibitor and is broadly used in the world for the treatment of thrombosis based on congenital antithrombin III deficiency and multiple intravascular blood coagulation syndrome which accompanies reduction of antithrombin III.

Blood preparations such as antithrombin III are produced by using pooled human plasma samples as the raw material. In Japan, the pooled plasma is prepared at Plasma Fractionation Center, Japanese Red Cross Society, by mixing plasma samples of approximately 5,000 to 10,000 volunteers after completion of the 6 months of storage, and provided. In reality, in order to produce one lot of a blood preparation such as a dry concentrated human blood coagulation factor VIII preparation, Cross Eight M (Japanese Red Cross Society), several batches of cryoprecipitates obtained from the above-described pooled plasmas are necessary, and plasma samples of approximately 80,000 volunteers are used [*Japanese Journal of Transfusion Medicine*, 48, 27 (2002)].

The pooled plasma is produced by using blood samples provided by blood donors as the raw material, and it has been reported that the human parvovirus B19-positive ratio in blood donors in Japan is estimated to be 0.6 to 0.8% [*Journal of Japan Society of Blood Transfusion*, 42, 231 (1996)]. Thus, it is calculated that one lot equivalent to the above-described Cross Eight M is contaminated with human parvovirus B19-positive blood samples corresponding to roughly 480 to 640 donors. The human parvovirus B19 is a small virus of 18 to 26 nm in diameter without envelope, and keeps its resistance even after carrying out heat treatment at 60° C. for 30 minutes, acid treatment at approximately pH 3, chloroform treatment, surfactant treatment and the like [*Science*, 262, 114 (1993)], so that it cannot be eliminated by general virus elimination methods. Accordingly, elimination of human parvovirus B19 requires a step for filtration through an exclusively developed virus eliminating membrane having a pore size of several nanometers to several ten nanometers. However, it is considered that a filtration step which uses such a small membrane pore size, namely a nano-filtration step, is difficult to be introduced into the production process of many plasma fractionation preparations [*Japanese Journal of Transfusion Medicine*, 48, 27 (2002)]. It is considered that human parvovirus B19 is the cause of erythema infectiosum, and generally shows only transient cold-like symptoms in the case of healthy persons without anti-B19 antibody, but causes chronic hemolytic anemia in some cases. Also, it is said that it sometimes induces serious acute pure red cell aplasia in immunodeficiency patients. In addition, there is a report stating that pregnant women having no anti-B19 antibody sometimes result in miscarriage or the unborn babies cause edema, and 15% of the intrauterine fetal death was positive regarding the result of DNA inspection of B19 [*Lancet*, 357, 1494 (2001)]. In the dry concentrated human blood coagulation factor VIII preparation, Cross Eight M (Japanese Red Cross Society), a case in which a transient infection with human parvovirus B19 by the administration of this preparation was suspected was reported in September, 1997 [*Journal of Japanese Society of Child Hematology*, 11, 289 (1997)].

A hepatitis B virus-negative, hepatitis C virus-negative and human immunodeficiency virus I and II-negative pooled plasma is used as the production material of antithrombin III blood preparations such as Neuart (manufactured by Mitsubishi Pharma Corporation) and Anthrobin P (manufactured by Aventis Boehring), but the presence or absence of human parvovirus B19 in the raw material has not been confirmed.

Although a virus inactivation treatment at 60° C. for 10 hours, namely pasteurization, is carried out in the production process of antithrombin III blood preparations, there are problems such that the antithrombin III which is a protein is denatured, and AIDS virus, human parvovirus and prion which becomes the cause of mutation type Creutzfeldt-Jacob disease cannot be completely removed.

As described in the above, the use of blood preparations has disadvantages in that there is a risk of viral infection, and the risk cannot completely be excluded by the current techniques. Thus, an antithrombin III preparation with improved safety is in demand.

Accordingly, in order to provide human antithrombin III without using human plasma as the raw material, its replacement with a recombinant has been considered. However, the activity of the recombinant antithrombin III prepared by using gene recombination techniques is inferior to the activity of antithrombin III obtained from a natural material such as plasma. This is because it is considered that the sugar chain structure to be added to the recombinant is different from that of antithrombin III prepared from plasma, and specifically, it is assumed that since fucose is bound to the complex type N-glycoside-linked sugar chains to be added to the recombinant antithrombin III, its affinity with heparin becomes low, and therefore sufficient anti-blood coagulation activity cannot be obtained [*Journal of Biological Chemistry*, 268, 17588 (1993), *Biochemistry*, 35, 8881 (1996)). To date, there are reports on recombinant antithrombin III produced by a baby hamster kidney-derived BHK cell [*Journal of Biological Chemistry*, 268, 17588 (1993), *Biochemistry*, 35 8881 (1996)], a Chinese hamster ovary-derived CHO cell (WO02/02793) or a transgenic goat (US 2003096974), but fucose is bound to N-acetylglucosamine in the reducing end in the complex type N-glycoside-linked sugar chains binding to the recombinant antithrombin III in each of these cases. The ratio of the complex type N-glycoside-linked sugar chains to which fucose is bound to the total complex type N-glycoside-linked sugar chains in the produced recombinant antithrombin III varies depending on the host cell, but is estimated to be from 39 to 95%. Attempts have been made to reduce the ratio of the sugar chain in which fucose is bound to the complex type N-glycoside-linked sugar chains by various devices such as improvement of the culturing method, but it has not been succeeded yet in producing a recombinant antithrombin III having a sugar chain structure equivalent to that of the natural antithrombin III.

SUMMARY OF THE INVENTION

The present invention relates to the following (1) to (24):

(1) A process for producing an antithrombin III composition, which comprises culturing, in a medium, a transformant obtained by introducing a DNA encoding antithrombin III into a host cell modified by gene recombination to form and accumulate, in the culture, an antithrombin III composition comprising an antithrombin III molecule having complex type N-glycoside-linked sugar chains, wherein the complex type N-glycoside-linked sugar chains have a structure in which fucose is not bound to N-acetylglucosamine in the reducing end in the sugar chains; and recovering the antithrombin III composition from the culture.

(2) The process according to (1), wherein the complex type N-glycoside-linked sugar chains have a structure in which 1-position of fucose is not bound to 6-position of N-acetylglucosamine in the reducing end in the sugar chains.

(3) The process according to (1) or (2), wherein the host cell is a host cell in which genome is modified so as to have deleted activity of an enzyme relating to synthesis of an intracellular sugar nucleotide, GDP-fucose, or an enzyme relating to the modification of a sugar chain in which 1-position of fucose is bound to 6-position of N-acetylglucosamine in the reducing end through α-bond in a complex type N-glycoside-linked sugar chain.

(4) The process according to any one of (1) to (3), wherein the host cell is a host cell in which all of alleles on a genome encoding an enzyme relating to synthesis of an intracellular sugar nucleotide, GDP-fucose, or an enzyme relating to the modification of a sugar chain in which 1-position of fucose is bound to 6-position of N-acetylglucosamine in the reducing end through α-bond in a complex type N-glycoside-linked sugar chain have been knocked out.

(5) The process according to (3) or (4), wherein the enzyme relating to the synthesis of an intracellular sugar nucleotide, GDP-fucose is an enzyme selected from the group consisting of GDP-mannose 4,6-dehydratase (GMD) and GDP-4-keto-6-deoxy-D-mannose-3,5-epimerase (Fx).

(6) The process according to (5), wherein the GDP-mannose 4,6-dehydratase is a protein encoded by a DNA selected from the group consisting of the following (a) and (b):

(a) a DNA comprising the nucleotide sequence represented by SEQ ID NO:7;

(b) a DNA which hybridizes with the DNA consisting of the nucleotide sequence represented by SEQ ID NO:7 under stringent conditions and which encodes a protein having GDP-mannose 4,6-dehydratase activity.

(7) The process according to (5), wherein the GDP-mannose 4,6-dehydratase is a protein selected from the group consisting of (a), (b) and (c):

(a) a protein comprising the amino acid sequence represented by SEQ ID NO:8;

(b) a protein consisting of an amino acid sequence in which one or more amino acid residue(s) are deleted, substituted, inserted and/or added in the amino acid sequence represented by SEQ ID NO:8 and having GDP-mannose 4,6-dehydratase activity;

(c) a protein consisting of an amino acid sequence which has 80% or more homology to the amino acid sequence represented by SEQ ID NO:8 and having GDP-mannose 4,6-dehydratase activity.

(8) The process according to (5), wherein the GDP-4-keto-6deoxy-D-mannose-3,5-epimerase is a protein encoding a DNA selected from the group consisting of the following (a) and (b);

(a) a DNA comprising the nucleotide sequence represented by SEQ ID NO:9;

(b) a DNA which hybridizes with the DNA consisting of the nucleotide sequence represented by SEQ ED NO:9 under stringent conditions and which encodes a protein having GDP-4-keto-6-deoxy-D-mannose-3,5-epimerase activity.

(9) The process according to (5), wherein the GDP-4-keto-6-deoxy-D-mannose-3,5-epimerase is a protein selected from the group consisting of (a), (b) and (c);

(a) a protein comprising the amino acid sequence represented by SEQ ID NO:10;

(b) a protein consisting of an amino acid sequence in which one or more amino acid residue(s) are deleted, substituted, inserted and/or added in the amino acid sequence represented by SEQ ID NO:10 and having GDP-4-keto-6-deoxy-D-mannose-3,5-epimerase activity;

(c) a protein consisting of an amino acid sequence which has 80% or more homology to the amino acid sequence represented by SEQ ID NO:10 and having GDP-4-keto-6-deoxy-D-mannose-3,5-epimerase activity.
(10) The process according to (3) or (4), wherein the enzyme relating to the modification of a sugar chain in which 1-position of fucose is bound to 6-position of N-acetylglucosamine in the reducing end through α-bond in a complex type N-glycoside-linked sugar chain is α1,6-fucosyltransferase.
(11) The process according to (10), wherein the α1,6-fucosyltransferase is a protein encoded by a DNA selected from the group consisting of the following (a) to (d):
(a) a DNA comprising the nucleotide sequence represented by SEQ ID NO:11;
(b) a DNA comprising the nucleotide sequence represented by SEQ ID NO:12;
(c) a DNA which hybridizes with a DNA consisting of the nucleotide sequence represented by SEQ ID NO:11 under stringent conditions and which encodes a protein having α1,6-fucosyltransferase activity;
(d) a DNA which hybridizes with a DNA consisting of the nucleotide sequence represented by SEQ ID NO:12 under stringent conditions and which encodes a protein having α1,6-fucosyltransferase activity.
(12) The process according to (10), wherein the α1,6-fucosyltransferase is a protein selected from the group consisting of the following (a) to (f):
(a) a protein comprising the amino acid sequence represented by SEQ ID NO:13;
(b) a protein comprising the amino acid sequence represented by SEQ ID NO:14;
(c) a protein consisting of an amino acid sequence in which one or more amino acid residue(s) are deleted, substituted, inserted and/or added in the amino acid sequence represented by SEQ ID NO:13 and having α1,6-fucosyltransferase activity;
(d) a protein consisting of an amino acid sequence in which one or more amino acid residue(s) are deleted, substituted, inserted and/or added in the amino acid sequence represented by SEQ ID NO:14 and having α1,6-fucosyltransferase activity;
(e) a protein consisting of an amino acid sequence having a homology of 80% or more with the amino acid sequence represented by SEQ ID NO:13 and having α1,6-fucosyltransferase activity;
(f) a protein consisting of an amino acid sequence having a homology of 80% or more with the amino acid sequence represented by SEQ ID NO:14 and having α1,6-fucosyltransferase activity.
(13) The process according to any one of (1) to (4), wherein the transformant is FERM BP-08472, FERM BP-10083, FERM BP-10084, FERM BP-10088 or FERM BP-10089.
(14) The process according to any one of (1) to (12), wherein the host cell is a cell selected from the group consisting of the following (a) to (j):
(a) a CHO cell derived from a Chinese hamster ovary tissue;
(b) a rat myeloma cell line YB2/3HL.P2.G11.16Ag.20 cell;
(c) a mouse myeloma cell line NS0 cell;
(d) a mouse myeloma cell line SP2/0-Ag14 cell;
(e) a BHK cell derived from a Syrian hamster kidney tissue;
(f) a human leukemic cell line Namalwa cell;
(g) an embryonic stem cell;
(h) a fertilized egg cell;
(i) a plant cell;
(j) yeast.
(15) The process according to any one of (1) to (14), wherein the antithrombin III composition has complex type N-glycoside-linked sugar chains, and the complex type N-glycoside-linked sugar chains have a structure in which fucose is not bound to N-acetylglucosamine in the reducing end in the sugar chains.
(16) The process according to any one of (1) to (15), wherein the complex type N-glycoside-linked sugar chains have a structure in which 1-position of fucose is not bound to 6-position of N-acetylglucosamine in the reducing end in the sugar chains.
(17) The process according to any one of (1) to (16), wherein the antithrombin III is a polypeptide comprising the amino acid sequence represented by SEQ ID NO:4.
(18) The process according to any one of (1) to (17), wherein the antithrombin III is a polypeptide consisting of an amino acid sequence in which one or more amino acid residue(s) are deleted, substituted, inserted and/or added in the amino acid sequence represented by SEQ ID NO:4 and having heparin binding activity.
(19) The process according to any one of (1) to (18), wherein the antithrombin III is a polypeptide consisting of an amino acid sequence which has 80% or more homology to the amino acid sequence represented by SEQ ID NO:4 and having heparin binding activity.
(20) The process according to any one of (1) to (19), wherein the antithrombin III is a polypeptide encoded by a DNA selected from the group consisting of the following (a) and (b):
(a) a DNA comprising the nucleotide sequence represented by SEQ ID NO:1;
(b) a DNA which hybridizes with the DNA consisting of the nucleotide sequence represented by SEQ ID NO:1 under stringent conditions and which encodes a protein having heparin binding activity.
(21) The process according to any one of (1) to (20), wherein the antithrombin III is derived from a mammal.
(22) An antithrombin III composition which is obtained by the process according to any one of (1) to (21).
(23) A medicament which comprises the antithrombin III composition according to (22) as an active ingredient.
(24) The medicament according to (23), which is an agent for diagnosing, preventing or treating diseases accompanied with blood coagulation.

DETAILED DESCRIPTION OF THE INVENTION

Figure 1:
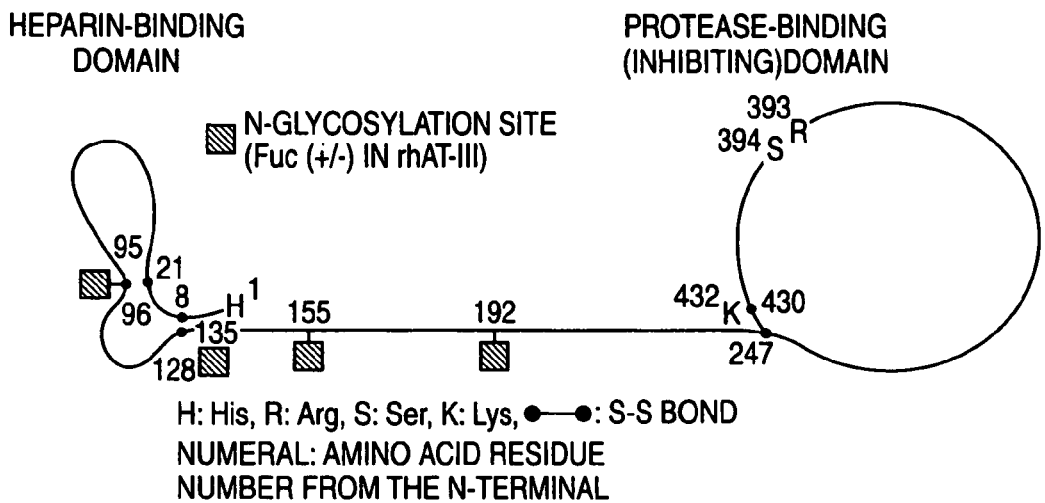
FIG. 1 schematically shows a structure of human antithrombin III.

The present invention relates to a process for producing an antithrombin III composition comprising a gene-recombinant antithrombin III molecule having complex type N-glycoside-linked sugar chains, wherein the complex type N-glycoside-linked sugar chains have a structure in which fucose is not bound to N-acetylglucosamine in the reducing end in the sugar chains, and a medicament comprising the antithrombin III composition.

In the present invention, the antithrombin III includes a protein encoded by a DNA of the following (a), (b), (c), (d), (e) or (f), a protein of the following (g), (h), (i), (j), (k), (l) or (o), and the like:

(a) a DNA comprising the nucleotide sequence represented by SEQ ID NO:1;
(b) a DNA comprising the nucleotide sequence represented by SEQ ID NO:2;
(c) a DNA comprising the nucleotide sequence represented by SEQ ID NO:3;
(d) a DNA which hybridizes with the DNA consisting of the nucleotide sequence represented by SEQ ID NO:1 under stringent conditions and which encodes a protein having heparin binding activity;
(e) a DNA which hybridizes with the DNA consisting of the nucleotide sequence represented by SEQ ID NO:2 under stringent conditions and which encodes a protein having heparin binding activity;
(f) a DNA which hybridizes with the DNA consisting of the nucleotide sequence represented by SEQ ID NO:3 under stringent conditions and which encodes a protein having heparin binding activity;
(g) a protein comprising the amino acid sequence represented by SEQ ID NO:4;
(h) a protein comprising the amino acid sequence represented by SEQ ID NO:5;
(i) a protein comprising the amino acid sequence represented by SEQ ID NO:6;
(j) a protein consisting of an amino acid sequence in which one or more amino acid residue(s) are deleted, substituted, inserted and/or added in the amino acid sequence represented by SEQ ID NO:4 and having heparin binding activity;
(k) a protein consisting of an amino acid sequence in which one or more amino acid residue(s) are deleted, substituted, inserted and/or added in the amino acid sequence represented by SEQ ID NO:5 and having heparin binding activity;
(l) a protein consisting of an amino acid sequence in which one or more amino acid residue(s) are deleted, substituted, inserted and/or added in the amino acid sequence represented by SEQ ID NO:6 and having heparin binding activity;
(m) a protein consisting of an amino acid sequence which has 80% or more homology to the amino acid sequence represented by SEQ ID NO:4 and having heparin binding activity;
(n) a protein consisting of an amino acid sequence which has 80% or more homology to the amino acid sequence represented by SEQ ID NO:5 and having heparin binding activity;
(o) a protein consisting of an amino acid sequence which has 80% or more homology to the amino acid sequence represented by SEQ ID NO:6 and having heparin binding activity.

Also, the DNA encoding the amino acid sequence of the antithrombin III includes a DNA comprising the nucleotide sequence represented by SEQ ID NO:1, 2 or 3, a DNA which hybridizes with the DNA consisting of the nucleotide sequence represented by SEQ ID NO:1, 2 or 3 under stringent conditions and which encodes a protein having heparin binding activity.

In the present invention, the DNA which hybridizes under stringent conditions refers to a DNA which is obtained by colony hybridization, plaque hybridization, Southern hybridization or the like using, for example, a DNA comprising the nucleotide sequence represented by SEQ ID NO:1, 2 or 3 or a fragment thereof as a probe. A specific example of such DNA is a DNA which can be identified by performing hybridization at 65° C. in the presence of 0.7 to 1.0 M sodium chloride using a filter with colony- or plaque-derived DNA immobilized thereon, and then washing the filter at 65° C. with a 0.1 to 2-fold concentration SSC solution (1-fold concentration SSC solution: 150 mM sodium chloride and 15 mM sodium citrate). Hybridization can be carried out according to the methods described in *Molecular Cloning, A Laboratory Manual*, Second Edition, Cold Spring Harbor Laboratory Press (1989) (hereinafter referred to as *Molecular Cloning*, Second Edition); *Current Protocols in Molecular Biology*, John Wiley & Sons (1987-1997) (hereinafter referred to as *Current Protocols in Molecular Biology*); *DNA Cloning 1: Core Techniques, A Practical Approach,* Second Edition, Oxford University (1995), etc. Specifically, the DNA capable of hybridization under stringent conditions includes DNA having at least 60% or more homology, preferably 70% or more hornology, more preferably 80% or more homology, further preferably 90% or more homology, particularly preferably 95% or more homology, most preferably 98% or more homology to the nucleotide sequence represented by SEQ ID NO:1, 2 or 3.

In the present invention, the protein consisting of an amino acid sequence wherein one or more amino acid residue(s) are deleted, substituted, inserted and/or added in the amino acid sequence represented by SEQ ID NO:4, 5 or 6 and having activity substantially similar to heparin binding activity is a protein which can be obtained, for example, by introducing a site-directed mutation into a DNA encoding a protein consisting of the amino acid sequence represented by SEQ ID NO:4, 5 or 6 by site-directed mutagenesis described in *Molecular Cloning*, Second Edition; *Current Protocols in Molecular Biology; Nucleic Acids Research,* 10, 6487 (1982); *Proc. Natl. Acad. Sci., USA,* 79, 6409 (1982); *Gene,* 34, 315 (1985); *Nucleic Acids Research,* 13, 4431 (1985); *Proc. Nat. Acad. Sci. USA,* 82, 488 (1985), etc. The number of amino acid residues which are deleted, substituted, inserted and/or added is one or more, and is not specifically limited, but it is within the range where deletion, substitution or addition is possible by known methods such as the above site-directed mutagenesis. The suitable number is 1 to dozens, preferably 1 to 20, more preferably 1 to 10, further preferably 1 to 5.

The protein consisting of an amino acid sequence which has 80% or more homology to the amino acid sequence represented by SEQ ID NO:4, 5 or 6 and having activity substantially similar to heparin binding activity includes a protein having at least 80% or more homology, preferably 85% or more homology, more preferably 90% or more homology, further preferably 95% or more homology, particularly preferably 97% or more homology, most preferably 99% or more homology to the protein consisting of the amino acid sequence represented by SEQ ID NO:4, 5 or 6, respectively, calculated by using analysis software such as BLAST [*J. Mol. Biol.,* 215, 403 (1990)] or FASTA [*Methods in Enzymology,* 183 63 (1990)].

In the present invention, the sugar chains in which fucose is not bound to the N-acetylglucosamine in the reducing end in the complex type N-glycoside-linked sugar chains as used herein means sugar chains in which fucose is not substantially bound to the N-acetylglucosamine in the reducing end in the complex type N-glycoside-linked sugar chains, preferably sugar chains in which the content ratio of fucose bound to the N-glycoside-linked sugar chains in the reducing end in the complex type N-glycoside-linked sugar chains is 0%. The antithrombin III composition of the present invention specifically refers to a composition in which fucose is not substantially detected when subjected to the sugar chain analysis described in 4 below, and the content of fucose which is not substantially detected means that the content of fucose is below the detection limit.

It is known that the N-glycoside-linked sugar chains bound to a glycoprotein such as antithrombin III have various structures, but have a basic common core structure shown by the following structural formula (I):

Such an antithrombin III composition includes an antithrombin III composition comprising an antithrombin III molecule having complex type N-glycoside-linked sugar chains, wherein the complex type N-glycoside-linked sugar chains have a structure in which fucose is not bound to N-acetylglucosamine in the reducing end in the sugar chains.

The sugar chain in which fucose is not bound to N-acetylglucosamine in the reducing end in the complex N-glycoside-linked sugar chain may be any sugar chain, so long as it is a sugar chain in which 1-position of fucose is not bound to 6-position of N-acetylglucosamine in the reducing end through α-bond in the complex type N-glycoside-linked sugar chain. The sugar chain structure in the non-reducing end may have diversity.

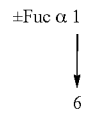
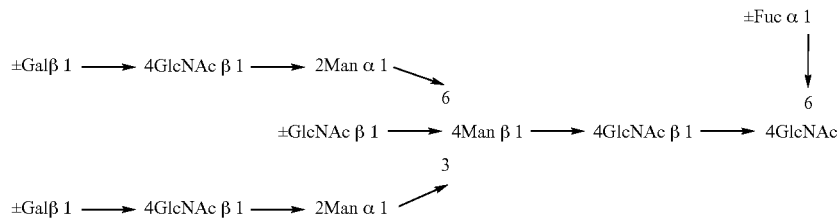

In formula (I), the sugar chain terminal which binds to asparagine is called a reducing end, and the opposite side is called a non-reducing end.

The N-glycoside-linked sugar chain includes a high mannose type in which mannose alone binds to the non-reducing end of the core structure; a complex type in which the non-reducing end of the core structure has one or plurality of parallel branches of galactose-N-acetylglucosamine (hereinafter referred to as Gal-GlcNAc) and the non-reducing end of Gal-GlcNAc has a structure of sialic acid, bisecting N-acetylglucosamine or the like, a hybrid type in which the non-reducing end of the core structure comprises branches of both of the high mannose type and complex type; and the like.

As amino acid residues to which the N-glycoside-linked sugar chain is bound in the antithrombin III molecule, there are four asparagine residues at positions 96, 135, 155 and 192 from the N-terminal. Examples include antithrombin III (α type) in which the N-glycoside-linked sugar chains are bound to all asparagine residues, and antithrombin III (β type) in which the N-glycoside-linked sugar chains are bound to the asparagine residues at positions 96, 155 and 192.

The N-glycoside-linked sugar chains bound to antithrombin III include the above-described complex type N-glycoside-linked sugar chains.

As the complex type N-glycoside-linked sugar chains bound to the antithrombin III molecule, any sugar chain comprising the core structure represented by the above-described structural formula (I). Accordingly, there are a large number of combinations in three or four N-glycoside-linked sugar chains bound to antithrombin III.

Therefore, the antithrombin III composition obtained by the process of the present invention may be a composition comprising an antithrombin III molecule having the same sugar chain structure or a composition comprising antithrombin III molecules having different sugar chain structures, so long as the composition has biological activity qualitatively similar to that of natural antithrombin III. The natural antithrombin III means antithrombin III derived from a natural material such as blood plasma.

The sugar chain structure of the composition comprising an antithrombin III molecule having complex type N-glycoside-linked sugar chains can be determined by releasing the sugar chains from the antithrombin III molecules by known methods such as hydrazinolysis and enzyme digestion [Seibutsukagaku Jikkenho (*Biochemical Experimentation Methods*) 23—Totanpakushitsu Tosa Kenkyuho (Methods of Studies on Glycoprotein Sugar Chains), Gakkai Shuppan Center, edited by Reiko Takahashi (1989)], labeling the released sugar chains with a fluorescent substance or radioisotope, and separating the labeled sugar chains by chromatography. Alternatively, the released sugar chains may be analyzed by the HPAED-PAD method [*J. Liq. Chromatogr.*, 6 1577 (1983)] to determine it.

In the process of the present invention, a host cell modified by gene recombination can be used.

The host cell modified by gene recombination means a host cell in which the property of the cell has been changed by artificial gene recombination operation. The artificial gene recombination operation includes gene disruption targeting a gene, introduction of a dominant-negative mutant of a gene encoding the enzyme, introduction of a mutation into the enzyme, and inhibition of transcription or translation of a gene encoding the enzyme. Furthermore, a method in which a gene-recombinant cell is artificially selected is also included in the artificial gene recombination operation.

The host cell in the present invention includes yeast cells, animal cells, insect cells, plant cells and the like. Examples of the cells include those described in 2 below. Specifically, preferred among animal cells are CHO cell derived from Chinese hamster ovary tissue, rat myeloma cell line YB2/3HL.P2.G11.16Ag.20, mouse myeloma cell line NS0, mouse myeloma cell line SP2/0-Ag14, BHK cell derived from Syrian hamster kidney tissue, an antibody-producing hybridoma cell, human leukemia cell line Namalwa, an embryonic stem cell, and a fertilized egg cell.

Examples of the host cell include host cells having property of the following (a) or (b):

(a) a cell in which genome is modified so as to have deleted activity of an enzyme relating to the synthesis of an intracellular sugar nucleotide, GDP-fucose;
(b) a cell in which genome is modified so as to have deleted activity of an enzyme relating to the modification of a sugar chain in which 1-position of fucose is bound to 6-position of N-acetylglucosamine in the reducing end through α-bond in a complex type N-glycoside-linked sugar chain.

Examples of the enzymes relating to the synthesis of the intracellular sugar nucleotide GDP- fucose include GDP-mannose 4,6-dehydratase (GMD) and GDP-4-keto-6-deoxy-D-mannose 3,5-epimerase (Fx).

In the present invention, examples of the GDP-mannose 4,6-dehydratase include a protein encoded by a DNA of the following (a) or (b), and a protein of the following (c), (d) or (e):
(a) a DNA comprising the nucleotide sequence represented by SEQ ID NO:7;
(b) a DNA which hybridizes with DNA consisting of the nucleotide sequence represented by SEQ ID NO:7 under stringent conditions and which encodes a protein having GDP-mannose 4,6-dehydratase activity;
(c) a protein comprising the amino acid sequence represented by SEQ ID NO:8;
(d) a protein consisting of an amino acid sequence wherein one or more amino acid residue(s) are deleted, substituted, inserted and/or added in the amino acid sequence represented by SEQ ID NO:8 and having GDP-mannose 4,6-dehydratase activity;
(e) a protein consisting of an amino acid sequence which has 80% or more homology to the amino acid sequence represented by SEQ ID NO:8 and having GDP-mannose 4,6-dehydratase activity.

In the present invention, examples of the GDP-4-keto-6-deoxy-D-mannose 3,5-epimerase include a protein encoded by a DNA of the following (a) or (b), and a protein of the following (c), (d) or (e):
(a) a DNA comprising the nucleotide sequence represented by SEQ ID NO:9;
(b) a DNA which hybridizes with DNA consisting of the nucleotide sequence represented by SEQ ID NO:9 under stringent conditions and which encodes a protein having GDP-4-keto-6-deoxy-D-mannose 3,5-epimerase activity;
(c) a protein comprising the amino acid sequence represented by SEQ ID NO:10;
(d) a protein consisting of an amino acid sequence wherein one or more amino acid residue(s) are deleted, substituted, inserted and/or added in the amino acid sequence represented by SEQ ID NO:10 and having GDP-4-keto-6-deoxy-D-mannose 3,5-epimerase activity;
(e) a protein consisting of an amino acid sequence which has 80% or more homology to the amino acid sequence represented by SEQ ID NO:10 and having GDP-4-keto-6-deoxy-D-mannose 3,5-epimerase activity.

An example of the enzyme relating to the modification of a sugar chain in which 1-position of fucose is bound to 6-position of N-acetylglucosamine in the reducing end through α-bond in a complex type N-glycoside-linked sugar chain is α1,6-fucosyltransferase.

In the present invention, examples of the α1,6-fucosyltransferase include a protein encoded by a DNA of the following (a), (b), (c) or (d), and a protein of the following (e), (f), (g), (h), (i) or (j):
(a) a DNA comprising the nucleotide sequence represented by SEQ ID NO:11;
(b) a DNA comprising the nucleotide sequence represented by SEQ ID NO 12;
(c) a DNA which hybridizes with DNA consisting of the nucleotide sequence represented by SEQ ID NO:11 under stringent conditions and which encodes a protein having α1,6-fucosyltransferase activity;
(d) a DNA which hybridizes with DNA consisting of the nucleotide sequence represented by SEQ ID NO:12 under stringent conditions and which encodes a protein having α1,6-fucosyltransferase activity;
(e) a protein comprising the amino acid sequence represented by SEQ ID NO:13;
(f) a protein comprising the amino acid sequence represented by SEQ ID NO:14;
(g) a protein consisting of an amino acid sequence wherein one or more amino acid residue(s) are deleted, substituted, inserted and/or added in the amino acid sequence represented by SEQ ID NO:13 and having α1,6-fucosyltransferase activity;
(h) a protein consisting of an amino acid sequence wherein one or more amino acid residue(s) are deleted, substituted, inserted and/or added in the amino acid sequence represented by SEQ ID NO:14 and having α1,6-fucosyltransferase activity;
(i) a protein consisting of an amino acid sequence which has 80% or more homology to the amino acid sequence represented by SEQ ID NO:13 and having α1,6-fucosyltransferase activity;
(j) a protein consisting of an amino acid sequence which has 80% or more homology to the amino acid sequence represented by SEQ ID NO:14 and having α1,6-fucosyltransferase activity.

The DNAs encoding the amino acid sequences of GDP-mannose 4,6-dehydratase include a DNA comprising the nucleotide sequence represented by SEQ ID NO:7, and a DNA which hybridizes with DNA consisting of the nucleotide sequence represented by SEQ ID NO:7 under stringent conditions and which encodes a protein having GDP-mannose 4,6-dehydratase activity.

The DNAs encoding the amino acid sequences of GDP-4-keto-6-deoxy-D-mannose 3,5-epimerase include a DNA comprising the nucleotide sequence represented by SEQ ID NO:9, and a DNA which hybridizes with DNA consisting of the nucleotide sequence represented by SEQ ID NO:9 under stringent conditions and which encodes a protein having GDP-4-keto-6-deoxy-D-mannose 3,5-epimerase activity.

The DNAs encoding the amino acid sequences of α1,6-fucosyltransferase include a DNA comprising the nucleotide sequence represented by SEQ ID NO:11 or 12, and a DNA which hybridizes with DNA consisting of the nucleotide sequence represented by SEQ ID NO:11 or 12 under stringent conditions and which encodes a protein having α1,6-fucosyltransferase activity.

In the present invention, the DNA which hybridizes under stringent conditions refers to a DNA which is obtained by colony hybridization, plaque hybridization, Southern hybridization or the like using, for example, a DNA consisting of the nucleotide sequence represented by SEQ ID NO:7, 9, 11 or 12 or a fragment thereof as a probe. A specific example of such DNA is a DNA which can be identified by performing hybridization at 65° C. in the presence of 0.7 to 1.0 M sodium chloride using a filter with colony- or plaque-derived DNA immobilized thereon, and then washing the filter at 65° C. with a 0.1 to 2-fold concentration SSC solution (1-fold concentration SSC solution: 150 mM sodium chloride and 15 mM sodium citrate). Hybridization can be carried out according to the methods described in *Molecular Cloning*, Second Edition; *Current Protocols in Molecular Biology*; *DNA Cloning 1: Core Techniques, A Practical Approach*, Second Edition, Oxford University (1995), etc. Specifically, the DNA capable of hybridization under stringent conditions includes DNA having at least 60% or more homology, preferably 70% or more homology, more preferably 80% or more homology, further preferably 90% or more homology, particularly preferably 95% or more homology, most preferably 98% or more homology to the nucleotide sequence represented by SEQ ID NO:7, 9, 11 or 12.

In the present invention, the protein consisting of an amino acid sequence wherein one or more amino acid residue(s) are deleted, substituted, inserted and/or added in the amino acid sequence represented by SEQ ID NO:8 and having GDP-mannose 4,6-dehydratase activity, the protein consisting of an amino acid sequence wherein one or more amino acid residue(s) are deleted, substituted, inserted and/or added in the amino acid sequence represented by SEQ ID NO:10 and having GDP-4-keto-6-deoxy-D-mannose 3,5-epimerase activity and the protein consisting of an amino acid sequence wherein one or more amino acid residue(s) are deleted, substituted, inserted and/or added in the amino acid sequence represented by SEQ ID NO:13 or 14 and having α1,6-fucosyltransferase activity can be obtained, for example, by introducing a site-directed mutation into DNA having the nucleotide sequence represented by SEQ ID NO:8, 10, 13 or 14 by site-directed mutagenesis described in *Molecular Cloning*, Second Edition; *Current Protocols in Molecular Biology, Nucleic Acids Research,* 10, 6487 (1982); *Proc. Natl. Acad. Sci. USA,* 79, 6409 (1982); *Gene,* 34, 315 (1985), *Nucleic Acids Research,* 13 4431 (1985); *Proc. Natl. Acad. Sci. USA,* 82, 488 (1985), etc. The number of amino acid residues which are deleted, substituted, inserted and/or added is one or more and is not specifically limited, but it is within the range where deletion, substitution or addition is possible by known methods such as the above site-directed mutagenesis. The suitable number is 1 to dozens, preferably 1 to 20, more preferably 1 to 10, further preferably 1 to 5.

Also, the protein consisting of an amino acid sequence which has 80% or more homology to the amino acid sequence represented by SEQ ID NO:8, 10, 13 or 14 and having GDP-mannose 4,6-dehydratase activity, GDP-4-keto-6-deoxy-D-mannose 3,5-epimerase activity or α1,6-fucosyltransferase activity includes a protein having at least 80% or more homology, preferably 85% or more homology, more preferably 90% or more homology, further preferably 95% or more homology, particularly preferably 97% or more homology, most preferably 99% or more homology to the amino acid sequence represented by SEQ ID NO:8, 10, 13 or 14, respectively, as calculated by using analysis software such as BLAST [*J. Mol. Biol.,* 215, 403 (1990)] or FASTA [*Methods in Enzymology,* 183, 63 (1990)].

Also, a transformant capable of producing the antithrombin III composition of the present invention can be obtained by introducing a DNA encoding the antithrombin III molecule into a host cell in which the above-described enzyme activity is deleted, i.e., a host cell in which genome is modified so as to have deleted activity of the enzyme relating to the synthesis of an intracellular sugar nucleotide, GDP-fucose, or the enzyme relating to modification of a sugar chain in which 1-position of fucose is bound to 6-position of N-acetylglucosamine in the reducing end through α-bond in a complex type N-glycoside-linked sugar chain.

The modification of the genome so as to have deleted activity of the enzyme relating to the synthesis of an intracellular sugar nucleotide, GDP-fucose, or the enzyme relating to modification of a sugar chain in which 1-position of fucose is bound to 6-position of N-acetylglucosamine in the reducing end through α-bond in a complex type N-glycoside-linked sugar chain refers to introduction of mutation into an expression regulation region of a gene so as to delete the expression of the enzyme or introduction of mutation in the amino acid sequence of a gene so as to delete the function of the enzyme. The "introduction of mutation" refers to carrying out modification of the nucleotide sequence on the genome such as deletion, substitution, insertion and/or addition in the nucleotide sequence. Complete inhibition of the expression or function of the thus modified genomic gene refers to "knock out of the genomic gene" Examples of the knocked out genomic gene include all or a part of the target gene is deleted from the genome. The knocked out conditions can be obtained by deleting the gnomic region of an exon containing an initiation codon of the target gene from the chromosome.

As the method for obtaining such cells, any technique can be used, so long as the genome of interest can be modified. For example, the following techniques can be employed for deleting the above enzyme activity (a) gene disruption targeting at a gene encoding the enzyme;
(b) introduction of a dominant-negative mutant of a gene encoding the enzyme;
(c) introduction of a mutation into the enzyme;
(d) inhibition of transcription or translation of a gene encoding the enzyme;
(e) selection of a cell line resistant to a lectin which recognizes a sugar chain structure in which 1-position of fucose is bound to 6-position of N-acetylglucosamine in the reducing end through α-bond in a complex type N-glycoside-linked sugar chain.

As the lectin which recognizes a sugar chain structure in which 1-position of fucose is bound to 6-position of N-acetylglucosamine in the reducing end through α-bond in a complex type N-glycoside-linked sugar chain, any lectin can be used, so long as it is capable of recognizing the sugar chain structure. Specific examples include lentil lectin LCA (lentil agglutinin derived from *Lens culinaris*), pea lectin PSA (pea lectin derived from *Pisum sativum*), broad bean lectin VFA (agglutinin derived from *Vicia faba*) and *Aleuria aurantia* lectin AAL (lectin derived from *Aleuria aurantia*).

The "cell resistant to a lectin" refers to a cell in which growth is not inhibited by the presence of a lectin at an effective concentration. The "effective concentration" is a concentration higher than the concentration that does not allow the normal growth of a cell prior to the genome modification (hereinafter referred to also as parent cell line), preferably equal to the concentration that does not allow the normal growth of a cell prior to the genome modification, more preferably 2 to 5 times, further preferably 10 times, most preferably 20 or more times the concentration that does not allow the normal growth of a cell prior to the modification of the genomic gene.

In the present invention, the effective concentration of lectin that does not inhibit growth may be appropriately determined according to each cell line. It is usually 10 µg/ml to 10 mg/ml, preferably 0.5 mg/ml to 2.0 mg/ml.

The cell prior to the modification of the genomic gene, i.e., the parent cell, includes a cell prior to the application of the technique for the modification of the genomic gene encoding the enzyme relating to the synthesis of an intracellular sugar nucleotide, GDP-fucose, or the enzyme relating to modification of a sugar chain in which 1-position of fucose is bound to 6-position of N-acetylglucosamine in the reducing end through α-bond in a complex type N-glycoside-linked sugar chain. The cell prior to the modification of the genomic gene is not particularly limited, and includes the following cells as preferred examples.

The parent cell of NS0 cell prior to the modification of the genomic gene includes NS0 cells described in literatures such as *BIO/TECHNOLOGY*, 10, 169 (1992) and *Biotechnol. Bioeng.*, 7, 261 (2001). Furthermore, it includes NS0 cell line (RCB 0213) registered at RIKEN Cell Bank, The Institute of Physical and Chemical Research, sub-cell lines obtained by naturalizing these cell lines to various serum free media, and the like.

The parent cell of SP2/0-Ag14 cell prior to the modification of the genomic gene includes SP2/0-Ag14 cells described in literatures such as *J. Immunol.*, 126, 317 (1981), *Nature*, 276. 269 (1978) and *Human Antibodies and Hybridomas*, 3, 129 (1992). Furthermore, it includes SP2/0-Ag14 cell (ATCC CRL-1581) registered at American Type Culture Collection (hereinafter referred to as ATCC), sub-cell lines obtained by naturalizing these cell lines to various serum free media (ATCC CRL-1581.1), and the like.

The parent cell of CHO cell derived from Chinese hamster ovary tissue prior to the modification of the genomic gene includes CHO cells described in literatures such as *Journal of Experimental Medicine*, 108, 945 (1958), *Proc. Natl. Acad. Sci. USA*, 60, 1275 (1968), *Genetics*, 55, 513 (1968), *Chromosoma*, 41, 129 (1973), *Methods in Cell Science*, 18, 115 (1996), *Radiation Research*, 148, 260 (1997), *Proc. Natl. Acad. Sci. USA*, 77, 4216 (1980), *Proc. Natl. Acad. Sci. USA*, 60, 1275 (1968), *Cell*, 6, 121 (1975), *Molecular Cell Genetics*, Appendix I, II (p. 883-900) and *Somatic Cell and Molecular Genetics*, 12, 555 (1986). Furthermore, it includes cell line CHO-K1 (ATCC CCL-61), cell line CHO/dhfr (ATCC CRL-9096) and cell line Pro-5 (ATCC CRL-1781) registered at ATCC, sub-cell lines obtained by naturalizing these cell lines to various serum free media, and the like.

The parent cell of BHK cell derived from Syrian hamster kidney tissue prior to the modification of the genomic gene includes BHK cells described in literatures such as *Proc R Soc Med*, 56, 1062 (1963) and *Nature*, 203, 1355 (1964). Furthermore, it includes cell line BHK-21 (ATCC CCL-10) registered at ATCC, commercially available cell line CHO-S (Cat # 11619 of Life Technologies), sub-cell lines obtained by naturalizing these cell lines to various serum free media, and the like.

The parent cell of a rat myeloma cell line YB2/3HL.P2.G11.16Ag.20 cell prior the modification of the genomic gene includes cell lines established from Y3/Ag1.2.3 cell (ATCC CRL 1631). Specific examples include YB2/3HL.P2.G11.16Ag.20 cell described in literatures such as *J. Cell. Biol.*, 23, 576 (1982) and *Methods Enzymol.*, 73B, 1 (1981). Furthermore, it includes YB2/3HL.P2.G11.16Ag.20 cell (ATCC CRL-1662) registered at ATCC, sub-lines obtained by naturalizing these cell lines to various serum free media, and the like.

The cell for producing the antithrombin III of the present invention includes a cell line MS705 pKAN-ATIII 27 which is a transformant in which a gene encoding the antithrombin III is introduced into a CHO cell in which a gene encoding α1,6-fucosyltransferase is knocked out, a cell line pKAN-ATIII AFMS705 obtained by naturalizing, to a serum-free medium, a transformant in which a gene encoding the antithrombin ID is introduced into a CHO cell in which a gene encoding α1,6-fucosyltransferase is knocked out, a cell line pKAN-ATIII GMDKO obtained by naturalizing, to a serum free medium, a transformant in which a gene encoding the antithrombin III is introduced into a CHO cell in which a gene encoding GDP-mannose 4,6-dehydratase is knocked out, and the like.

The cell line MS705 pKAN-ATIII 27 was deposited on Sep. 9, 2003 and the cell line pKAN-ATIII AFMS705 and the cell line pKAN-ATIII GMDKO were deposited on Aug. 10, 2004 with International Patent Organism Depositary, National Institute of Advanced Industrial Science and Technology, Central 6, 1-1, Higashi 1-chome, Tsukuba-shi, Ibaraki, Japan with accession Nos. FERM BP-08472, FERM BP-10088 and FERM BP-10083, respectively.

Also, the cell capable of producing a variant wherein the amino acid sequence is represented by SEQ ID NO:4 in which asparagine at position 135 is substituted with glutamine having biological activity similar to that of the natural antithrombin III composition of the present invention (hereinafter referred to antithrombin III variant), includes a cell line pKAN-ATIIIN135QAFMS705 obtained by naturalizing, to a serum-free medium, a transformant in which a gene encoding the antithrombin III variant represented by SEQ ID NO:40 into a CHO cell in which a gene encoding α1,6-fucosyltransferase is knocked out, and a cell line pKAN-ATIII N135Q GMDKO obtained by naturalizing, to a serum-free medium, a transformant in which a gene encoding the antithrombin III variant represented by SEQ ID NO:40 into a CHO cell in which a gene encoding GDP-mannose, 4,6-dehydratase is knocked out.

The cell line pKAN-ATIII N135Q AFMS705 and the cell line KAN-ATIII N135Q GMDKO were deposited on Aug. 10, 2004 with International Patent Organism Depositary, National Institute of Advanced Industrial Science and Technology, Central 6, 1-1, Higashi 1-chome, Tsukuba-shi, Ibaraki, Japan with accession Nos. FERM BP-10089 and FERM BP-10084, respectively.

The antithrombin III composition having biological activity similar to the natural antithrombin III can be produced by using the above transformant.

The fucose which is not bound to the N-acetylglucosamine in the reducing end in the complex type N-glycoside-linked sugar chains in the antithrombin III composition means that fucose is not substantially detected when subjected to the sugar chain analysis described below. The content of fucose which is not substantially detected means that the content of fucose is below the detection limit.

The biological activity of the antithrombin III includes binding activity to heparin, anti-blood coagulation activity and the like.

The binding activity to heparin and the anti-blood coagulation activity of the antithrombin III composition can be measured by an in vitro test such as known antithrombin activity measuring method or heparin coactor activity measuring method, an in vivo test using a model animal for disseminated intravascular coagulation syndrome, or the like (*The Second Series of Pharmaceutical Research and Development*, Volume 20, Blood Product, Ikuo Suzuld, ed., Hirokawa Publishing Company, Tokyo, Japan (1992), *The Course of Medicine* (*Igaku no Ayumi*), 120, 1147 (1982); *Japanese Pharmacology and Therapeutics*, 17, 5843 (1989); *Clinic and Research* (Rinsyo to Kenkyu), 62, 3573 (1985); *Clinic and Research* (Rinsyo to Kenkyu), 62, 3688, 1985; *Parmacometrics*, 30, 589, (1985).

The process of the antithrombin III composition of the present invention is explained in detail below.

1. Preparation of a Host Cell Producing the Antithrombin III Composition

The host cell used for producing the antithrombin III composition can be prepared by the following methods.

(1) Gene Disruption Targeting at a Gene Encoding an Enzyme

The host cell used for the preparation of the antithrombin III composition can be prepared by a gene disruption technique targeting a gene encoding an enzyme relating to the synthesis of an intracellular sugar nucleotide, GDP-fucose or an enzyme relating to the modification of a sugar chain in which 1-position of fucose is bound to 6-position of N-acetylglucosamine in the reducing end through α-bond in a complex type N-glycoside-linked sugar chain (hereinafter referred to as enzymes relating to the fucose modification). Examples of the enzymes relating to the synthesis of an intracellular sugar nucleotide, GDP-fucose include GDP-mannose 4,6-dehydratase (hereinafter referred to as GMD) and GDP-4-keto-6-deoxy-D-mannose 3,5-epimerase (hereinafter referred to as Fx). Examples of the enzymes relating to the modification of a sugar chain in which 1-position of fucose is bound to 6-position of N-acetylglucosamine in the reducing end through α-bond in a complex type N-glycoside-linked sugar chain include α1,6-fucosyltransferase and α-L-fucosidase.

The gene as used herein includes DNA and RNA.

The method of gene disruption may be any method capable of disrupting the target gene encoding the enzyme. Useful methods include the antisense method, the ribozyme method, the homologous recombination method, the RNA-DNA oligonucleotide method (hereinafter referred to as the RDO method), the RNA interference method (hereinafter referred to as the RNAi method), the method using a retrovirus and the method using a transposon. These methods are specifically described below.

(a) Preparation of the Host Cell for the Production of the Antithrombin III Composition of the Present Invention by the Antisense Method or the Ribozyme Method The host cell used for the preparation of the antithrombin III composition can be prepared by the antisense method or the ribozyme method described in *Cell Technology*, 12, 239 (1993), *BIO/TECHNOLOGY*, 17, 1097 (1999); *Hum. Mol. Genet.*, 5, 1083 (1995); *Cell Technology*, 13, 255 (1994), *Proc. Natl. Acad. Sci. U.S.A.*, 96, 1886 (1999), etc. targeting at a gene encoding the enzymes relating to the fucose modification; for example, in the following manner.

A cDNA or a genomic DNA encoding the enzymes relating to the fucose modification is prepared.

The nucleotide sequence of the prepared cDNA or genomic DNA is determined.

Based on the determined DNA sequence, an antisense gene or a ribozyme of appropriate length is designed which comprises a DNA fragment encoding the enzymes relating to the fucose modification, non-translated regions and introns.

In order to express the antisense gene or ribozyme in a cell, a recombinant vector is prepared by inserting a fragment or full-length of the prepared DNA into a site downstream of a promoter in an appropriate expression vector.

The recombinant vector is introduced into a host cell suitable for the expression vector to obtain a transformant.

The host cell used for the production of the antithrombin III composition of the present invention can be obtained by selecting a transformant using, as a marker, the activity of the enzymes relating to the fucose modification. The host cell used for the production of the antithrombin III composition of the present invention can also be obtained by selecting a transformant using, as a marker, the sugar chain structure of a glycoprotein on the cell membrane or the sugar chain structure of the produced glycoprotein molecule.

As the host cell used for the production of the antithrombin III composition of the present invention, any yeast cell, animal cell, insect cell, plant cell, or the like can be used so long as it has a target gene encoding the enzymes relating to the fucose modification. Examples of the host cells include those described in 2 below.

The expression vectors that can be employed are those capable of autonomous replication or integration into the chromosome in the above host cells and comprising a promoter at a position appropriate for the transcription of the designed antisense gene or ribozyme. Examples of the expression vectors include those described in 2 below.

Introduction of a gene into various host cells can be carried out by the methods suitable for introducing a recombinant vector into various host cells described in 2 below.

Selection of a transformant using, as a marker, the activity of the enzymes relating to the fucose modification can be carried out, for example, by the following methods.

Methods for Selecting a Transformant

A cell in which the activity of an enzyme relating to the synthesis of the enzymes relating to the fucose modification is deleted can be selected by determining the activity of the enzymes relating to the fucose modification using biochemical methods or genetic engineering techniques described in Shin Seikagaku Jikken Koza (*New Lectures on Experiments in Biochemistry*) 3—*Saccharides I, Glycoprotein* (Tokyo Kagaku Dojin), edited by The Japanese Biochemical Society (1988); *Cell Technology, Extra Edition. Experimental Protocol Series, Glycobiology Experimental Protocol, Glycoprotein, Glycolipid and Proteoglycan* (Shujunsha), edited by Naoyuki Taniguchi, Akemi Suzuki, Kiyoshi Furukawa and Kazuyuki Sugawara (1996); *Molecular Cloning*, Second Edition, *Current Protocols in Molecular Biology;* and the like. An example of the biochemical methods is a method in which the enzyme activity is evaluated using an enzyme-specific substrate. Examples of the genetic engineering techniques include Northern analysis and RT-PCR in which the amount of mRNA for a gene encoding the enzyme is measured.

Selection of a transformant using, as a marker, the sugar chain structure of a glycoprotein on the cell membrane can be carried out, for example, by the method described in 1(5) below. Selection of a transformant using, as a marker, the sugar chain structure of a produced glycoprotein molecule can be carried out, for example, by the methods described in 4 and 5 below.

Preparation of a cDNA encoding the enzymes relating to the fucose modification can be carried out, for example, by the following method.

Preparation of cDNA

Total RNA or mRNA is prepared from various host cell tissue or cell.

A cDNA library is prepared from the total RNA or mRNA.

Degenerative primers are prepared based on the amino acid sequence of the enzymes relating to the fucose modification, and a gene fragment encoding the enzymes relating to the fucose modification is obtained by PCR using the prepared cDNA library as a template.

A cDNA encoding the enzymes relating to the fucose modification can be obtained by screening the cDNA library using the obtained gene fragment as a probe.

As the mRNA of a human or non-human animal tissue or cell, commercially available mRNA (for example, manufactured by Clontech) may be use, or it may be prepared from a human or non-human animal tissue or cell in the following manner.

The methods for preparing total RNA from a human or non-human animal tissue or cell include the guanidine thiocyanate-cesium trifluoroacetate method [*Methods in Enzymology*, 154, 3 (1987)], the acidic guanidine thiocyanate-phenol-chloroform (AGPC) method [*Analytical Biochemistry*, 162, 156 (1987); *Experimental Medicine*, 9, 1937 (1991)] and the like.

The methods for preparing mRNA as poly(A)+RNA from the total RNA include the oligo (dT) immobilized cellulose column method (*Molecular Cloning*, Second Edition).

It is also possible to prepare mRNA by using a commercially available kit such as Fast Track mRNA Isolation Kit (manufactured by Invitrogen) or Quick Prep mRNA Purification Kit (manufactured by Pharmacia).

A cDNA library is prepared from the obtained mRNA of a human or non-human animal tissue or cell. The methods for preparing the cDNA library include the methods described in *Molecular Cloning*, Second Edition; *Current Protocols in Molecular Biology; A Laboratory Manual*, 2nd Ed. (1989), etc., and methods using commercially available kits such as SuperScript Plasmid System for cDNA Synthesis and Plasmid Cloning (manufactured by Life Technologies) and ZAP-cDNA Synthesis Kit (manufactured by STRATAGENE).

As the cloning vector for preparing the cDNA library, any vectors, e.g. phage vectors and plasmid vectors, can be used so long as they are autonomously replicable in *Escherichia coli* K2. Examples of suitable vectors include ZAP Express [manufactured by STRATAGENE; *Strategies*, 1, 58 (1992)], pBluescript II SK(+) [*Nucleic Acids Research*, 12, 9494 (1989)], λZAP II (manufactured by STRATAGENE), λgt10, πgt11 [*DNA Cloning, A Practical Approach*, 1, 49 (1985)], λTriplEx (manufactured by Clontech), λExCell (manufactured by Pharmacia), pT7T318U (manufactured by Pharmacia), pcD2 [*Mol. Cell. Biol.*, 3, 280 (1983)) and pUC18 [*Gene*, 33, 103 (1985)].

Any microorganism can be used as the host microorganism for preparing the cDNA library, but *Escherichia coli* is preferably used. Examples of suitable host microorganisms are *Escherichia coli* XL1-Blue MRF' [manufactured by STRATAGENE; *Strategies*, 5, 81 (1992)], *Escherichia coli* C600 [*Genetics*, 12, 440 (1954)], *Escherichia coli* Y1088 [*Science*, 222, 778 (1983)], *Escherichia coli* Y1090 [*Science*, 222 778 (1983)], *Escherichia coli* NM522 [*J. Mol. Biol.*, 166, 1 (1983)], *Escherichia coli* K802 [*J. Mol. Biol.*, 16, 118 (1966)] and *Escherichia coli* JM105 [*Gene*, 38, 275 (1985)).

The cDNA library may be used as such in the following analysis. Alternatively, in order to efficiently obtain full-length cDNAs by decreasing the ratio of partial cDNAs, a cDNA library prepared using the oligo-cap method developed by Sugano, et al. [*Gene*, 138, 171 (1994); *Gene*, 200, 149 (1997), *Protein, Nucleic Acid and Enzyme*, 41, 603 (1996); *Experimental Medicine*, 11, 2491 (1993); *cDNA Cloning* (Yodosha) (1996); *Methods for Preparing Gene Libraries* (Yodosha) (1994)] may be used in the following analysis.

A gene fragment encoding the enzymes relating to the fucose modification can be obtained by preparing degenerative primers specific for the nucleotide sequences of the 5'-terminal and 3'-terminal which are presumed to encode the amino acid sequence of the enzyme relating to the fucose modification and amplifying DNA by PCR [*PCR Protocols*, Academic Press (1990)] using the prepared cDNA library as a template.

It can be confirmed that the obtained gene fragment is a DNA encoding the enzymes relating to the fucose modification by analyzing the nucleotide sequence by generally employed methods such as the dideoxy method of Sanger, et al. [*Proc. Natl. Acad. Sci. U.S.A.*, 74, 5463 (1977)] or by use of nucleotide sequencers such as ABI PRISM 377 DNA Sequencer (manufactured by Applied Biosystems).

A DNA encoding the enzymes relating to the fucose modifications can be obtained from the cDNA or cDNA library synthesized from the mRNA contained in a human or non-human animal tissue or cell by colony hybridization or plaque hybridization (*Molecular Cloning*, Second Edition) using the above gene fragment as a probe.

A cDNA encoding the enzymes relating to the fucose modification can also be obtained by amplification by PCR using the cDNA or cDNA library synthesized from the mRNA contained in a human or non-human animal tissue or cell as a template and using the primers used for obtaining the gene fragment encoding the enzymes relating to the fucose modification.

The nucleotide sequence of the obtained DNA encoding the enzymes relating to the fucose modification can be determined by generally employed sequencing methods such as the dideoxy method of Sanger, et al. [*Proc. Natl. Acad. Sci. U.S.A.*, 74, 5463 (1977)] or by use of nucleotide sequencers such as ABI PRISM 377 DNA Sequencer (manufactured by Applied Biosystems).

By carrying out a search of nucleotide sequence databases such as GenBank, EMBL or DDBJ using a homology search program such as BLAST based on the determined nucleotide sequence of the cDNA, it can be confirmed that the obtained DNA is a gene encoding the enzymes relating to the fucose modification among the genes in the nucleotide sequence database.

Examples of the nucleotide sequences of the genes encoding the enzyme relating to the synthesis of an intracellular sugar nucleotide, GDP-fucose obtained by the above methods include the nucleotide sequences represented by SEQ ID NOs:7 and 9.

Examples of the nucleotide sequences of the genes encoding the enzyme relating to the modification of a sugar chain in which 1-position of fucose is bound to 6-position of N-acetylglucosamine in the reducing end through α-bond in a complex type N-glycoside-linked sugar chain obtained by the above methods include the nucleotide sequences represented by SEQ ID NOs:11 and 12.

The cDNA encoding the enzymes relating to the fucose modification can also be obtained by chemical synthesis with a DNA synthesizer such as DNA Synthesizer Model 392 (manufactured by Perkin Elmer) utilizing the phosphoamidite method based on the determined nucleotide sequence of the DNA.

Preparation of a genomic DNA encoding the enzymes relating to the fucose modification can be carried out, for example, by the following method.

Method for Preparing Genomic DNA

The genomic DNA can be prepared by known methods described in *Molecular Cloning*, Second Edition, *Current Protocols in Molecular Biology* etc. In addition, the genomic DNA encoding the enzymes relating to the fucose modification can be obtained by using a kit such as Genomic DNA Library Screening System (manufactured by Genome Systems) or Universal GenomeWalker™ Kits (manufactured by CLONTECH).

The nucleotide sequence of the obtained DNA encoding the enzyme relating to the fucose modification can be determined by generally employed sequencing methods such as the dideoxy method of Sanger, et al. [*Proc. Natl. Acad. Sci. U.S.A.*, 74, 5463 (1977)] or by use of nucleotide sequencers such as ABI PRISM 377 DNA Sequencer (manufactured by Applied Biosystems).

By carrying out a search of nucleotide sequence databases such as GenBank, EMBL or DDBJ using a homology search program such as BLAST based on the determined nucleotide sequence of the genomic DNA, it can be confirmed that the obtained DNA is a gene encoding the enzymes relating to the fucose modification among the genes in the nucleotide sequence database.

The genomic DNA encoding the enzymes relating to the fucose modification can also be obtained by chemical synthesis with a DNA synthesizer such as DNA Synthesizer Model 392 (manufactured by Perkin Elmer) utilizing the phosphoamidite method based on the determined nucleotide sequence of the DNA.

Examples of the nucleotide sequences of the genomic DNAs encoding the enzyme relating to the synthesis of an intracellular sugar nucleotide, GDP-fucose obtained by the above methods include the nucleotide sequences represented by SEQ ID NOs:15, 16, 17 and 18.

An example of the nucleotide sequence of the genomic DNA encoding the enzyme relating to the modification of a sugar chain in which 1-position of fucose is bound to 6-position of N-acetylglucosamine in the reducing end through α-bond in a complex type N-glycoside-linked sugar chain obtained by the above methods is the nucleotide sequence represented by SEQ ID NO:19.

The host cell used for the production of the antithrombin III composition can also be obtained without using an expression vector by directly introducing into a host cell an antisense oligonucleotide or ribozyme designed based on the nucleotide sequence encoding the enzymes relating to the fucose modification.

The antisense oligonucleotide or ribozyme can be prepared by known methods or by using a DNA synthesizer. Specifically, based on the sequence information on an oligonucleotide having a sequence corresponding to 5 to 150, preferably 5 to 60, more preferably 10 to 40 nucleotides in the nucleotide sequence of the cDNA or genomic DNA encoding the enzymes relating to the fucose modification, an oligonucleotide corresponding to the sequence complementary to the above oligonucleotide (antisense oligonucleotide) or a ribozyme comprising the oligonucleotide sequence can be synthesized.

The oligonucleotide includes oligo RNA and derivatives of the oligonucleotide (hereinafter referred to as oligonucleotide derivatives).

The oligonucleotide derivatives include an oligonucleotide derivative wherein the phosphodiester bond in the oligonucleotide is converted to a phosophorothioate bond, an oligonucleotide derivative wherein the phosphodiester bond in the oligonucleotide is converted to an N3'-P5' phosphoamidate bond, an oligonucleotide derivative wherein the ribose-phosphodiester bond in the oligonucleotide is converted to a peptide-nucleic acid bond, an oligonucleotide derivative wherein the uracil in the oligonucleotide is substituted by C-5 propynyluracil, an oligonucleotide derivative wherein the uracil in the oligonucleotide is substituted by C-5 thiazolyluracil, an oligonucleotide derivative wherein the cytosine in the oligonucleotide is substituted by C-5 propynylcytosine, an oligonucleotide derivative wherein the cytosine in the oligonucleotide is substituted by phenoxazine-modified cytosine, an oligonucleotide derivative wherein the ribose in the oligonucleotide is substituted by 2'-O-propylribose, and an oligonucleotide derivative wherein the ribose in the oligonucleotide is substituted by 2'-methoxyethoxyribose [*Cell Technology*, 16, 1463 (1997)].

(b) Preparation of the Host Cell for the Production of the Antithrombin III Composition by the Homologous Recombination Method The host cell used for the production of the antithrombin III composition can be prepared by modifying a target gene encoding the enzymes relating to the fucose modification on the chromosome using the homologous recombination method.

Modification of the target gene on the chromosome can be carried out by using the methods described in *Manipulating the Mouse Embryo, A Laboratory Manual*, Second Edition, Cold Spring Harbor Laboratory Press (1994) (hereinafter referred to as *Manipulating the Mouse Embryo, A Laboratory Manual*); *Gene Targeting, A Practical Approach*, IRL Press at Oxford University Press (1993); *Biomanual Series* 8, *Gene Targeting, Preparation of Mutant Mice Using ES Cells*, Yodosha (1995) (hereinafter referred to as *Preparation of Mutant Mice Using ES Cells*); etc., for example, in the following manner.

A genomic DNA encoding the enzymes relating to the fucose modification is prepared.

Based on the nucleotide sequence of the genomic DNA, a target vector is prepared for homologous recombination of a target gene to be modified (e.g., the structural gene or promoter gene for the enzymes relating to the fucose modification).

The host cell used for the production of the antithrombin III composition can be prepared by introducing the prepared target vector into a host cell and selecting a cell in which homologous recombination generated between the target gene on the chromosome and the target vector.

As the host cell, any yeast cell, animal cell, insect cell, plant cell, or the like can be used so long as it has a target gene encoding the enzymes relating to the fucose modification. Examples of the host cells include those described in 2 below.

The genomic DNA encoding the enzymes relating to the fucose modification can be prepared by the methods for preparing a genomic DNA described in the above 1 (1) (a) or the like.

Examples of the nucleotide sequences of the genomic DNAs encoding the enzyme relating to the synthesis of the intracellular sugar nucleotide GDP-fucose obtained by the above methods include the nucleotide sequences represented by SEQ ID NOs:15, 16, 17 and 18.

An example of the nucleotide sequence of the genomic DNA encoding the enzyme relating to the modification of a sugar chain in which 1-position of fucose is bound to 6-position of N-acetylglucosamine in the reducing end through α-bond in a complex type N-glycoside-linked sugar chain obtained by the above methods is the nucleotide sequence represented by SEQ ID NO:19.

The target vector for use in the homologous recombination of the target gene on the chromosome can be prepared according to the methods described in *Gene Targeting, A Practical Approach*, IRL Press at Oxford University Press (1993); *Biomanual Series* 8, *Gene Targeting, Preparation of Mutant Mice Using ES Cells;* etc. As the target vector, either a replacement-type one or an insertion-type one can be used.

Introduction of the target vector into various host cells can be carried out by the methods suitable for introducing a recombinant vector into various host cells described in 2 below.

The methods for efficiently selecting a homologous recombinant include positive selection, promoter selection, negative selection and polyA selection described in *Gene Targeting, A Practical Approach*, IRL Press at Oxford University Press (1993); *Preparation of Mutant Mice Using ES Cells*, etc. The methods for selecting the desired homologous recombinant from the selected cell lines include Southern hybridization (*Molecular Cloning*, Second Edition) and PCR [*PCR Protocols*, Academic Press (1990)] with the genomic DNA.

(c) Preparation of the Host Cell for the Production of the Antithrombin III Composition by the RDO Method The host cell used for the production of the antithrombin III composition can be prepared by the RDO method targeting a gene encoding the enzymes relating to the fucose modification, for example, in the following manner.

A cDNA or a genomic DNA encoding the enzyme relating to the fucose modification is prepared by the methods described in the above 1 (1) (a).

The nucleotide sequence of the prepared cDNA or genomic DNA is determined.

Based on the determined DNA sequence, an RDO construct of appropriate length which comprises a DNA encoding the enzymes relating to the fucose modification, non-translated regions and introns is designed and synthesized.

The host cell used for the production of the antithrombin III composition can be obtained by introducing the synthesized RDO into a host cell and then selecting a transformant in which a mutation occurred in the target enzyme, that is, the enzymes relating to the fucose modification.

As the host cell, any yeast cell, animal cell, insect cell, plant cell, or the like can be used so long as it has a target gene encoding the enzymes relating to the fucose modification. Examples of the host cells include those described in 2 below.

Introduction of the RDO into various host cells can be carried out by the methods suitable for introducing a recombinant vector into various host cells described in 2 below.

The cDNA encoding the enzymes relating to the fucose modification can be prepared by the methods for preparing a cDNA described in the above 1 (1) (a), or the like.

The genomic DNA encoding the enzymes relating to the fucose modification can be prepared by the methods for preparing a genomic DNA described in the above 1 (1) (a) or the like.

After DNA is cleaved with appropriate restriction enzymes, the nucleotide sequence of the DNA can be determined by subcloning the DNA fragments into a plasmid such as pBluescript SK(−) (manufactured by Stratagene), subjecting the clones to the reaction generally used as a method for analyzing a nucleotide sequence such as the dideoxy method of Sanger et al. (*Proc. Natl. Acad. Sci. USA*, 74, 5463 (1977)] or the like, and then analyzing the clones by using an automatic nucleotide sequence analyzer such as ABI PRISM 377 DNA Sequencer (manufactured by Applied Biosystems) or the like.

The RDO can be prepared by conventional methods or by using a DNA synthesizer.

The methods for selecting a cell in which a mutation occurred by introducing the RDO into the host cell, in the gene encoding the target enzyme, that is, the enzymes relating to the fucose modification include the methods for directly detecting mutations in chromosomal genes described in *Molecular Cloning*, Second Edition, *Current Protocols in Molecular Biology*; etc.

For the selection of the transformant, the following methods can also be employed; the method using, as a marker, the activity of the enzymes relating to the fucose modification described in the above 1 (1) (a), the method using, as a marker, the sugar chain structure of a glycoprotein on the cell membrane described in 1 (5) below, and the method using, as a marker, the sugar chain structure of a produced glycoprotein molecule described in 4 and 5 below.

The construction of RDO can be designed according to the descriptions in *Science*, 273, 1386 (1996); *Nature Medicine*, 4, 285 (1998), *Hepatology*, 25, 1462 (1997); *Gene Therapy*, 5, 1960 (1999), *J. Mol. Med.* 75 829 (1997); *Proc. Natl. Acad. Sci. USA*, 96, 8774 (1999); *Proc. Natl. Acad. Sci. USA*, 96, 8768 (1999); *Nuc. Acids Res.*, 27, 1323 (1999); *Invest. Dermatol.*, 111, 1172 (1998); *Nature Biotech.*, 16, 1343 (1998); *Nature Biotech.*, 18, 43 (2000); *Nature Biotech.*, 18, 555 (2000); etc.

(d) Preparation of the Host Cell for the Production of the Antithrombin III Composition by the RNAi Method The host cell used for the production of the antithrombin III composition can be prepared by the RNAi method targeting a gene encoding the enzymes relating to the fucose modification, for example, in the following manner.

A cDNA encoding the enzymes relating to the fucose modification is prepared by the methods described in the above 1 (1) (a).

The nucleotide sequence of the prepared cDNA is determined.

Based on the determined cDNA sequence, the construction of an RNAi gene of appropriate length is designed which comprises a DNA encoding the enzymes relating to the fucose modification, or non-translated regions.

In order to express the RNAi gene in a cell, a recombinant vector is prepared by inserting a fragment or full-length of the prepared cDNA into a site downstream of a promoter in an appropriate expression vector.

The recombinant vector is introduced into a host cell suitable for the expression vector to obtain a transformant.

The host cell used for the production of antithrombin III composition can be obtained by selecting a transformant using, as a marker, the activity of the enzymes relating to the fucose modification, or the sugar chain structure of a produced glycoprotein molecule or a glycoprotein on the cell membrane.

As the host cell, any yeast cell, animal cell, insect cell, plant cell, or the like can be used so long as it has a gene encoding the target enzymes relating to the fucose modification. Examples of the host cells include those described in 2 below.

The expression vectors capable of autonomous replication or integration into the chromosome in the above host cells and comprising a promoter at a position appropriate for the transcription of the designed RNAi gene can be used. Examples of the expression vectors include those described in 2 below.

Introduction of a gene into various host cells can be carried out by the methods suitable for introducing a recombinant vector into various host cells described in 2 below.

The methods for selecting the transformant using, as a marker, the activity of the enzymes relating to the fucose modification include the methods described in the above 1 (1) (a).

The methods for selecting the transformant using, as a marker, the sugar chain structure of a glycoprotein on the cell membrane include the method described in 1 (5). The methods for selecting the transformant using, as a marker, the sugar chain structure of a produced glycoprotein molecule include the methods described in 4 or 5 below.

The cDNA encoding the enzymes relating to the fucose modification can be prepared by the methods for preparing a cDNA described in the above 1 (1) (a) or the like.

The host cell used for the production of antithrombin III composition can also be obtained without using an expression vector by directly introducing into a host cell the siRNA (short interfering RNA) gene designed based on the nucleotide sequence encoding the enzymes relating to the fucose modification.

The siRNA gene can be prepared by known methods or by using a DNA synthesizer.

The construction of siRNA gene can be designed according to the descriptions in *Nature*, 391, 806 (1998); *Proc. Natl.*

Acad. Sci. USA, 95, 15502 (1998), Nature, 395, 854 (1998), Proc. Natl. Acad. Sci. USA, 96, 5049 (1999); Cell, 2, 1017 (1998), Proc. Natl. Acad. Sci. USA, 96, 1451 (1999); Proc. Natl. Acad. Sci. USA, 95, 13959 (1998); Nature Cell Biol., 2, 70 (2000); or the like.

(e) Preparation of the Host Cell for the Production of the Antithrombin III Composition by the Method Using a Transposon The host cell used for the production of the antithrombin III composition can be prepared by using the transposon system described in Nature Genet., 25, 35 (2000) or the like, and then selecting a mutant using, as a marker, the activity of the enzymes relating to the fucose modification, or the sugar chain structure of a produced glycoprotein molecule or a glycoprotein on the cell membrane.

The transposon system is a system for inducing a mutation by random insertion of an exogenous gene into the chromosome, wherein usually an exogenous gene inserted into a transposon is used as a vector for inducing a mutation and a transposase expression vector for randomly inserting the gene into the chromosome is introduced into the cell at the same time.

Any transposase can be used so long as it is suitable for the sequence of the transposon to be used.

As the exogenous gene, any gene can be used so long as it can induce a mutation in the DNA of a host cell.

As the host cell, any yeast cell, animal cell, insect cell, plant cell, or the like can be used so long as it has a gene encoding the target enzymes relating to the fucose modification. Examples of the host cells include those described in 2 below. Introduction of the gene into various host cells can be carried out by the methods suitable for introducing a recombinant vector into various host cells described in 2 below.

The methods for selecting the mutant using, as a marker, the activity of the enzymes relating to the fucose modification include the methods described in the above 1 (1) (a).

The methods for selecting the mutant using, as a marker, the sugar chain structure of a glycoprotein on the cell membrane include the method described in 1 (5). The methods for selecting the mutant using, as a marker, the sugar chain structure of a produced glycoprotein molecule include the methods described in 4 and 5 below.

(2) Technique of Introducing a Dominant-Negative Mutant of a Gene Encoding an Enzyme The host cell used for the production of the antithrombin III composition can be prepared by using the method of introducing a dominant-negative mutant of a target gene, i.e., a gene encoding an enzyme relating to the fucose modification. Examples of the enzymes relating to the synthesis of the intracellular sugar nucleotide GDP-fucose include GMD and Fx. Examples of the enzymes relating to the modification of a sugar chain in which 1-position of fucose is bound to 6position of N-acetylglucosamine in the reducing end through α-bond in a complex type N-glycoside-linked sugar chain include α1,6-fucosyltransferase and α-L-fucosidase.

These enzymes have substrate specificity and catalyze specific reactions. By disrupting the active center of such enzymes having substrate specificity and catalytic action, their dominant-negative mutants can be prepared. Preparation of a dominant-negative mutant is described in detail below, using for an example GMD among the target enzymes.

As a result of the analysis of the tertiary structure of GMD derived from Escherichia coli, it has been revealed that four amino acids (threonine at position 133, glutamic acid at position 135, tyrosine at position 157 and lysine at position 161) have an important function for the enzyme activity (Structure, 8, 2, 2000). That is, the mutants prepared by substituting the above four amino acids with other amino acids based on the tertiary structure information all showed significantly decreased enzyme activity. On the other hand, little change was observed in the ability of the mutants to bind to the GMD coenzyme NADP or the substrate GDP-mannose. Accordingly, a dominant-negative mutant can be prepared by substituting the four amino acids which are responsible for the enzyme activity of GMD. On the basis of the result of preparation of a dominant-negative mutant of GMD derived from Escherichia coli, dominant-negative mutants of other GMDs can be prepared by performing homology comparison and tertiary structure prediction using the amino acid sequence information. For example, in the case of GMD derived from CHO cell (SEQ ID NO:8), a dominant-negative mutant can be prepared by substituting threonine at position 155, glutamic acid at position 157, tyrosine at position 179 and lysine at position 183 with other amino acids. Preparation of such a gene carrying introduced amino acid substitutions can be carried out by site-directed mutagenesis described in Molecular Cloning, Second Edition; Current Protocols in Molecular Biology, etc.

The host cell used for the production of the antithrombin III composition can be prepared according to the method of gene introduction described in Molecular Cloning, Second Edition; Current Protocols in Molecular Biology; Manipulating the Mouse Embryo, Second Edition; etc. using a gene encoding a dominant-negative mutant of a target enzyme (hereinafter abbreviated as dominant-negative mutant gene) prepared as above, for example, in the following manner.

A dominant-negative mutant gene encoding the enzymes relating to the fucose modifications is prepared.

Based on the full-length DNA of the prepared dominant-negative mutant gene, a DNA fragment of appropriate length containing a region encoding the protein is prepared according to need.

A recombinant vector is prepared by inserting the DNA fragment or full-length DNA into a site downstream of a promoter in an appropriate expression vector.

The recombinant vector is introduced into a host cell suitable for the expression vector to obtain a transformant.

The host cell used for the production of the antithrombin III composition can be obtained by selecting a transformant using, as a marker, the activity of the enzymes relating to the fucose modification, or the sugar chain structure of a produced glycoprotein molecule or a glycoprotein on the cell membrane.

As the host cell, any yeast cell, animal cell, insect cell, plant cell, or the like can be used so long as it has a gene encoding the target enzymes relating to the fucose modification. Examples of the host cells include those described in 2 below.

The expression vectors capable of autonomous replication or integration into the chromosome in the above host cells and comprising a promoter at a position appropriate for the transcription of the DNA encoding the desired dominant-negative mutant can be used. Examples of the expression vectors include those described in 2 below.

Introduction of a gene into various host cells can be carried out by the methods suitable for introducing a recombinant vector into various host cells described in 2 below.

The methods for selecting the transformant using, as a marker, the activity of the enzymes relating to the fucose modification include the methods described in the above 1 (1) (a).

The methods for selecting the transformant using, as a marker, the sugar chain structure of a glycoprotein on the cell membrane include the method described in 1 (5) below. The methods for selecting the transformant using, as a marker, the sugar chain structure of a produced glycoprotein molecule include the methods described in 4 and 5 below.

(3) Technique of Introducing a Mutation into an Enzyme

The host cell used for the production of the antithrombin III composition can be prepared by introducing a mutation into a gene encoding the enzymes relating to the fucose modification, and then selecting a desired cell line in which the mutation generated in the enzyme.

Examples of the enzymes relating to the synthesis of the intracellular sugar nucleotide, GDP-fucose include GMD and Fx. Examples of the enzymes relating to the modification of a sugar chain in which 1-position of fucose is bound to 6-position of N-acetylglucosamine in the reducing end through α-bond in a complex type N-glycoside-linked sugar chain include α1,6-fucosyltransferase and α-L-fucosidase.

The methods for introducing a mutation into the enzymes relating to the fucose modification include: 1) a method in which a desired cell line is selected from mutants obtained by subjecting a parent cell line to mutagenesis or by spontaneous mutation using, as a marker, the activity of the enzymes relating to the fucose modification; 2) a method in which a desired cell line is selected from mutants obtained by subjecting a parent cell line to mutagenesis or by spontaneous mutation using, as a marker, the sugar chain structure of a produced glycoprotein molecule; and 3) a method in which a desired cell line is selected from mutants obtained by subjecting a parent cell line to mutagenesis or by spontaneous mutation using, as a marker, the sugar chain structure of a glycoprotein on the cell membrane.

Mutagenesis may be carried out by any method capable of inducing a point mutation, a deletion mutation or a frameshift mutation in DNA of a cell of a parent cell line.

Examples of suitable methods include treatment with ethyl nitrosourea, nitrosoguanidine, benzopyrene or an acridine dye and radiation treatment. Various alkylating agents and carcinogens can be used as mutagens. A mutagen is allowed to act on a cell by the methods described in *Soshiki Baiyo no Gijutsu* (*Tissue Culture Techniques*), Third Edition (Asakura Shoten), edited by The Japanese Tissue Culture Association (1996); *Nature Genet.*, 24, 314 (2000); or the like.

Examples of the mutants generated by spontaneous mutation include spontaneous mutants obtained by continuing subculture under usual cell culture conditions without any particular treatment for mutagenesis.

The methods for measuring the activity of the enzymes relating to the fucose modification include the methods described in the above 1 (1) (a). The methods for determining the sugar chain structure of a produced glycoprotein molecule include the methods described in 4 and 5 below. The methods for determining the sugar chain structure of a glycoprotein on the cell membrane include the method described in 1 (5).

(4) Technique of Suppressing Transcription or Translation of a Gene Encoding an Enzyme The host cell used for the production of the antithrombin III composition of the present invention can be prepared by suppressing transcription or translation of a target gene, i.e., a gene encoding the enzymes relating to the fucose modification using the antisense RNA/DNA technique [*Bioscience and Industry*, 50, 322 (1992), *Chemistry*, 46, 681 (1991), *Biotechnology*, 9, 358 (1992); *Trends in Biotechnology*, 10, 87 (1992); *Trends in Biotechnology*, 10, 152 (1992); *Cell Technology*, 16, 1463 (1997)], the triple helix technique [*Tends in Biotechnology*, 10, 132 (1992)], or the like.

Examples of the enzymes relating to the synthesis of the intracellular sugar nucleotide GDP-fucose include GMD and Fx. Examples of the enzymes relating to the modification of a sugar chain in which 1-position of fucose is bound to 6-position of N-acetylglucosamine in the reducing end through α-bond in a complex type N-glycoside-linked sugar chain include α1,6-fucosyltransferase and α-L-fucosidase.

(5) Technique of Selecting a Cell Line Resistant to a Lectin which Recognizes a Sugar Chain Structure in which 1-Position of Fucose is Bound to 6-Position of N-acetylglucosamine in the Reducing End Through α-Bond in a Complex Type N-glycoside-Linked Sugar Chain The host cell used for the production of the antithrombin III composition can be prepared by selecting a cell line resistant to a lectin which recognizes a sugar chain structure in which 1-position of fucose is bound to 6-position of N-acetylglucosamine in the reducing end through α-bond in a complex type N-glycoside-linked sugar chain.

The method of selection of a cell line resistant to a lectin which recognizes a sugar chain structure in which 1-position of fucose is bound to 6-position of N-acetylglucosamine in the reducing end through α-bond in a complex type N-glycoside-linked sugar chain can be carried out, for example, by the method using a lectin described in *Somatic Cell Mol. Genet.*, 12 51 (1986), etc.

As the lectin, any lectin can be used so long as it recognizes a sugar chain structure in which 1-position of fucose is bound to 6-position of N-acetylglucosamine in the reducing end through α-bond in a complex type N-glycoside-linked sugar chain. Specific examples include lentil lectin LCA (lentil agglutinin derived from *Lens culinaris*), pea lectin PSA (pea lectin derived from *Pisum sativum*), broad bean lectin VFA (agglutinin derived from *Vicia faba*) and *Aleuria aurantia* lectin AAL (lectin derived from *Aleuria aurantia*).

Specifically, the cell line of the present invention resistant to a lectin which recognizes a sugar chain structure in which 1-position of fucose is bound to 6-position of N-acetylglucosamine in the reducing end through α-bond in a complex type N-glycoside-linked sugar chain can be selected by culturing cells in a medium containing the above lectin at a concentration of 1 μg/ml to 1 mg/ml for one day to 2 weeks, preferably one day to one week, subculturing surviving cells or picking up a colony and transferring it into a culture vessel, and subsequently continuing the culturing using the medium containing the lectin.

2. Process for Producing the Antithrombin III Composition of the Present Invention The antithrombin III composition of the present invention can be obtained by expressing it in a host cell using the methods described in *Molecular Cloning*, Second Edition, *Current Protocols in Molecular Biology, Antibodies, A Laboratory Manual*, Cold Spring Harbor Laboratory, 1988 (hereinafter referred to as *Antibodies*), *Monoclonal Antibodies: Principles and Practice*, Third Edition, Acad. Press, 1993 (hereinafter referred to as *Monoclonal Antibodies*); *Antibody Engineering, A Practical Approach*, IRL Press at Oxford University Press, 1996 (hereinafter referred to as Antibody Engineering); etc., for example, in the following manner.

A full-length cDNA encoding an antithrombin III molecule is prepared, and a DNA fragment of appropriate length comprising a region encoding the antithrombin m molecule is prepared.

A recombinant vector is prepared by inserting the DNA fragment or full-length cDNA into a site downstream of a promoter in an appropriate expression vector.

The recombinant vector is introduced into a host cell suitable for the expression vector to obtain a transformant producing the antithrombin III molecule.

As the host cell, any yeast cells, animal cells, insect cells, plant cells, etc. that are capable of expressing the desired gene can be used.

Also useful are cells obtained by selecting cells in which the activity of an enzyme relating to the modification of an N-glycoside-linked sugar chain bound to the antithrombin III molecule, i.e., the enzymes relating to the fucose modification, is deleted, or cells obtained by various artificial techniques described in the above 1

The expression vectors that can be employed are those capable of autonomous replication or integration into the chromosome in the above host cells and comprising a promoter at a position appropriate for the transcription of the DNA encoding the desired antithrombin III molecule.

The cDNA can be prepared from a human or non-human animal tissue or cell according to the methods for preparing a cDNA described in the above 1 (1) (a) using, e.g., a probe or primers specific for the desired antithrombin III molecule.

When yeast is used as the host cell, YEP13 (ATCC 37115), YEp24 (ATCC 37051), YCp50 (ATCC 37419) or the like can be used as the expression vector.

As the promoter, any promoters capable of expressing in yeast strains can be used. Suitable promoters include promoters of genes of the glycolytic pathway such as hexokinase, PHO5 promoter, PGK promoter, GAP promoter, ADH promoter, gal 1 promoter, gal 10 promoter, heat shock protein promoter, MFα1 promoter and CUP 1 promoter.

Examples of suitable host cells are microorganisms belonging to the genera *Saccharomyces, Schizosaccharomyces, Kluyveromyces, Trichosporon* and *Schwanniomyces*, and specifically, *Saccharomyces cerevisiae, Schizosaccharomyces pombe, Kluyveromyces lactis, Trichosporon pullulans, Schwanniomyces alluvius* and the like.

Introduction of the recombinant vector can be carried out by any of the methods for introducing DNA into yeast, for example, electroporation [*Methods Enzymol.*, 194, 182 (1990)], the spheroplast method [*Proc. Natl. Acad. Sci. USA*, 84, 1929 (1978)], the lithium acetate method [*J. Bacteriology*, 153, 163 (1983)] and the method described in *Proc. Natl. Acad. Sci. USA*, 75, 1929 (1978).

When an animal cell is used as the host cell, pcDNAI, pcDM8 (commercially available from Funakoshi Co., Ltd.), pAGE107 (Japanese Published Unexamined Patent Application No. 22979/91; *Cytotechnology*, 3, 133 (1990)], pAS3-3 (Japanese Published Unexamined Patent Application No. 227075/90), pCDM8 [*Nature*, 329, 840 (1987)], pcDNAI/Amp (manufactured by Invitrogen Corp.), pREP4 (manufactured by Invitrogen Corp.), pAGE103 [*J. Biochemistry*, 101, 1307 (1987)], pAGE120, etc. can be used as the expression vector.

As the promoter, any promoters capable of expressing in animal cells can be used. Suitable promoters include the promoter of IE (immediate early) gene of cytomegalovirus (CMV), SV40 early promoter, the promoter of a retrovirus, metallothionein promoter, heat shock promoter, SRα promoter, etc. The enhancer of IE gene of human CMV may be used in combination with the promoter.

Examples of suitable host cells are human-derived Namalwa cells, monkey-derived COS cells, Chinese hamster-derived CHO cells, HBT5637 (Japanese Published Unexamined Patent Application No. 299/88), rat myeloma cells, mouse myeloma cells, cells derived from Syrian hamster kidney, embryonic stem cells, fertilized egg cells and the like.

Introduction of the recombinant vector can be carried out by any of the methods for introducing DNA into animal cells, for example, electroporation [*Cytotechnology*, 3 133 (1990)], the calcium phosphate method (Japanese Published Unexamined Patent Application No. 227075/90), lipofection [*Proc. Natl. Acad. Sci. USA*, 84, 7413 (1987)], the injection method (Manipulating the Mouse Embryo, A Laboratory Manual), the method using particle gun (gene gun) (Japanese Patent Nos. 2606856 and 2517813), the DEAE-dextran method [*Biomanual Series 4—Methods of Gene Transfer, Expression and Analysis* (Yodosha), edited by Takashi Yokota and Kenichi Arai (1994)] and the virus vector method (*Manipulating the Mouse Embryo*, Second Edition).

When an insect cell is used as the host cell, the protein can be expressed by the methods described in *Current Protocols in Molecular Biology; Baculovirus Expression Vectors, A Laboratory Manual*, W. H. Freeman and Company, New York (1992); Bio/Technology, 6, 47 (1988) or the like.

That is, the recombinant vector and a baculovirus are cotransfected into insect cells to obtain a recombinant virus in the culture supernatant of the insect cells, and then insect cells are infected with the recombinant virus, whereby the protein can be expressed.

The gene transfer vectors useful in this method include pVL1392, pVL1393 and pBlueBacIII (both manufactured by Invitrogen Corp.).

An example of the baculovirus is Autographa californica nuclear polyhedrosis virus, which is a virus infecting insects belonging to the family Barathra.

Examples of the insect cells are *Spodoptera frugiperda* ovarian cells Sf9 and Sf21 [*Current Protocols in Molecular Biology, Baculovirus Expression Vectors, A Laboratory Manual*, W. H. Freeman and Company, New York (1992)] and *Trichoplusia ni* ovarian cell High 5 (manufactured by Invitrogen Corp.).

Cotransfection of the above recombinant vector and the above baculovirus into insect cells for the preparation of the recombinant virus can be carried out by the calcium phosphate method (Japanese Published Unexamined Patent Application No. 227075/90), lipofection [*Proc. Natl. Acad. Sci. USA*, 84, 7413 (1987)] and the like.

When a plant cell is used as the host cell, Ti plasmid, tobacco mosaic virus vector or the like can be used as the expression vector.

As the promoter, any promoters capable of expressing in plant cells can be used. Suitable promoters include 35S promoter of cauliflower mosaic virus (CaMV), rice actin 1 promoter, etc.

Examples of suitable host cells are cells of plants such as tobacco, potato, tomato, carrot, soybean, rape, alfalfa, rice, wheat, barley, *Physcomitrella patens* and *Spirodela polyrhiza*.

Introduction of the recombinant vector can be carried out by any of the methods for introducing DNA into plant cells, for example, the method using *Agrobacterium* (Japanese Published Unexamined Patent Application Nos. 140885/84 and 70080/85, WO94/00977), electroporation (Japanese Published Unexamined Patent Application No. 251887/85) and the method using particle gun (gene gun) (Japanese Patent Nos. 2606856 and 2517813).

Expression of the antibody gene can be carried out not only by direct expression but also by secretory production, expression of a fusion protein of the Fc region and another protein and the like according to the methods described in *Molecular Cloning*, Second Edition and the like.

When the gene is expressed in yeast, an animal cell, an insect cell or a plant cell carrying an introduced gene relating to the synthesis of a sugar chain, an antithrombin III molecule to which a sugar or a sugar chain is added by the introduced gene can be obtained.

The antithrombin III composition can be produced by culturing the transformant obtained as above in a medium, allowing the antithrombin III molecules to form and accumulate in the culture, and recovering them from the culture. Culturing of the transformant in a medium can be carried out by conventional methods for culturing the host cell.

For the culturing of the transformant obtained by using a eucaryote such as yeast as the host, any of natural media and synthetic media can be used insofar as it is a medium suitable for efficient culturing of the transformant which contains carbon sources, nitrogen sources, inorganic salts and the like which can be assimilated by the host used.

As the carbon sources, any carbon sources that can be assimilated by the host can be used. Examples of suitable carbon sources include carbohydrates such as glucose, fructose, sucrose, molasses containing them, starch and starch hydrolyzate; organic acids such as acetic acid and propionic acid, and alcohols such as ethanol and propanol.

As the nitrogen sources, ammonia, ammonium salts of organic or inorganic acids such as ammonium chloride, ammonium sulfate, ammonium acetate and ammonium phosphate, and other nitrogen-containing compounds can be used as well as peptone, meat extract, yeast extract, corn steep liquor, casein hydrolyzate, soybean cake, soybean cake hydrolyzate, and various fermented microbial cells and digested products thereof.

Examples of the inorganic salts include potassium dihydrogenphosphate, dipotassium hydrogenphosphate, magnesium phosphate, magnesium sulfate, sodium chloride, ferrous sulfate, manganese sulfate, copper sulfate and calcium carbonate.

Culturing is usually carried out under aerobic conditions, for example, by shaking culture or submerged spinner culture under aeration. The culturing temperature is preferably 15 to 40° C., and the culturing period is usually 16 hours to 7 days. The pH is maintained at 3.0 to 9.0 during the culturing. The pH adjustment is carried out by using an organic or inorganic acid, an alkali solution, urea, calcium carbonate, ammonia, etc.

If necessary, antibiotics such as ampicillin and tetracycline may be added to the medium during the culturing.

When a microorganism transformed with a recombinant vector comprising an inducible promoter is cultured, an inducer may be added to the medium, if necessary. For example, in the case of a microorganism transformed with a recombinant vector comprising lac promoter, isopropyl-β-D-thiogalactopyranoside or the like may be added to the medium, and in the case of a microorganism transformed with a recombinant vector comprising trp promoter, indoleacrylic acid or the like may be added.

For the culturing of the transformant obtained by using an animal cell as the host cell, generally employed media such as RPMI1640 medium [*The Journal of the American Medical Association*, 199 519 (1967)], Eagle's MEM [*Science*, 122, 501 (1952)], Dulbecco's modified MEM [*Virology*, 8, 396 (1959)], 199 medium [*Proceeding of the Society for the Biological Medicine*, 73, 1 (1950)] and Whitten's medium [*Developmental Engineering Experimentation Manual—Preparation of Transgenic Mice* (Kodansha), edited by Motoya Katsuki (1987)], media prepared by adding fetal calf serum or the like to these media, etc. can be used as the medium.

Culturing is usually carried out under conditions of pH 6.0 to 8.0 at 30 to 40° C. for 1 to 7 days in the presence of 5% $CO_2$.

If necessary, antibiotics such as kanamycin and penicillin may be added to the medium during the culturing.

For the culturing of the transformant obtained by using an insect cell as the host cell, generally employed media such as TNM-FH medium (manufactured by Pharmingen, Inc.), Sf-900 II SFM medium (manufactured by Life Technologies, Inc.), ExCell 400 and ExCell 405 (manufactured by JRH Biosciences, Inc.) and Grace's Insect Medium [*Nature*, 19-5 788 (1962)) can be used as the medium.

Culturing is usually carried out under conditions of pH 6.0 to 7.0 at 25 to 30° C. for 1 to 5 days.

If necessary, antibiotics such as gentamicin may be added to the medium during the culturing.

The transformant obtained by using a plant cell as the host cell may be cultured in the form of cells as such or after differentiation into plant cells or plant organs. For the culturing of such transformant, generally employed media such as Murashige-Skoog (MS) medium and White medium, media prepared by adding phytohormones such as auxin and cytokinin to these media, etc. can be used as the medium.

Culturing is usually carried out under conditions of pH 5.0 to 9.0 at 20 to 40° C. for 3 to 60 days.

If necessary, antibiotics such as kanamycin and hygromycin may be added to the medium during the culturing.

As described above, the antithrombin III composition can be produced by culturing, according to a conventional culturing method, the transformant derived from a microorganism, an animal cell or a plant cell and carrying an expression vector into which DNA encoding the antithrombin III molecule has been inserted, allowing the antithrombin III composition to form and accumulate, and recovering the antithrombin m composition from the culture.

The process of the antithrombin III composition includes a method of intracellular production by host cells, a method of extracellular secretion by host cells and a method of production on outer membranes by host cells. A desirable production method can be adopted by changing the kind of the host cells used or the structure of the antithrombin III molecule to be produced.

When the antithrombin III composition is produced in host cells or on outer membranes of host cells, it is possible to force the antithrombin III composition to be secreted outside the host cells by applying the method of Paulson, et al. [*J. Biol. Chem.*, 264, 17619 (1989)], the method of Lowe, et al. [*Proc. Natl. Acad. Sci. USA*, 86, 8227 (1989), *Genes Develop.*, 4, 1288 (1990)], the methods described in Japanese Published Unexamined Patent Application No. 336963/93, WO94/23021 or the like.

That is, it is possible to force the desired antithrombin III molecule to be secreted outside the host cells by inserting DNA encoding the antithrombin III molecule and DNA encoding a signal peptide suitable for the expression of the antithrombin III molecule into an expression vector, introducing the expression vector into the host cells, and then expressing the antithrombin III molecule by use of recombinant DNA techniques.

It is also possible to increase the production of the antithrombin III composition by utilizing a gene amplification system using a dihydrofolate reductase gene or the like according to the method described in Japanese Published Unexamined Patent Application No. 227075/90.

Further, the antithrombin Ell composition can be produced using an animal having an introduced gene (non-human transgenic animal) or a plant having an introduced gene (transgenic plant) constructed by redifferentiation of animal or plant cells carrying the introduced gene.

When the transformant is an animal or plant, the antithrombin III composition can be produced by raising or cultivating the animal or plant in a usual manner, allowing the antithrombin III composition to form and accumulate therein, and recovering the antithrombin III composition from the animal or plant.

The method of preparing the antithrombin III composition using an animal can be carried out, for example, by producing the desired antithrombin III composition in an animal constructed by introducing the gene according to known methods [*American Journal of Clinical Nutrition*, 63, 639S (1996); *American Journal of Clinical Nutrition*, 63, 627S (1996); *Bio/Technology*, 9, 830 (1991)].

In the case of an animal, the antithrombin III composition can be produced, for example, by raising a non-human transgenic animal carrying the introduced DNA encoding the antithrombin III molecule, allowing the antithrombin III composition to form and accumulate in the animal, and recovering the antithrombin III composition from the animal. The places where the antithrombin III composition is formed and accumulated include milk (Japanese Published Unexamined Patent Application No. 309192/88), egg, etc. of the animal. As the promoter in this process, any promoters capable of expressing in an animal can be used. Preferred promoters include mammary gland cell-specific promoters such as at casein promoter, β casein promoter, β lactoglobulin promoter and whey acidic protein promoter.

The method of preparing the antithrombin III composition using a plant can be carried out, for example, by culturing a transgenic plant carrying the introduced DNA encoding the antithrombin III molecule according to known methods [Soshiki Baiyo (*Tissue Culture*), 20 (1994); Soshiki Baiyo (*Tissue Culture*), 1 (1995), *Trends in Biotechnology*, 15, 45 (1997)), allowing the antithrombin III composition to form and accumulate in the plant, and recovering the antithrombin III composition from the plant.

When the antithrombin III composition produced by the transformant carrying the introduced gene encoding the antithrombin III molecule is expressed in a soluble form in cells, the cells are recovered by centrifugation after the completion of culturing and suspended in an aqueous buffer, followed by disruption using a sonicator, French press, tanton Gaulin homogenizer, Dynomill or the like to obtain a cell-free extract. A purified preparation of the antithrombin III composition can be obtained by centrifuging the cell-free extract to obtain the supernatant and then subjecting the supernatant to ordinary means for isolating and purifying enzymes, e.g., extraction with a solvent, salting-out with ammonium sulfate, etc., desalting, precipitation with an organic solvent, anion exchange chromatography using resins such as diethylaminoethyl (DEAE)-Sepharose and DIAION HPA-75 (manufactured by Mitsubishi Chemical Corporation), cation exchange chromatography using resins such as S-Sepharose FF (manufactured by Pharmacia), hydrophobic chromatography using resins such as butyl Sepharose and phenyl Sepharose, gel filtration using a molecular sieve, affinity chromatography, chromatofocusing, and electrophoresis such as isoelectric focusing, alone or in combination. Specific examples include a method using immobilized heparin affinity chromatography developed by Miller-Anderson in 1974 (*Thromb. res.*, 5, 439 (1974); Zoku Seikagaku Jikken Koza (*A Sequel to Lectures on Experiments in Biochemistry*), 8, Blood, the second volume, pp. 569-574 (Tokyo Kagaku Dojin), edited by Tokyo Kagaku Dojin (1985)).

When the antithrombin III composition is expressed as an inclusion body in cells, the cells are similarly recovered and disrupted, followed by centrifugation to recover the inclusion body of the antithrombin III composition as a precipitate fraction. The recovered inclusion body of the antithrombin III composition is solubilized with a protein-denaturing agent. The solubilized antibody solution is diluted or dialyzed, whereby the antithrombin III composition is renatured to have normal conformation. Then, a purified preparation of the antithrombin III composition can be obtained by the same isolation and purification steps as described above.

When the antithrombin III composition is extracellularly secreted, the antithrombin III composition or its derivative can be recovered in the culture supernatant. That is, the culture is treated by the same means as above, e.g, centrifugation, to obtain the culture supernatant. A purified preparation of the antithrombin III composition can be obtained from the culture supernatant by using the same isolation and purification methods as described above.

When the host cell has already had an ability of expressing an antithrombin III molecule, a cell capable of expressing the antithrombin III molecule is prepared by using the method of the above-described 1, the cell is cultured, and an objective antithrombin III composition is purified from the culture to thereby prepare the antithrombin III composition.

3. Activity Evaluation of Antithrombin III Composition

The anti-blood coagulation activity of the purified antithrombin III composition can be measured by an in vitro test such as known antithrombin activity measuring method or heparin cofactor activity measuring method, an in vivo test using a disseminated intravascular coagulation (hereinafter referred to DIC) morbid state model animal (*The Second Series of Pharmaceutical Research and Development*, Volume 20, Blood Product, Ikuo Suzuki, ed., Hirokawa Publishing Company, Tokyo, Japan (1992), *The Course of Medicine* (Igaku no Ayumi), 120, 1147 (1982); *Japanese Pharmacology and Therapeutics*, 17, 5843 (1989), *Clinic and Research* (Rinsyo to Kenkyu), 62, 3573 (1985); *Clinic and Research* (Rinsyo to Kenkyu), 6, 3688 (1985); *Parmacometrics*, 30, 589 (1985) or the like. Specific examples are described below.

(1) Antithrombin Activity Measuring Method

A purified antithrombin III composition and a substance to be tested such as defibrinated plasma are serially diluted using 0.05 M Tris-HCl buffer, pH 8.3, containing 0.15 M NaCl and 0.2% human serum albumin.

To 100 μl of each of the diluted samples, 500 μl of 7.5 U/ml thrombin solution is added, and the reaction is carried out at 37° C. for 10 minutes. Then, 2 ml of a substrate solution prepared by diluting the thrombin-specific coloring substrate (HD-CHA-But-Arg-pNA) attached to Berichrome Antithrombin III (manufactured by Boehring Berge) to 0.25 M with a diluent is added thereto, and the reaction is carried out at 37° C. for 5 minutes. Thereafter, the reaction is stopped by adding 0.5 ml of 50% acetic acid.

By measuring absorbance in the reaction solution at 405 nm, a value is obtained by subtracting the absorbance of a reaction solution to which the substance to be tested at each dilution step was added from the absorbance of a control reaction solution to which antithrombin III as the substance to be tested was not added. This value as the amount of inactivated thrombin is plotted as ordinate, and dilution ratio of the substance to be tested as abscissa, on a semi-log graph paper. By linearly approximating relationship between the amount of inactivated thrombin and dilution ratio of the substance to be tested from the plotted measured values and comparing it with an approximate expression obtained as a result of the measurement of the purified antithrombin III composition and defibrinated plasma, the ratio of the purified antithrombin III composition to the defibrinated plasma can be calculated and its titer can be determined.

(2) Heparin Cofactor Activity Measuring Method

A purified antithrombin III composition and a substance to be tested such as defibrinated plasma are serially diluted using 0.05 M Tris-HCl buffer, pH 8 3, containing 0 15 M NaCl and 0.2% human serum albumin.

To 50 µl of each of the diluted samples, 1.0 ml of 0.3 unit thrombin solution containing 2.5 U/ml heparin is added, and the reaction is carried out at 37° C. for 5 minutes. Next, 100 µl of the substrate solution described in the above-described 3(1) adjusted to 2.0 mM is added thereto, and the reaction is carried out at 37° C. for 2 minutes. Thereafter, the reaction is stopped by adding 0.5 ml of 50% acetic acid.

After completion of the reaction, absorbance in the reaction mixture is measured at 405 nm, and then titer of the purified antithrombin III composition upon defibrinated plasma can be determined by the same method described in the above-described 3(1).

(3) In vivo Test Using DIC Morbid State Model Animal

Anti-blood coagulation activity of the purified antithrombin III composition in vivo can be examined using a rabbit acute DIC morbid state model [*Clinic and Research* (Rinsyo to Kenkyu), 62, 3573 (1985)), a rat acute DIC morbid state model [*Clinic and Research* (Rinsyo to Kenkyu), 62, 3688 (1985)], a pregnant rabbit acute DIC morbid state model [*Parmacometrics*, 30, 589 (1985)] or the like.

In addition, safety and therapeutic effect of the antithrombin III composition in human can also be evaluated using an animal species model relatively close to human, such as *Macaca fascicularis*.

4. Analysis of Sugar Chains in the Antithrombin III Composition

The sugar chain structure of an antithrombin IU molecule expressed in various cells can be analyzed according to general methods of analysis of the sugar chain structure of glycoproteins. For example, a sugar chain bound to an antithrombin III molecule consists of neutral sugars such as galactose, mannose and fucose, amino sugars such as N-acetylglucosamine, and acidic sugars such as sialic acid, and can be analyzed by techniques such as sugar composition analysis and sugar chain structure analysis using two-dimensional sugar chain mapping.

(1) Analysis of Neutral and Amino Sugar Compositions

The sugar chain composition of an antithrombin III molecule can be analyzed by carrying out acid hydrolysis of sugar chains with trifluoroacetic acid or the like to release neutral sugars or amino sugars and analyzing the composition ratio.

Specifically, the analysis can be carried out by a method using a carbohydrate analysis system (BioLC; product of Dionex). BioLC is a system for analyzing the sugar composition by HPAEC-PAD (high performance anion-exchange chromatography-pulsed amperometric detection) [*J. Liq. Chromatogr.*, 6, 1577 (1983)].

The composition ratio can also be analyzed by the fluorescence labeling method using 2-aminopyridine. Specifically, the composition ratio can be calculated by fluorescence labeling an acid-hydrolyzed sample by 2-aminopyridylation according to a known method [*Agric. Biol. Chem.*, 55(J), 283-284 (1991)] and then analyzing the composition by HPLC.

(2) Analysis of Sugar Chain Structure

The sugar chain structure of an antithrombin III molecule can be analyzed by two-dimensional sugar chain mapping [*Anal. Biochem.*, 171, 73 (1988); Seibutsukagaku Jikkenho (*Biochemical Experimentation Methods*) 23—Totanpakushitsu Tosa Kenkyuho (*Methods of Studies on Glycoprotein Sugar Chains*), Gakkai Shuppan Center, edited by Reiko Takahashi (1989)]. The two-dimensional sugar chain mapping is a method of deducing a sugar chain structure, for example, by plotting the retention time or elution position of a sugar chain by reversed phase chromatography as the X axis and the retention time or elution position of the sugar chain by normal phase chromatography as the Y axis, and comparing them with the results on known sugar chains.

Specifically, a sugar chain is released from an antithrombin III molecule by hydrazinolysis of the antithrombin III composition and subjected to fluorescence labeling with 2-aminopyridine (hereinafter referred to as PA) [*J. Biochem.*, 5, 197 (1984)]. After being separated from an excess PA-treating reagent by gel filtration, the sugar chain is subjected to reversed phase chromatography. Then, each peak of the sugar chain is subjected to normal phase chromatography. The sugar chain structure can be deduced by plotting the obtained results on a two-dimensional sugar chain map and comparing them with the spots of a sugar chain standard (manufactured by Takara Shuzo Co., Ltd.) or those in the literature [*Anal. Biochem.*, 171, 73 (1988)].

The structure deduced by the two-dimensional sugar chain mapping can be confirmed by carrying out mass spectrometry, e.g., MALDI-TOF-MS, of each sugar chain.

5. Immunoassay for Determining the Sugar Chain Structure of an Antithrombin III Molecule An antithrombin III composition consists of antithrombin III molecules which are different in sugar chain structure. The recombinant antithrombin III composition of the present invention, in which the ratio of sugar chains having a structure wherein fucose is bound to the N-acetylglucosamine in the reducing end to all the complex type N-glycoside-linked sugar chains bound to the Fc region is 0%, has a high ADCC activity. Such an antithrombin III composition can be identified using the method for analyzing the sugar chain structure of an antithrombin III molecule described in the above 4. Further, it can also be identified by immunoassays using lectins.

Discrimination of the sugar chain structure of an antithrombin III molecule by immunoassays using lectins can be made according to the immunoassays such as Western staining, RIA (radioimmunoassay), VIA (viroimmunoassay), EIA (enzymoimmunoassay), FIA (fluoroimmunoassay) and MIA (metalloimmunoassay) described in the literature [*Monoclonal Antibodies: Principles and Applications*, Wiley-Liss, Inc. (1995); *Enzyme Immunoassay*, 3rd Ed., Igaku Shoin (1987); *Enzyme Antibody Technique*, Revised Edition, Gakusai Kikaku (1985), etc.], for example, in the following manner.

A lectin recognizing the sugar chain structure of an antithrombin III molecule is labeled, and the labeled lectin is subjected to reaction with a sample antithrombin III composition, followed by measurement of the amount of a complex of the labeled lectin with the antithrombin III molecule.

Examples of lectins useful for determining the sugar chain structure of an antithrombin III molecule include WGA (wheat-germ agglutinin derived from *T. vulgaris*), ConA (concanavalin A derived from *C. ensiformis*), RIC (a toxin derived from *R. communis*), L-PHA (leukoagglutinin derived from *P. vulgaris*), LCA (lentil agglutinin derived from *L. culinaris*), PSA (pea lectin derived from *P. sativum*), AAL (*Aleuria aurantia* lectin), ACL (*Amaranthus caudatus* lectin), BPL (*Bauhinia purpurea* lectin), DSL (*Datura stramonium* lectin), DBA (*Dolichos biflorus* agglutinin), EBL (elderberry balk lectin), ECL (*Erythrina cristagalli* lectin), EEL (*Euonymus europaeus* lectin), GNL (*Galanthus nivalis* lectin), GSL (*Griffonia simplicifolia* lectin), HPA (*Helix pomatia* agglutinin), HHL (*Hippeastrum* hybrid lectin), Jacalin, LTL (*Lotus tetragonolobus* lectin), LEL (*Lycopersicon esculentum* lectin), MAL (*Maackia amurensis* lectin), MPL (*Maclura pomifera* lectin), NPL (*Narcissus pseudonarcissus* lectin), PNA (peanut agglutinin), E-PHA (*Phaseolus vulgaris* erythroagglutinin), PTL (*Psophocarpus tetragonolobus* lectin), RCA (*Ricinus communis* agglutinin), STL (*Solanum luberosum* lectin), SJA (*Sophora japonica* agglutinin), SBA (soybean agglutinin), UEA (*Ulex europacus* agglutinin), VVL (*Vicia villosa* lectin) and WFA (*Wisteria floribunda* agglutinin).

It is preferred to use lectins specifically recognizing a sugar chain structure wherein fucose is bound to the N-acetylglucosamine in the reducing end in a complex type N-glycoside-linked sugar chain. Examples of such lectins include lentil lectin LCA (lentil agglutinin derived from *Lens culinaris*), pea lectin PSA (pea lectin derived from *Pisum sativum*), broad bean lectin VFA (agglutinin derived from *Vicia faba*) and Aleuria aurantia lectin AAL (lectin derived from *Aleuria aurantia*).

6. Utilization of the Antithrombin III Composition

Since the antithrombin III composition obtained in the present invention has high heparin binding activity equivalent to that of the natural origin antithrombin III, it is useful in preventing and treating diseases which accompany blood coagulation.

It is known that platelets are adhered and coagulated in a region where blood coagulation is formed, such as a vascular endothelial tissue, to form thrombi in diseases which accompany blood coagulation. Thrombus is formed by various causes such as wound, arteriosclerosis and vascular inflammation, and embolus is generated when the thrombi are released and transferred by blood flow to clog other blood vessels. When an artery is obstructed by thrombi or emboli, the perfusion region downstream of the obstructed area becomes an ischemic state. Such various morbid states caused by thrombi are called thrombosis. Accordingly, the antithrombin III composition of the present invention is useful also in preventing and treating thrombosis.

Examples of the thrombosis include cerebral infarction (cerebrovascular accidents), myocardial infarction, appendicular arterial thromboembolism, deep venous thrombosis (thrombophlebitis), DIC, antithrombin III defective disease, gestational toxicosis and the like.

Cerebral infarction (cerebrovascular accidents) is a disease which accompanies obstruction of blood vessels induced by atherosclerosis lesions formed in the main cerebral arteries inside and outside of the skull. Since cerebral blood vessels are rapidly obstructed by thrombi, difficulty of moving such as hemiplegia and neurotic symptoms such as sensory disturbance of one side, disturbance of visual field, aphasia and dysarthria appear relatively quickly. Kinds of the cerebral infarction include lacuna cerebral infarction which is thrombosis of a relatively small cerebral artery generated by obstruction of arteriole branched from the main cerebral artery, and cardiogenic cerebral infarction which occurs due to obstruction of cerebral blood vessel by released thrombi once formed in the heart caused by heart diseases including myocardial infarction, valvular disease of heart such as mitral stenosis, articular fibrillation and the like.

Myocardial infarction is a result of the necrosis of myocardial cells caused by a blood flow disorder in a cardiac muscle of perfusion region due to obstruction of coronary artery. Although there are patients having anginal symptom such as chest pain and thoracic compression pain before onset of the disease, it suddenly onsets without prodromal symptom in most cases.

Examples of the appendicular arterial thromboembolism include arteriosclerosis obliterans (ASO) which is an obstructive lesion caused by arteriosclerosis in the legs and cause-unknown thromboangitis obliterans (TAO, Burger disease) which accompanies a vascular inflammation that causes thrombotic obstruction in arteries and veins of the limbs.

The deep venous thrombosis (thrombophlebitis) is a thrombosis which is generated by surgical operation, long-term lying in bed, infection, pregnancy, blood flow stagnation by wound or the like or vein injury. This is apt to occur in the left leg, and its main symptom is a swelling, but symptoms such as flushing of the skin, over-swelling of veins and pain also occur. This is also apt to occur by a long-term enplane, and such a case is particularly called economy class syndrome.

DIC is a disease which occurs as a result of an ischemic organ disorder caused by the broad range microthrombus formation in micro blood vessels due to excess activation of the blood coagulation system in the living body, and its basal diseases include acute leukemia, cancer, infectious disease, obstetric disease, fluminant hepatitis, aortic aneurysm, cardiac aneurysm, giant hemangioma, diabetic coma, intravascular hemolysis, operation, wound, burn wound, plastic operation and the like. Since its morbid state greatly varies depending on the basal disease, it is necessary to carry out anticoagulation therapy together with the treatment of basal disease.

The antithrombin III defective disease is a disease which accompanies quantitative reduction or qualitative abnormality of antithrombin III. The quantitative reduction or qualitative abnormality of antithrombin III causes inhibition reduction upon activated blood coagulation factors IX and X and thrombin and the like and becomes a cause of the onset of thrombosis. The antithrombin III defective disease was found in 1965 as a congenital hereditary disease in Norwegian families frequently generating thrombosis. The antithrombin III defective disease is found in several percent of patients having multiple or recurrent thrombosis. In the patients of antithrombin III defective disease, the onset frequency increases with the age, and this disease is generated in many cases through pregnancy, infection, surgical operation, wound, taking of oral contraceptives and the like as the start. Since thrombi are formed in many cases in leg deep veins, its onset is observed also in regions of pulmonary embolism, mesenteric vein, intracranial artery and vein and the like.

The gestational toxicosis is a disease which occurs during pregnancy, and its main symptoms are hypertension, proteinutia and edema. A disease in which similar symptoms are observed even after delivery is called secondary disease of gestational toxicosis and included in the gestational toxicosis in a broad sense. Abnormality of the coagulation fibrinolysis system is related to the origin of gestational toxicosis.

The antithrombin III composition can also be administered to patients before the onset of diseases for the purpose of preventing formation of thrombi. Specific examples of such patients include those patients having a possible danger of causing diseases such as vascular re-stricture after PTCA, unstable angina, peripheral artery obstruction, transient cerebral ischemic attack, acute myocardial infarction, non-Q wave myocardial infarction, DIC, thrombosis complication due to heparin thrombopenia, acute pulmonary thromboembolism, deep vein thrombosis, symptomatic pulmonary embolism and antithrombin III defective disease.

A pharmaceutical composition comprising the antithrombin III composition of the present invention may be administered alone as a therapeutic agent. However, it is preferably mixed with one or more pharmaceutically acceptable carrier and provided as a pharmaceutical preparation produced by an arbitrary method well known in the technical field of pharmaceutics.

It is desirable to administer the pharmaceutical composition by the route that is most effective for the treatment. Suitable administration routes include oral administration and parenteral administration such as intraoral administration intratracheal administration, intrarectal administration, subcutaneous administration, intramuscular administration and intravenous administration. In the case of an antithrombin III preparation, intravenous administration is preferable.

The pharmaceutical preparation may be in the form of spray, capsules, tablets, granules, syrup, emulsion, suppository, injection, ointment, tape, and the like.

The pharmaceutical preparations suitable for oral administration include emulsions, syrups, capsules, tablets, powders and granules.

Liquid preparations such as emulsions and syrups can be prepared using, as additives, water, sugars such as sucrose, sorbitol and fructose, glycols such as polyethylene glycol and propylene glycol, oils such as sesame oil, olive oil and soybean oil, antiseptics such as p-hydroxybenzoates, flavors such as strawberry flavor and peppermint, and the like.

Capsules, tablets, powders, granules or the like can be prepared using, as additives, excipients such as lactose, glucose, sucrose and mantutol, disintegrators such as starch and sodium alginate, lubricants such as magnesium stearate and talc, binders such as polyvinyl alcohol, hydroxypropyl cellulose and gelatin, surfactants such as fatty acid esters, plasticizers such as glycerin, and the like.

The pharmaceutical preparations suitable for parenteral administration include injections, suppositories and sprays.

Injections can be prepared using carriers comprising a salt solution, a glucose solution, or a mixture thereof or the like. It is also possible to prepare powder injections by freeze-drying the antithrombin III composition according to a conventional method and adding sodium chloride thereto.

Suppositories can be prepared using carriers such as cacao butter, hydrogenated fat and carboxylic acid.

The antithrombin III composition may be administered as such in the form of spray, but sprays may be prepared using carriers which do not stimulate the oral or airway mucous membrane of a recipient and which can disperse the antithrombin III composition as fine particles to facilitate absorption thereof Suitable carriers include lactose and glycerin. It is also possible to prepare aerosols, dry powders or the like according to the properties of the antithrombin III composition and the carriers used In preparing these parenteral preparations, the above-mentioned additives for the oral preparations may also be added.

The dose and administration frequency will vary depending on the desired therapeutic effect, the administration route, the period of treatment, the patient's age and body weight or the like. However, an appropriate daily dose of the active ingredient for an adult person is generally 10 µg/kg to 20 mg/kg.

Also, the anti-blood coagulation activity of the antithrombin III composition can be examined by an in vitro test such as antithrombin activity measuring method or heparin cofactor activity measuring method, an in vivo test using a DIC morbid state model using an experimental animal such as a rabbit, or the like.

The method for measuring antithrombin activity, the method for measuring heparin cofactor activity and the DIC morbid state model test are carried out by methods described in literatures (*The Second Series of Pharmaceutical Research and Development*, Volume 20, Blood Product, Ikuo Suzuki, ed., Hirokawa Publishing Company, Tokyo, Japan (1992); *The Course of Medicine* (Igaku no Ayumi), 120, 1147 (1982); *Japanese Pharmacology and Therapeutics*, 17, 5843 (1989); *Clinic and Research* (Rinsyo to Kenkyu), 62, 3573 (1985); *Clinic and Research* (Rinsyo to Kenkyu), 62, 3688 (1985); *Parmacometrics*, 30, 589 (1985) or the like.

The present invention is explained below in more detail based on Examples, however, Examples are simple illustrations, and the scope of the present invention is not limited thereto.

EXAMPLE 1

Construction of CHO/DG44 cell line in which both alleles of α1,6-fucosyltransferase (FUT8) on the genome have been disrupted The CHO/DG44 cell line comprising the deletion of a genome region for both alleles of α1,6-fucosyltransferase (hereinafter also referred to as FUT8) including the translation initiation codons was constructed according to the following steps.

1. Construction of Chinese Hamster FUT8 Gene Targeting Vector Plasmid pKOFUT8Neo Comprising Exon 2

Plasmid pKOFUT8Neo was constructed in the following manner using targeting vector plasmid pKOFUT8Puro of exon 2 of Chinese hamster FUT8 gene constructed by the method described in Example 13-1 of WO02/31140, and plasmid pKOSelectNeo (manufactured by Lexicon).

Using 16 units of a restriction enzyme AscI (New England Biolabs), 1.0 µg of plasmid pKOSelectNeo (manufactured by Lexicon) was allowed to react at 37° C. for 2 hours. The reacting solution was subjected to agarose gel electrophoresis, and approximately 1.6 Kb AscI fragment comprising the neomycin resistance gene expression unit was recovered using QIAquick Gel Extraction Kit (manufactured by QIAGEN).

Next, 1.0 µg of plasmid pKOFUT8Puro was allowed to react at 37° C. for 2 hours by using 16 units of a restriction enzyme AscI (manufactured by New England Biolabs). After the digestion reaction, the end of the DNA fragment was dephosphorylated with alkaline phospbatase derived from *Escherichia coli* C15 (manufactured by Takara Shuzo Co., Ltd.) according to the attached instructions. After the reaction, the DNA fragment was recovered by phenol/chloroform extraction and ethanol precipitation.

Figure 3:
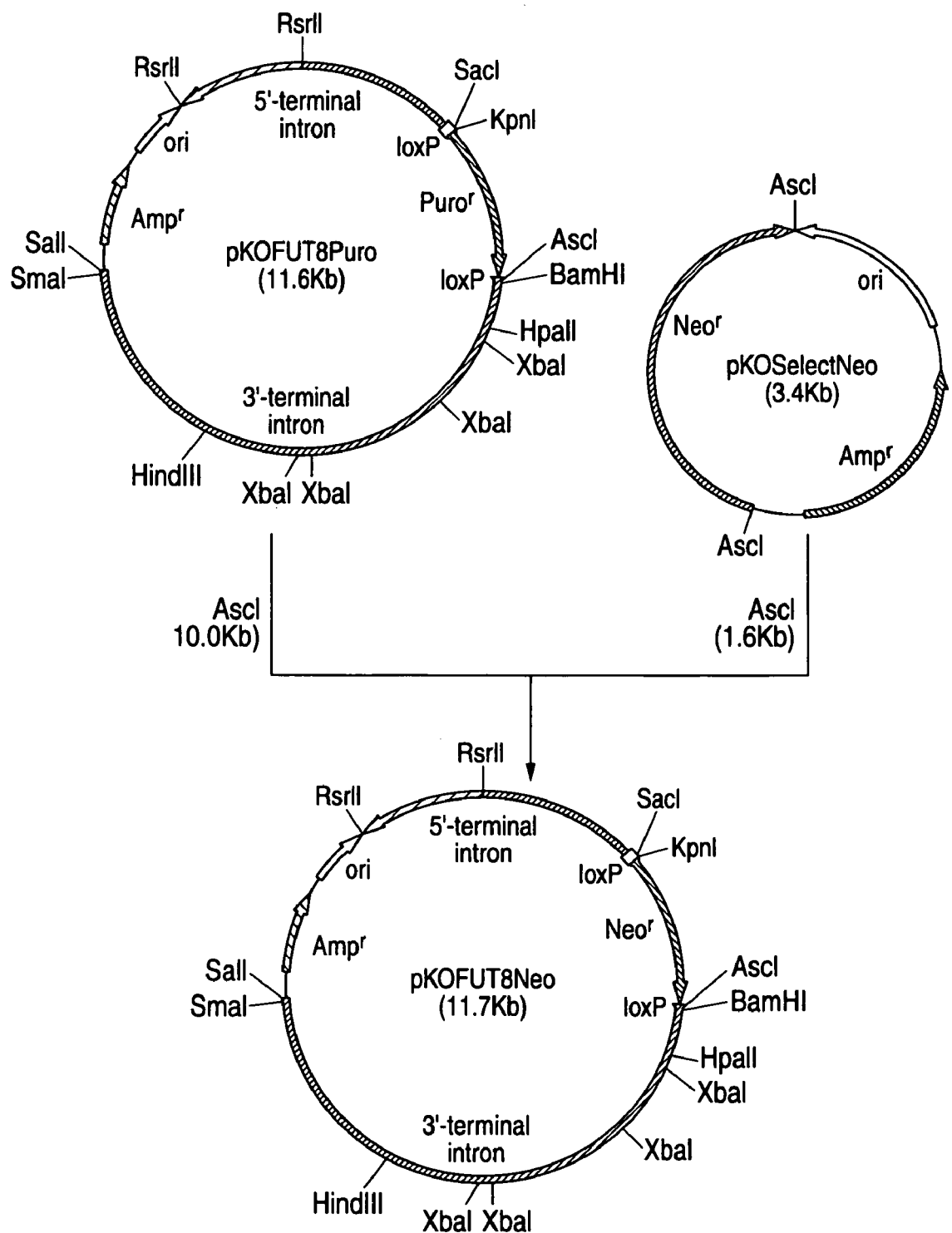
FIG. 3 shows the steps for constructing plasmid pKOFUT8Neo.

In the presence Ligation High (manufactured by Toyobo Co., Ltd.), 0.1 µg of the plasmid pKOSelectNeo-derived AscI fragment (approximately 1.6 Kb) and 0.1 µg of the plasmid pKOFUT8Puro-derived AscI fragment (approximately 10.1 Kb) obtained above were ligated, and *Escherichia coli* DH5α (manufactured by Toyobo Co., Ltd.) was transformed by using the resulting recombinant plasmid DNA according to the method of Cohen, et al [*Proc. Natl. Acad. Sci. U.S.A.*, 69, 2110 (1972)]. A plasmid DNA was prepared from each transformant and each nucleotide sequence was analyzed by using BigDye Terminator Cycle Sequencing Ready Reaction Kit v2.0 and DNA Sequencer ABI PRISM 377 (manufactured by Applied Biosystems). The plasmid pKOFUT8Neo having the objective nucleotide sequence shown in FIG. 3 was obtained, and was used as a targeting vector for the preparation of FUT8 gene-knockout cell of CHO cell.

2. Preparation of CHO Cell in which One Copy of the FUT8 Gene on the Genome has been Disrupted

(1) Obtaining of a Cell Line in which the Targeting Vector pKOFLT8Neo has been Introduced The Chinese hamster FUT8 genome region targeting vector pKOFUT8Neo constructed in Example 1-1 was introduced into Chinese hamster ovary-derived CHO/DG44 cells deficient in the dihydrofolate reductase gene (dhfr) [Somataic Cell and Molecular Genetics, 12, 555 (1986)] in the following manner.

After 280 µg of plasmid pKOFUT8Neo was allowed to react at 37° C. for 5 hours by adding 400 units of a restriction enzyme SalI (manufactured by New England Biolabs) for linearization, 4 µg of the linearized pKOFUT8Neo was introduced into $1.6 \times 10^6$ CHO/DG44 cells by electroporation [Cytotechnology, 3, 133 (1990)]. The resulting cells were suspended in IMDM-dFBS (10)-HT(1) [IMDM medium (manufactured by Invitrogen) containing 10% dialysis FBS (Invitrogen) and 1-fold concentration HT supplement (manufactured by Invitrogen)] and then inoculated into a 10-cm dish for adherent cell culture (manufactured by Falcon). After culturing in a 5% $CO_2$ incubator at 37° C. for 24 hours, the medium was replaced with 10 ml of IMDM-dFBS(10) (IMDM medium containing 10% dialysis FBS) containing 600 µg/ml G418 (manufactured by Nacalai Tesque, Inc.). Culturing was carried out in a 5% $CO_2$ incubator at 37° C. for 15 days while the above medium replacement was repeated every 3 to 4 days to obtain G418-resistant clones.

(2) Confirmation of Homologous Recombination by Genomic PCR

Confirmation of the homologous recombination in the G418-resistant clones obtained in the above (1) was carried out by genomic PCR in the following manner.

The G418-resistant clones on a 96-well plate were subjected to trypsinization, and a 2-fold volume of a frozen medium (20% DMSO, 40% fetal calf serum and 40% IDM) was added to each well to suspend the cells. One half of the cell suspension in each well was inoculated into a flat-bottomed 96-well plate for adherent cells (manufactured by Asahi Techno Glass) to prepare a replica plate, while the other half was stored by cryopreservation as a master plate.

The neomycin-resistant clones on the replica plate were cultured using IMDM-dFBS(10) containing 600 µg/ml G418 for one week, followed by recovery of cells. The genomic DNA of each clone was prepared from the recovered cells according to a known method [Analytical Biochemistry, 201, 331 (1992)] and then dissolved overnight in 30 µl of TE-RNase buffer (pH 8.0) (10 mmol/l Tris-HCl, 1 mmol/l EDTA, 200 µg/ml RNase A).

Primers used in the genomic PCR were designed as follows. Primers which bind to the sequence of a part exceeding a targeting vector homologous region (SEQ ID NO:20 or 21) and primers which bind to the sequence within the vector (SEQ ID NO:22 or 23) in the FUT8 genome region obtained by the method described in Example 12 of WO03/31140 (SEQ ID NO:13) were prepared. The following polymerase chain reaction (PCR) was carried out by using them. Specifically, a reaction mixture [25 µl; DNA polymerase ExTaq (manufactured by Takara Shuzo Co., Ltd.), ExTaq buffer (manufactured by Takara Shuzo Co., Ltd.), 0.2 mmol/l dNTPs, 0.5 µmol/l each of the above gene-specific primers (forward primer: SEQ ID NO:20 or 21; reverse primer: SEQ ID NO:22 or 23)) containing 10 µl of each genomic DNA solution prepared above was prepared, and PCR was carried out, after heating at 94° C. for 3 minutes, by cycles, one cycle consisting of reaction at 94° C. for one minute, reaction at 60° C. for one minute and reaction at 72° C. for 2 minutes.

After the PCR, the reaction mixture was subjected to 0.8% (w/v) agarose gel electrophoresis, and cell lines with which a specific amplification (approximately 1.7 Kb) containing a boundary part of the CHO cell genomic region and the target vector homologous region was observed were determined to be positive clones.

(3) Confirmation of Homologous Recombination by Genomic Southern Blotting

Confirmation of the homologous recombination in the positive clones obtained in the above (2) was carried out by Southern blotting in the following manner.

From the master plates stored by cryopreservation in the above (2), a 96-well plate containing the positive clones found in (2) was selected. After the plate was allowed to stand at 5% $CO_2$ and 37° C. for 10 minutes, the cells in the wells corresponding to the positive clones were inoculated into a flat-bottomed 24-well plate for adherent cells (manufactured by Greiner). After culturing using IMDM-dFBS(10) containing at a concentration of 600 µg/ml for one week, the cells were inoculated into a flat-bottomed 6-well plate for adherent cells (Greiner). The genomic DNA of each clone was prepared from the recovered cells from the plate according to a known method [Nucleic Acids Research, 3, 2303 (1976)] and then dissolved overnight in 150 µl of TE-RNase buffer (pH 8.0) (10 mmol/l Tris-HCl, 1 mmol/l EDTA, 200 µg/ml RNase A).

The genomic DNA prepared above (12 µg) was digested with 25 units of a restriction enzyme BamHI (manufactured by New England Biolabs) at 37° C. overnight. A DNA fragment was recovered by ethanol precipitation from the reaction mixture. The recovered fragment was dissolved in 20 µl of TE buffer (pH 8.0) (10 mmol/l Tris-HCl, 1 mmol/l EDTA) and then subjected to 0.6% (w/v) agarose gel electrophoresis. After the electrophoresis, the genomic DNA was transferred to a nylon membrane according to a known method [Proc. Natl. Acad. Sci. USA, 76, 3683 (1979)], followed by heat treatment of the nylon membrane at 80° C. for 2 hours for immobilization.

Separately, a probe used in the Southern blotting was prepared in the following manner. Firstly, PCR was carried out as follows by using primers which bind to the sequence of a part exceeding the targeting vector homologous region (SEQ ID NOs:24 and 25) in the FUT8 genome region (SEQ ID NO:13) obtained by the method described in Example 12 of WO02/31140. That is, 20 µl of a reaction mixture [DNA polymerase ExTaq (manufactured by Takara Shuzo Co., Ltd.), ExTaq buffer (manufactured by Takara Shuzo Co., Ltd.), 0.2 mmol/l dNTPs, 0.5 µmol/l each of the above gene-specific primers (SEQ ID NOs:24 and 25)] containing 4.0 ng of plasmid pFUT8fgE2-2 described in Example 12 of WO02/31140 was prepared, and PCR was carried out, after heating at 94° C. for one minute, by 25 cycles, one cycle consisting of reaction at 94° C. for 30 seconds, reaction at 55° C. for 30 seconds and reaction at 74° C. for one minute. After the PCR, the reaction mixture was subjected to 1.75% (w/v) agarose gel electrophoresis, and approximately 230 bp probe DNA fragment was purified. Then, 5 µl of the obtained probe DNA solution was subjected to radiolabeling using [$\alpha$-$^{32}$P] dCTP 1.75 MBq and Megaprime DNA Labelling system, dCTP (manufactured by Amersham Pharmacia Biotech).

Hybridization was carried out in the following manner. The above nylon membrane was put into a roller bottle and 15 ml of a hybridization solution [5×SSPE, 50× Denhaldt's solution, 0.5% (w/v) SDS, 100 µg/ml salmon sperm DNA] was added thereto. Prehybridization was cared out at 65° C. for 3 hours. Then, the $^{32}$P-labeled probe DNA was heat-denatured and put into the bottle, followed by heating at 65° C. overnight.

After the hybridization, the nylon membrane was immersed in 50 ml of 2×SSC-0.1% (w/v) SDS and heated at 65° C. for 15 minutes. After a washing step was repeated twice, the nylon membrane was immersed in 50 ml of 0.2× SSC-0.1% (w/v) SDS and heated at 65° C. for 15 minutes. After washing, the nylon membrane was exposed to an X-ray film at −80° C. for development.

The genomic DNAs of the parent cell line CHO/DG44 and the 50-10-104 cell line, which is the positive clone obtained in the above (2) were analyzed according to the present method. In the CHO/DG44 cell line, only approximately 25.5 Kb fragment derived from the wild-type FUT8 allele was detected. On the other hand, in the positive clone, i.e. 50-10-104 cell line, approximately 20.0 Kb fragment specific to the allele which underwent homologous recombination was detected in addition to approximately 25.5 Kb fragment derived from the wild-type FUT8 allele. The quantitative ratio of these two kinds of fragments was 1:1, whereby it was confirmed that the 50-10-104 cell line was a hemi-knockout clone wherein one copy of the FUT8 allele was disrupted.

3. Preparation of CHO/DG44 Cell Line in which the FUT8 Gene on the Genome has been Double-knocked Out (1) Obtaining of a Cell Line in which Targeting Vector pKOFUT8Puro has been Introduced In order to disrupt the other FUT8 allele in the FUT8 gene-hemi-knockout clone obtained in Example 1-2(2), the Chinese hamster FUT8 gene exon 2 targeting vector plasmid pKOFUT8Puro constructed by the method described in Example 13-1 of WO02/3 1140 was introduced into the clone in the following manner.

After 440 μg of plasmid pKOFUT8Puro was allowed to react at 37° C. for 5 hours by adding 800 units of a restriction enzyme SalI (manufactured by New England Biolabs) for linearization, 4 μg of the linearized pKOFUT8Puro was introduced into 1.6×10$^6$ cells of the FUT8 gene-hemi-knockout clone by electroporation [*Cytotechnology*, 3, 133 (1990)]. The resulting cells were suspended in IMDM-dFBS(10)-HT (1) and then inoculated into a 10-cm dish for adherent cell culture (manufactured by Falcon). After culturing in a 5% $CO_2$ incubator at 37° C. for 24 hours, the medium was replaced with 10 ml of IMDM-dFBS(10)-HT(1) containing 15 μg/ml puromycin (manufactured by SIGMA).

Culturing was carried out at 5% $CO_2$ for 15 days while the above medium replacement was repeated every 7 days to obtain puromycin-resistant clones.

(2) Confirmation of Homologous Recombination by Genomic Southern Blotting

Confirmation of the homologous recombination in the drug-resistant clones obtained in the above (1) was carried out by genomic Southern blotting in the following manner.

A culture supernatant was removed from a 10-cm dish in which the puromycin-resistant clones were expressed, 7 ml of a phosphate buffer was poured, and the dish was moved under a stereoscopic microscope. Next, colonies were ripped off and sucked by using PIPETMAN (manufactured by GILSON) and were collected in a round-bottomed 96-well plate (manufactured by Falcon). After trypsinizaton, each clone was inoculated into a flat-bottomed 96-well plate for adherent cells (manufactured by Asahi Techno Glass), followed by culturing using IMDM-dFBS(10)-HT(1) containing 15 μg/ml puromycin (manufactured by SIGMA) for one week.

After the culturing, each clone on the above plate was subjected to trypsinization and the resulting cells were inoculated into a flat-bottomed 24-well plate for adherent cells (manufactured by Greiner). After culturing using IMDM-dFBS(10)-HT(1) containing 15 μg/ml puromycin (manufactured by SIGMA) for one week, the cells were inoculated into a flat-bottomed 6-well plate for adherent cells (manufactured by Greiner). The genomic DNA of each clone was prepared from the plate according to a known method [*Nucleic Acids Research*, 3, 2303 (1976)) and then dissolved overnight in 150 μl of TE-RNase buffer (pH 8.0).

The genomic DNA prepared above (12 μg) was digested with 25 units of a restriction enzyme BamHI (manufactured by New England Biolabs) at 37° C. overnight for digestion reaction, and a DNA fragment recovered by ethanol precipitation was dissolved in 20 μl of TE buffer (pH 8.0) and then subjected to 0.6% (w/v) agarose gel electrophoresis. After the electrophoresis, the genomic DNA was transferred to a nylon membrane according to a known method [*Proc. Natl. Acad. Sci. USA*, 76, 3683 (1979)], followed by heat treatment of the nylon membrane at 80° C. for 2 hours.

Separately, a probe used in the Southern blotting was prepared in the following manner. First, the following PCR was carried out by using primers which bind to the sequence of a part exceeding the targeting vector homologous region in the FUT8 genomic region (SEQ ID NOs:26 and 27) in the FUT8 genomic region. That is, 20 μl of a reaction mixture [DNA polymerase ExTaq (manufactured by Takara Shuzo Co., Ltd.), ExTaq buffer (manufactured by Takara Shuzo Co., Ltd.), 0.2 mmol/l dNTPs, 0.5 μmol/l each of the above gene-specific primers (SEQ ID NOs:26 and 27)] containing 4.0 ng of the plasmid pFUT8fgE2-2 constructed by the method described in Example 12 of WO02/31140 was prepared, and PCR was carried out, after heating at 94° C. for one minute, by 25 cycles, one cycle consisting of reaction at 94° C. for 30 seconds, reaction at 55° C. for 30 seconds and reaction at 74° C. for one minute. After the PCR, the reaction mixture was subjected to 1.75% (w/v) agarose gel electrophoresis, and approximately 230 bp probe DNA fragment was purified. Then, 5 μl of the obtained probe DNA solution was subjected to radiolabeling using [α-$^{32}$P] dCTP 1.75 MBq and Megaprime DNA Labelling system, dCTP (manufactured by Amersham Pharmacia Biotech).

Hybridization was carried out in the following manner. The above nylon membrane was put into a roller bottle and 15 ml of a hybridization solution [5×SSPE, 50× Denhaldt's solution, 0.5% (w/v) SDS, 100 μg/ml salmon sperm DNA] was added thereto. Prehybridization was carried out at 65° C. for 3 hours. Then, the $^{32}$P-labeled probe DNA was heat-denatured and put into the bottle, followed by heating at 65° C. overnight.

After the hybridization, the nylon membrane was immersed in 50 ml of 2×SSC-0.1% (w/v) SDS and heated at 65° C. for 15 minutes. After this washing step was repeated twice, the nylon membrane was immersed in 50 ml of 0.2× SSC-0.1% (w/v) SDS and heated at 65° C. for 15 minutes. After washing, the nylon membrane was exposed to an X-ray film at −80° C. for development.

The genomic DNA of the WK704 cell line, which is one of the puromycin-resistant clones obtained from the 50-10-104 cell line according to the method described in the above (1), was analyzed according to the present method. In the WK704 cell line, approximately 25.5 Kb fragment derived from the wild-type FUT8 allele was eliminated and only approximately 20.0 Kb fragment specific to the allele which underwent homologous recombination was detected. From this result, it was confirmed that the WK704 cell line was a clone wherein both FUT8 alleles were disrupted.

4. Removal of the Drug Resistance Genes from FUT8 Gene-Double-Knockout Cells (1) Introduction of Cre Recombinase Expression Vector Into FUT8-double-knockout clone obtained in the above 3 of Example 1, the Cre recombinase expression vector pBS185 (manufactured by Life Technologies) was introduced in the following manner.

After 4 µg of plasmid pBS185 was introduced into $1.6 \times 10^6$ cells by electroporation [*Cytotechnology*, 3, 133 (1990)], the resulting cells were suspended in 10 ml of IMDM-dFBS(10)-HT(1) and the suspension was diluted 20000-fold with the same medium. The diluted suspension was inoculated into seven 10-cm dishes for adherent cell culture (manufactured by Falcon), followed by culturing in 5% $CO_2$ at 37° C. for 10 days to form colonies.

(2) Obtaining of a Cell Line in which the Cre Recombinase Expression Vector has been Introduced Arbitrary clones were collected from colonies obtained by gene introduction into FUT8-double-knockout clones prepared in the above 3 of Example 1 in the following manner. First, a culture supernatant was removed from a 10-cm dish, 7 ml of a phosphate buffer was poured, and the dish was moved under a stereoscopic microscope. Next, colonies were ripped off and sucked using PIPETMAN (manufactured by GILSON) and were collected in a round-bottomed 96-well plate (manufactured by Falcon). After trypsinization, each clone was inoculated into a flat-bottomed 96-well plate for adherent cells (manufactured by Iwaki Glass), followed by culturing using IMDM-dFBS(10)-HT(1) for one week.

After the culturing, each clone on the above plate was subjected to trypsinization, and a 2-fold volume of a frozen medium (20% DMSO, 40% fetal calf serum and 40% IMDM) was mixed therewith. One half thereof was inoculated into a flat-bottomed 96-well plate for adherent cells (manufactured by Iwaki Glass) to prepare a replica plate, while the other half was stored by cryopreservation as a master plate.

The replica plate was cultured using IMDM-dFBS(10)-HT (1) containing 600 µg/ml G418 and 15 µg/ml puromycin for 7 days. Positive clones in which the drug resistance genes on both alleles between loxP sequences has been removed by the expression of Cre recombinase die in the presence of G418 and puromycin. The positive clones were selected according to this negative selection method.

(3) Confirmation of Removal of the Drug Resistance Genes by Genomic Southern Blotting Confirmation of the removal of the drug resistance genes in the positive clones collected in the above (2) was carried out by genomic Southern blotting in the following manner.

From the master plates stored by cryopreservation in the above (2), a 96-well plate containing the above positive clones was selected. After the plate was allowed to stand at 5% $CO_2$ and 37° C. for 10 minutes, the cells in the wells corresponding to the above clones were inoculated into a flat-bottomed 24-well plate for adherent cells (manufactured by Greiner). After culturing using IMDM (manufactured by Invitrogen) to which 10% fetal bovine serum (manufactured by Invitrogen) and 1× concentration HT supplement (manufactured by Invitrogen) bad been added for one week, the cells were inoculated into a flat-bottomed 6-well plate for adherent cells (manufactured by Greiner). The genomic DNA of each clone was prepared from the plate according to a known method [*Nucleic Acids Research*, 3, 2303 (1976)] and then dissolved overnight in 150 µl of TE-RNase buffer (pH 8.0).

The genomic DNA prepared above (12 µg) was digested with 20 units of a restriction enzyme NheI (New England Biolabs) at 37° C. overnight. A DNA fragment recovered from the reaction mixture by ethanol precipitation was dissolved in 20 µl of TE buffer (pH 8.0) and then subjected to 0.6% (w/v) agarose gel electrophoresis. After the electrophoresis, the genomic DNA was transferred to a nylon membrane according to a known method [*Proc. Natl. Acad. Sci. USA*, 76, 3683 (1979)], followed by heat treatment of the nylon membrane at 80° C. for 2 hours for immobilization.

Separately, a probe used in the Southern blotting was prepared in the following manner. Next, the following PCR was carried out by using primers which bind to the sequence of a part exceeding the targeting vector homologous region in the FUT8 genomic region (SEQ ID NOs:26 and 27). That is, a reaction mixture [20 µl DNA polymerase ExTaq (manufactured by Takara Shuzo Co., Ltd.), ExTaq buffer (manufactured by Takara Shuzo Co., Ltd.), 0.2 mmol/l dNTPs, 0.5 µmol/l each of the above gene-specific primers (SEQ ID NOs:26 and 27)] containing 4.0 ng of the plasmid pFUT8fgE2-2 described in Example 12 of WO02/31140 as a template was prepared, and PCR was carried out, after heating at 94° C. for one minute, by 25 cycles, one cycle consisting of reaction at 94° C. for 30 seconds, reaction at 55° C. for 30 seconds and reaction at 74° C. for one minute. After the PCR, the reaction mixture was subjected to 1.75% (w/v) agarose gel electrophoresis, and approximately 230 bp probe DNA fragment was purified. Then, 5 µl of the obtained probe DNA solution was subjected to radiolabeling using [α-$^{32}$P] dCTP 1.75 MBq and Megaprime DNA Labelling system, dCTP (manufactured by Amersham Pharmacia Biotech).

Hybridization was carried out in the following manner. The above nylon membrane was put into a roller bottle and 15 ml of a hybridization solution [5×SSPE, 50× Denhaldt's solution, 0.5% (w/v) SDS, 100 µg/ml salmon sperm DNA] was added thereto. Prehybridization was carried out at 65° C. for 3 hours. Then, the $^{32}$P-labeled probe DNA was heat-denatured and put into the bottle, followed by heating at 65° C. overnight.

After the hybridization, the nylon membrane was immersed in 50 ml of 2×SSC-0.1% (w/v) SDS and heated at 65° C. for 15 minutes. After this washing step was repeated twice, the nylon membrane was immersed in 50 ml of 0.2× SSC-0.1% (w/v) SDS and heated at 65° C. for 15 minutes. After washing, the nylon membrane was exposed to an X-ray film at −80° C. for development.

By the above-described treatment with the restriction enzyme NheI, approximately 8.0 Kb DNA fragment was derived from the wild-type FUT8 allele. Also, by the similar treatment with the restriction enzyme, approximately 9.5 Kb DNA fragment was obtained from the allele which underwent homologous recombination with the targeting vector. Furthermore, by the similar treatment, approximately 8.0 Kb DNA fragment was derived when the neomycin resistance gene (approximately 1.6 Kb) and the puromycin resistance gene (approximately 1.5 Kb) were removed from the allele which underwent homologous recombination.

The genomic DNAs of the parent cell line CHO/DG44, the 50-10-104 cell line described in the above item 2, the WK704 cell line described in the above item 3, and the 4-5-C3 cell line, which is one of the drug-sensitive clones obtained from the WK704 cell line by the method described in the above (2), were analyzed according to the present method. In the CHO/DG44 cell line, only approximately 8.0 Kb DNA fragment derived from the wild-type FUT8 allele was detected. In the 50-10-104 cell line and the WK704 cell line, approximately 9.5 Kb DNA fragment derived from the allele which underwent homologous recombination was observed. On the other hand, in the 4-5-C3 cell line, only approximately 8.0 Kb DNA fragment resulting from the removal of the neomycin resistance gene (approximately 1.6 Kb) and the puromycin resistance gene (approximately 1.5 Kb) from the allele which underwent homologous recombination was detected. From the above results, it was confirmed that the drug resistance genes had been removed by Cre recombinase in the 4-5-C3 cell line.

Besides the 4-5-C3 cell line, plural FUT8 gene-double-knockout clones in which the drug-resistance gene had been removed (hereinafter referred to as FUT8 gene-double-knockout cells) were obtained.

EXAMPLE 2

Expression of Recombinant Antithrombin III by FUT8 Gene-Double-Knockout Cell:

An FUT8 gene-double-knockout cell line which expresses a recombinant antithrombin III was prepared by the method shown below.

1. Polymerase Chain Reaction (PCR)

The following PCR was carried out by preparing two primers (SEQ ID NOs:28 and 29) from a sequence of human antithrombin III gene (UniGene: Hs.75599). That is, 20 μl of a reaction mixture consisting of Pyrobest® DNA polymerase (manufactured by Takara Bio), 10× Pyrobest® buffer, 0.2 mmol/l dNTP mixture and 0.5 μmol/l of the above-described gene-specific primers (SEQ ID NOs:28 and 29), containing a human liver-derived cDNA (manufactured by Invitrogen) as the template, was prepared, and PCR was carried out, after heating at 94° C. for one minute, by 30 cycles, one cycle consisting of reaction at 94° C. for 30 seconds, reaction at 55° C. for one minute and reaction at 74° C. for 2 minutes. After the PCR, the reaction mixture was subjected to 1.5% (w/v) agarose gel electrophoresis to confirm that a DNA fragment containing a human antithrombin III gene of approximately 1,400 bp was specifically amplified.

2. Preparation of Plasmid pBS-ATIII

Figure 4:
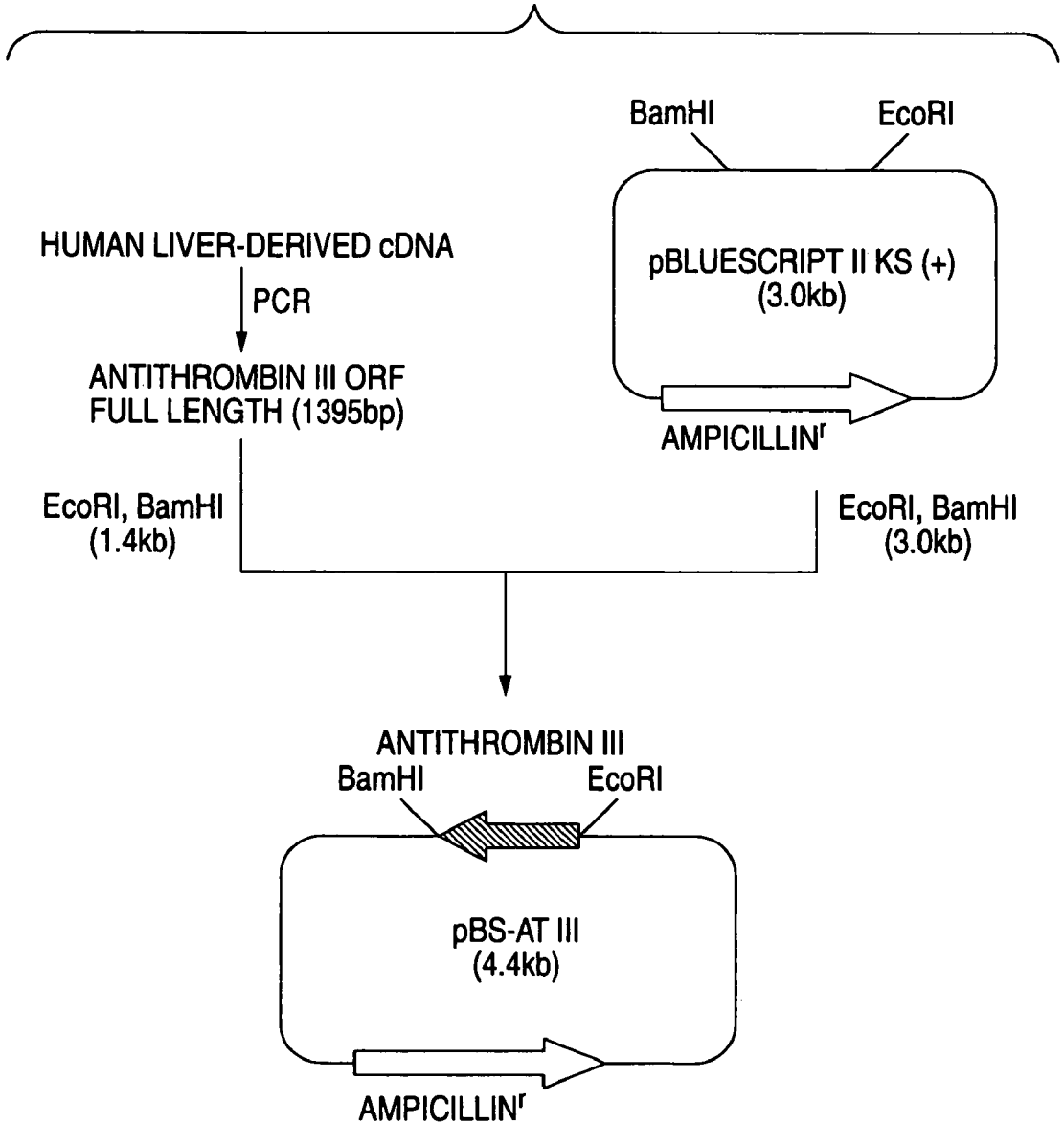
FIG. 4 shows the steps for constructing plasmid pBSATIII.

Phenol/chloroform extraction treatment and ethanol precipitation were carried out on the PCR product prepared in the above 1, and the thus recovered purified DNA fragment was dissolved in 17 μl of sterile water. Next, 20 μl of a reaction mixture was prepared by adding 10 units of a restriction enzyme EcoRI (manufactured by Takara Bio), 10 units of BamHI (manufactured by Takara Bio) and 2 μl of 10× H buffer (manufactured by Takara Bio) to the solution, and the digestion reaction was carried out at 37° C. for 16 hours. Next, 3 μg of a plasmid pBluescript II KS(+) (manufactured by Stratagene) was dissolved in 17.5 μl of sterile water. Next, 20 μl of a reaction mixture was prepared by adding 10 units of EcoRI and 2 μl of 10× H buffer to the solution, and the digestion reaction was carried out at 37° C. for 16 hours. After the reaction, phenol/chloroform extraction treatment and ethanol precipitation were carried out, and the thus recovered plasmid was dissolved in 17.5 μl of sterile water. Next, 20 μl of a reaction mixture was further prepared by adding 10 units of BamHI and 2 μl of 10× K buffer to the solution, and the digestion reaction was carried out at 37° C. for 16 hours. The PCR product fragment (EcoRI-BamHI) containing human antithrombin III gene and the pBluescript II KS(+) fragment (EcoRI-BamHI), both obtained in the above, were subjected to 1.5% (w/v) agarose gel electrophoresis, and respective DNA fragments of approximately 1.4 kb and 3.0 kb were purified using QIAquick Gel Extraction Kit (manufactured by QIAGEN) Next, 20 ng of the purified PCR product fragment (EcoRI-BamHI) and 80 ng of the purified pBluescript II KS(+) fragment (EcoRI-BamHI) were ligated in the presence of Ligation High (manufactured by Toyobo Co., Ltd.), and an *Escherichia coli* strain DH5α (manufactured by Toyobo Co., Ltd.) was transformed using the thus obtained recombinant plasmid DNA. Plasmid DNA was prepared from each transformant, and its nucleotide sequence was analyzed using BigDye Terminator Cycle Sequencing Ready Reaction Kit v2.0 (manufactured by Applied Biosystems) and a DNA sequencer ABI PRISM 377 (manufactured by Applied Biosystems). As a result, a plasmid pBS-ATIII containing a gene sequence of a full translation region of human antithrombin III was obtained (FIG. 4).

3. Preparation of Plasmid pKAN-ATIII

In 17 μl of sterile water, 3 μg of the PBS-ATIII prepared in the above was dissolved, and 10 units of EcoRI (manufactured by Takara Bio), 10 units of BamHI (manufactured by Takara Bio) and 2 μl of 10× H buffer were added thereto to obtain 20 μl of a reaction mixture, and the digestion reaction was carried out at 37° C. for 16 hours.

Figure 5:
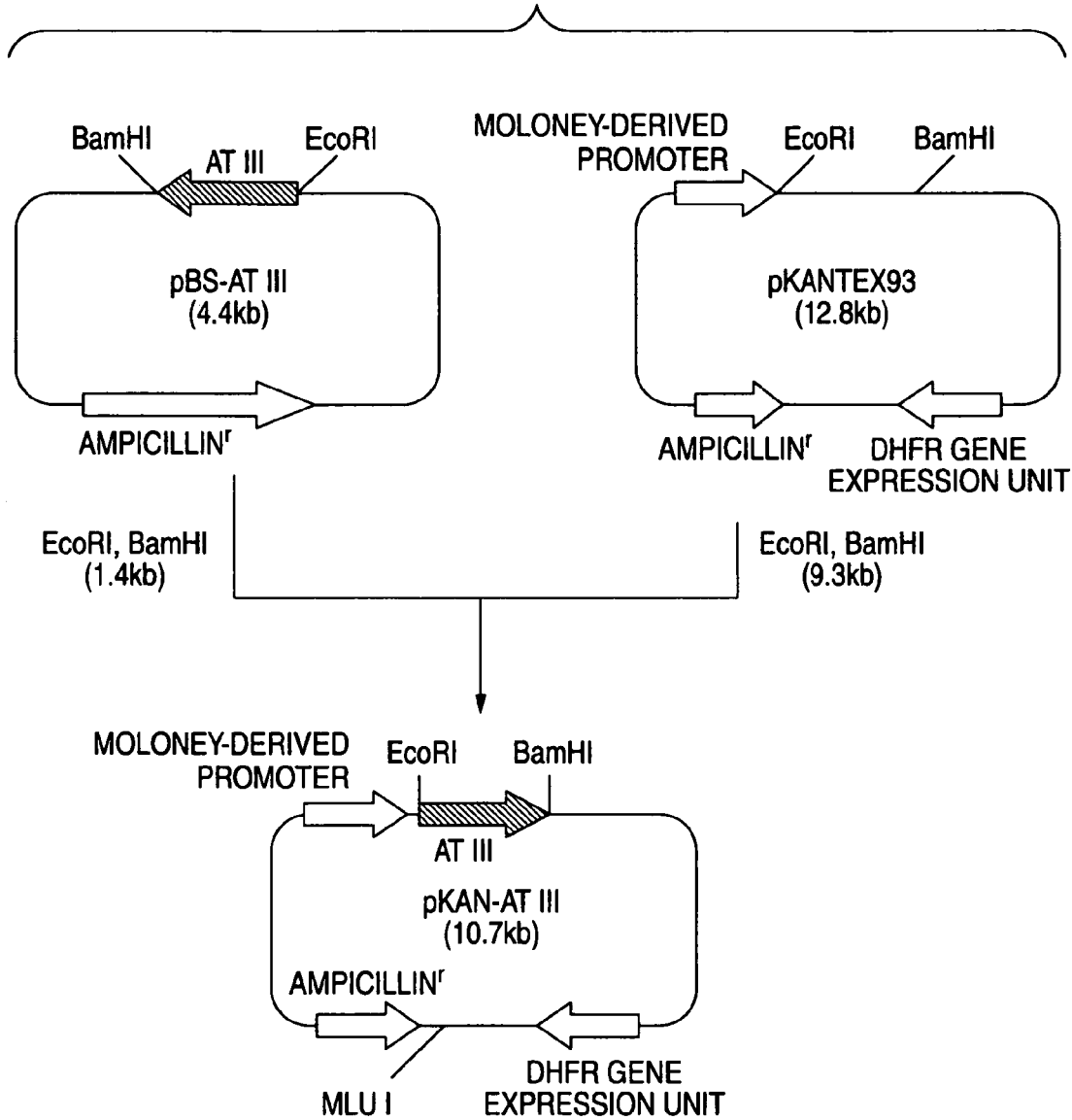
FIG. 5 shows the steps for constructing plasmid pKAN-ATIII.

Next, 3 μg of a plasmid pKANTEX93 (WO97/10354) was dissolved in 17.5 μl of sterile water. Next, 20 μl of a reaction mixture was prepared by adding 10 units of EcoRI and 2 μl of 10× H buffer to the solution, and the digestion reaction was carried out at 37° C. for 16 hours. After the reaction, phenol/chloroform extraction treatment and ethanol precipitation were carried out, and the thus recovered plasmid was dissolved in 17.5 μl of sterile water. Next, 20 μl of a reaction mixture was further prepared by adding 10 units of BamHI and 2 μl of 10× K buffer to the solution, and the digestion reaction was carried out at 37° C. for 16 hours. The pBS-ATIII fragment (EcoRI-BamHI) and pKANTEX93 fragment (EcoRI-BamHI), both obtained in the above, were subjected to 1.5% (w/v) agarose gel electrophoresis, and respective DNA fragments of approximately 1.4 kb and 9.0 kb were purified using QIAquick Gel Extraction Kit (manufactured by QIAGEN). Next, 50 ng of the purified pBS-ATIII fragment (EcoRI-BamHI) and 30 ng of the purified pKANTEX93 fragment (EcoRI-BamHI) were ligated in the presence of Ligation High (manufactured by Toyobo Co., Ltd.), and the *E. coli* strain DH5α (manufactured by Toyobo Co., Ltd.) was transformed using the thus obtained recombinant plasmid DNA. Plasmid DNA was prepared from each transformant, and its nucleotide sequence was analyzed using BigDye Terminator Cycle Sequencing Ready Reaction Kit v2.0 and the DNA sequencer ABI PRISM 377 (manufactured by Applied Biosystems). As a result, a plasmid pKAN-ATIII for animal cell expression containing a gene sequence of a full translation region of human antithrombin III was obtained (FIG. 5).

4. Stable Introduction of Human Antithrombin III Expression Plasmid into CHO/DG44 Cell Line in which Genomic FUT8 Gene was Double-Knocked Out Transformants were prepared by stably introducing the plasmid pKAN-ATIII prepared in the above item into the CHO/DG44 cell line in which the FUT8 gene was double-knocked out prepared in Example 1. Gene introduction of the plasmid pKAN-ATIII was carried out by the following procedure in accordance with the electroporation [*Cytotechnology*, 3, 133 (1990)]. First, 100 μg of the plasmid pKAN-ATIII was linearized by preparing 600 μl of a reaction mixture containing 60 ηl of NEBuffer 3 (manufactured by New England Biolabs) and 120 unites of a restriction enzyme MluI (manufactured by New England Biolabs) and the digestion reaction was carried out at 37° C. for 5 hours. After the reaction, the reaction mixture was purified by phenol/chloroform extraction treatment and ethanol precipitation to thereby recover the linear plasmid. Next, one cell line among the CHO/DG44 cell clones in which the FUT8 gene was double-knocked out prepared in Example 1 was suspended in a K-PBS buffer (137 mmol/l KCl, 2.7 mmol/l NaCl, 8.1 mmol/l $Na_2HPO_4$, 1.5 mmol/l $KH_2PO_4$, 4.0 mmol/l $MgCl_2$) to prepare a suspension of $8\times10^7$ cells/mi. After 200 μl of the cell suspension ($1.6\times10^6$ cells) was mixed with 9 μg of the above-described linear plasmid, a full volume of the cell-DNA mixture was transferred into Gene Pulser Cuvette (2 mm in inter-electrode distance, manufactured by BIO-RAD), and gene introduction was carried out using an electroporation device Gene Pulser II (manufactured by BIO-RAD) under conditions of 350 V in pulse voltage and 250 μF in electric capacity. After carrying out the gene introduction on 4 cuvettes in the same manner, the cell suspension was suspended in 120 ml of IMDM medium (manufactured by Life Technology) supplemented with 10% fetal bovine serum (manufactured by Life Technology) and 50 μg/ml gentamicin (manufactured by Nacalai Tesque) and inoculated at 100 μl/well into 96-well 12 plates for adherent cells (manufactured by Greiner). The culturing was carried out in a $CO_2$ incubator (manufactured by TABAI) under conditions of 5% $CO_2$ and 37° C.

5. Obtaining of 500 nM MTX-Resistant Cell Line

The cells into which the pKAN-ATIII was stably introduced obtained in the above item were cultured for 6 days, and then the culture supernatants were discarded and the IMDM medium supplemented with 10% dialyzed fetal bovine serum, 50 μg/ml gentamicin and 50 nM methotrexate (MTX) (manufactured by SIGMA) was dispensed at 100 μl/well. The culturing was continued for 9 days while repeating this medium exchanging work at an interval of 3 to 4 days. Next, the culturing was continued for 18 days while repeating the medium exchanging work using the IMDM medium supplemented with 10% dialyzed fetal bovine serum, 50 μg/ml gentamicin and 200 nM MTX at an interval of 3 to 4 days, and the finally formed colonies were inoculated into a 24 well plate (manufactured by SIGMA). Subsequently, the culturing was continued for 19 days while repeating the medium exchanging work using the IMDM medium supplemented with 10% dialyzed fetal bovine serum, 50 μg/ml gentamicin and 500 nM MTX at an interval of 3 to 4 days, optionally expanding the culture, thereby obtaining transformants resistant to 500 nM MTX.

6. Selection of Cell Line Highly Producing Antithrombin III

From each of the several 500 nm MTX-resistant cell lines obtained in the above item, $1.5\times10^6$ cells were collected, suspended in 5 ml of the IMDM medium supplemented with 10% dialyzed fetal bovine serum, 50 μg/ml gentarnicin and 500 nM MTX, and then cultured by inoculating into a tissue culture flask (culturing area 25 $cm^2$, manufactured by Greiner). Three days after the culturing, the culture supernatant was recovered, and the amount of human antithrombin III contained in the supernatant was measured using ELISA for antithrombin (ATIII) kit (manufactured by Affinity Biological). The method was carried out in accordance with the instructions attached to the kit, and a commercially available human plasma-derived antithrombin III (manufactured by SIGMA) was used as the standard preparation. Among the several 500 nM MTX-resistant cell lines, it was confirmed that human antithrombin III is expressed in a concentration of 304 μg/ml in the culture supernatant of a cell line MS705 pKAN-ATIII 27. The cell line MS705 pKAN-ATIII 27 was deposited on Sep. 9, 2003, as FERM BP-08472 in International Patent Organism Depositary, National Institute of Advanced Industrial Science and Technology (Central 6, 1-1, Higashi 1-chome, Tsukuba-shi, Ibaraki, Japan).

EXAMPLE 3

Expression of Recombinant Antithrombin III by CHO/DG44 Cell:

1. Introduction of Human Antithrombin III Expression Plasmid into CHO/DG44 Cell Line First, 100 μg of the plasmid pKAN-ATIII prepared in Example 2-3 was linearized by preparing 600 μl of a reaction mixture containing 60 μl of NEBuffer 3 (manufactured by New England Biolabs) and 120 units of a restriction enzyme MluI (manufactured by New England Biolabs) and the digestion reaction was carried out at 37° C. for 5 hours. After the reaction, the reaction mixture was purified by phenol/chloroform extraction treatment and ethanol precipitation to thereby recover the linear plasmid.

Next, a CHO/DG44 cell line [*Proc. Natl. Acad. Sci. USA*, 77, 4216 (1980)] was suspended in K-PBS buffer (137 mmol/l KCl, 2.7 mmol/l NaCl, 8.1 mmol/l $Na_2HO_4$, 1.5 mmol/l $KH_2PO_4$, 4.0 mmol/l $MgCl_2$) to give a density of $8\times10^7$ cells/ml. Next, 200 μl of the cell suspension ($1.6\times10^6$ cells) was mixed with 9 μg of the above-described linear plasmid, a full volume of the cell-DNA mixture was transferred into Gene Pulser Cuvette (2 mm in inter-electrode distance, manufactured by BIO-RAD), and gene introduction was carried out using an electroporation device Gene Pulser (manufactured by BIO-RAD) under conditions of 350 V in pulse voltage and 250 μF in electric capacity. The electroporation was carried out in accordance with a reference [*Cytotechnology*, 3, 133 (1990)]. After the gene introduction, the cell suspension was suspended in 30 ml of IMDM medium (manufactured by Life Technologies) supplemented with 10% fetal bovine serum (manufactured by Life Technologies) and 50 μg/ml of gentamicin (manufactured by Nacalai Tesque) and inoculated at 100 μl/well into 96-well 3 plates for adherent cells (manufactured by Greiner). The culturing was carried out under conditions of 5% $CO_2$ and 37° C.

2. Obtaining of MTX-Resistant Cell Line

The pKAN-ATIII-introduced cells obtained in the above were cultured for 6 days, and then the culture supernatants were discarded and the IMDM medium supplemented with 10% dialyzed fetal bovine serum, 50 μg/ml gentamicin and 50 nM methotrexate (MTX) (manufactured by SIGMA) was dispensed at 100 μl/well. The culturing was continued for 9 days while repeating this medium exchanging work at an interval of 3 to 4 days. Next, the culturing was continued for 18 days while repeating the medium exchanging work using the IMDM medium supplemented with 10% dialyzed fetal bovine serum, 50 μg/ml gentamicin and 200 nM MTX at an interval of 3 to 4 days, and the finally formed colonies were inoculated into a 24 well plate (manufactured by Greiner). Subsequently, the culturing was continued for 19 days while repeating the medium exchanging work using the IMDM medium supplemented with 10% dialyzed fetal bovine serum, 50 μg/ml gentamicin and 500 nM MTX at an interval of 3 to 4 days, optionally expanding the culture, thereby obtaining transformants resistant to 500 nM MTX.

3. Selection of Cell Line Highly Producing Antithrombin III

From each of the several 500 nm MTX-resistant cell lines obtained in the above item, $1.0\times10^6$ cells were collected, suspended in 5 ml of the IMDM medium supplemented with 10% dialyzed fetal bovine serum, 50 μg/ml gentamicin and 500 nM MTX, and then cultured by inoculating into a tissue culture flask Three days after the culturing, the culture supernatant was recovered, and the amount of recombinant antithrombin III contained in the supernatant was measured using ELISA for antithrombin (ATIII) kit (manufactured by Affinity Biological), and a highly producing cell line was selected from the result. The method was carried out in accordance with the instructions attached to the ELISA kit, and a human plasma-derived preparation Neuart (manufactured by Mitsubishi Pharma Corporation) was used as the standard preparation. A transformant in which accumulation of recombinant human antithrombin III was found in its culture supernatant was named pKAN-ATIII DG44.

EXAMPLE 4

Purification of Recombinant Antithrombin III and Analysis of Sugar Chain Structure:

1. Naturalization to Serum-Free Medium

The recombinant antithrombin M-expressing FUT8 gene-double-knockout cell line and recombinant antithrombin III-expressing CHO/DG44 cell line prepared in Examples 2 and 3 were naturalized to a serum-free medium by the following method. Each cell line was suspended in 15 ml of EX-CELL 302 medium (manufactured by JRH) supplemented with 4 mM of L-glutamine (manufactured by Invitrogen), 50 µg/ml of gentamicin and 500 nM of MTX (hereinafter referred to as serum-free medium) to give a density of $5 \times 10^5$ cells/ml and inoculated into a 125 ml-conical flask to carry out a batch culturing. The culturing was carried out at 35° C. and at a rotation speed of 90 to 100 rpm, and when sub-culturing was carried out, the air in the conical flask was replaced by blowing air containing 5% $CO_2$ onto the medium surface, in a volume of 4-fold or more of the culture vessel volume. Three days thereafter, the medium was exchanged, and sub-culturing was carried out with $5 \times 10^5$ cells/ml on the 6th day. Thereafter, the sub-culturing was repeated at an interval of 3 to 4 days for 2 weeks to naturalize the cells to the serum-free medium. By this culturing, a transformant pKAN-ATIII AFMS705 derived from the FUT8 gene-double-knockout cell line and having the ability to grow in the serum-free medium and a transformant pKAN-ATIII AFDG44 derived from the CHO/DG44 cell line and having the ability to grow in the serum-free medium were obtained. Each of the thus obtained cell lines was suspended in 15 ml of the serum-free medium to give a density of $3.0 \times 10^5$ cells/ml and cultured by inoculating into a 125 ml flask. Three days after the culturing, the culture supernatant was recovered, and the amount of recombinant antithrombin III contained in the supernatant was measured using ELISA for antithrombin (ATIII) kit (manufactured by Affinity Biological) to confirm that the recombinant antithrombin III was expressed by both of the transformants in almost the same concentration, namely 18 µg/ml in the culture supernatant of pKAN-ATIII AFMS705 and 28 µg/ml in the culture supernatant of pKAN-ATIII AFDG44. In this connection, the cell line pKAN-ATIII AFMS705 was deposited as a cell line name pKAN-ATIII AFMS705 on Aug. 10, 2004, as FERM BP-10088 in International Patent Organism Depositary, National Institute of Advanced Industrial Science and Technology (Central 6, 1-1, Higashi 1-chome, Tsukuba-shi, Ibaraki, Japan).

2. Obtaining of Culture Supernatant Containing Recombinant Antithrombin III

Each of the cell lines pKAN-ATIII AFMS705 and pKAN-ATIII AFDG44 obtained in the above as two serum-free-naturalized cell lines was suspended in 450 ml of the serum-free medium to give a density of $3 \times 10^5$ cells/ml and inoculated into a 2 liter capacity roller bottle (manufactured by Becton Dickinson), and the air in the conical flask was replaced by blowing air containing 5% $CO_2$ onto the medium surface, in a volume of 4-fold or more of the culture vessel volume. The culturing was carried out at 35° C. and at a rotation speed of 5 to 10 rpm, and 37.5 ml of a feed medium and 1.8 ml of 50% glucose solution were added thereto on the 5th day of the culturing for the purpose of supplementing for consumed nutrient substances such as amino acids. The feed medium is a medium comprising amino acids (L-alanine 0.22 g/l, L-arginine monohydrochloride 0.74 g/l, L-asparagine monohydrate 0.22 g/l, L-aspartic acid 0.26 g/l, L-cystine dihydrochloride 0.80 g/l, L-glutamic acid 0.66 g/l, L-glutamine 7.3 g/l, glycine 0.26 g/l, L-histidine monohydrochloride dihydrate 0.37 g/l, L-isoleucine 0.92 g/l, L-leucine 0.92 g/l, L-lysine monohydrochloride 1.29 g/l, L-methionine 0.26 g/l, L-phenylalanine 0.58 g/l, L-proline 0.35 g/l, L-serine 0 37 g/l, L-threonine 0.84 g/l, L-tryptophan 0.14 g/l, L-tyrosine disodium dihydrate 0.92 g/l and L-valine 0.83 g/l), vitamins (d-biotin 0.0001 g/l, calcium D-pantothenate 0.035 g/l, choline chloride 0.035 g/l, folic acid 0.035 g/l, myo-inositol 0.063 g/l, niacin amide 0.035 g/l, pyridoxal hydrochloride 0.035 g/l, riboflavin 0.0035 g/l, thiamine hydrochloride 0.035 g/l and cyanocobalamin 0.0001 g/l), recombinant human insulin 0.31 g/l (manufactured by JRH), ethanolamine 0.025 g/l (manufactured by Sigma-Aldrich), 2-mercaptoehtanol 0.0098 g/l (manufactured by Sigma-Aldrich), a soybean hydrolysate HY-SOY 8 g/l (manufactured by Quest International), sodium selenite 16.8 µg/l (manufactured by Sigma-Aldrich), cholesterol lipid concentrated solution 2 ml/l (250× aqueous solution, manufactured by Invitrogen) and ferric ethylenediaminetetraacetate sodium salt 0.05 g/l (manufactured by Sigma-Aldrich). In and after the feeding, air replacement by aeration was carried out every day until completion of the culturing. By keeping 80% or more of the survival ratio, the culturing was carried out for 9 to 10 days. After completion of the culturing, the amount of recombinant human antithrombin in the culture supernatant was measured using ELISA for antithrombin (ATIII) kit (manufactured by Affinity Biological). As a result, it was confirmed that the recombinant antithrombin III is contained in the culture supernatants of pKAN-ATIII AFMS705 and pKAN-ATIII AFDG44 in respective concentrations of 68 µg/ml and 87 µg/ml. Hereinafter, the recombinant antithrombin III produced by pKAN-ATIII AFMS705 is referred to as ATIII MS705, and the recombinant antithrombin in produced by pKAN-ATIII AFDG44 as ATIII DG44, respectively.

3. Purification of Recombinant Antithrombin III

Figure 7:
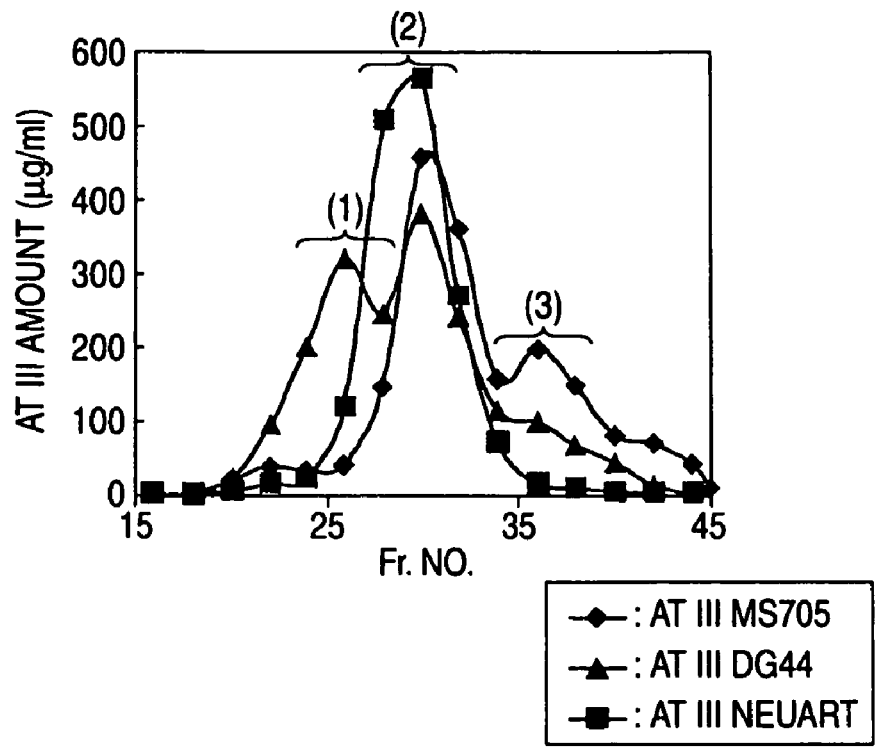
FIG. 7 shows elution pattern of antithrombin III by heparin affinity chromatography.

Recombinant antithrombin III was purified in the following manner from the culture supernatant containing recombinant antithrombin III, obtained in the above item, in accordance with the method described in a reference [*Meth. Enzymol.*, 222, 525, 1993]. A portion of the culture supernatant containing recombinant antithrombin III obtained in the above item, corresponding to approximately 250 mg of the recombinant antithrombin III, was applied to a heparin column (Heparin Sepharose 6 Fast Flow, 250 ml, manufactured by Amersham Bioscience) which had been equilibrated with a buffer solution consisting of 50 mM Tris, 14 mM citric acid and 0.15 M NaCl (pH 7.4). Subsequently, the heparin column was washed with 10 CV of the equilibration buffer, and then the recombinant antithrombin III was eluted using a linear gradient elution method (12 CV) up to 3 M NaCl concentration. The equipment used was Hiload Chromatography System (manufactured by Amersham Bioscience), the flow rate was 21 ml/min, and the recombinant human antithrombin III elution fractions were fractionated at 50 ml. When the amount of human antithrombin III in each fraction was measured using ELISA for antithrombin(ATIII) kit (manufactured by Affinity Biological), roughly dividing three peaks were observed in the elution pattern as shown in FIG. 7, and ATIII MS705 and ATIII DG44 showed different elution patterns. In the following, these are called peak (1) fraction, peak (2) fraction and peak (3) fraction in that order starting from the most quickly eluted fraction. It has been reported that plurality of peaks were found when antithrombin III was purified by heparin affinity chromatography in the following literatures [e.g., *J. Biol. Chem.*, 268, 17588 (1993), *Biochem. J.*, 286, 793 (1992), *J. Biol. Chem.*, 264, 21153 (1989), etc.). In addition, when elution pattern of Neuart was examined, its elution was observed limiting to the peak (2) fraction. Each of the main peak fractions corresponding to ATIII MS705 peak (2) fraction and peak (3) fraction, and ATIII DG44 peak (1) fraction and peak (2) fraction was desalted with 5 mM sodium phosphate buffer (pH 7.4) by a dia-filtration method using Pericon XL (manufactured by Millipore) and Biomax 10 (manufactured by Millipore). Each of the thus desalted peak fractions was applied to DEAE Sepharose Fast Flow Column (manufactured by Amersham, 480 ml) and adsorbed thereto. Subsequently, the column was washed with 12 CV of 20 mM sodium phosphate buffer (pH 7.4), and then the recombinant antithrombin III was eluted at a flow rate of 40 ml/min using a linear gradient elution method (8.6 CV) up to 1.0 M NaCl concentration. The elution pattern was measured by its absorbance (A280 nm). Next, the elution fractions containing recombinant antithrombin III were combined, and the buffer solution was replaced by PBS by a dia-filtration method using Pericon XL (manufactured by Millipore) and Biomax 10 (manufactured by Millipore), thereby preparing samples for evaluation. By measuring absorbance (A280 nm) of the samples for evaluation, the protein concentration was calculated based on A280 nm 1.0=0.64 mg/ml. In addition, determination using ELISA for antithrombin(ATIII) kit (manufactured by Affinity Biological) was also carried out to confirm that the concentration was identical by the absorbance method and the ELISA method. Also, reduction SDS-PAGE was carried out using PAGEL SPG520L (manufactured by Atto). In the electrophoresis, 2 μg of recombinant antithrombin III reduced with 2-mercaptoethanol was used, and the staining was carried out by CBB staining. As a result, bands other than the ATIII band of approximately 60 kD in molecular weight were not confirmed in all of the samples for evaluation.

Figure 2:
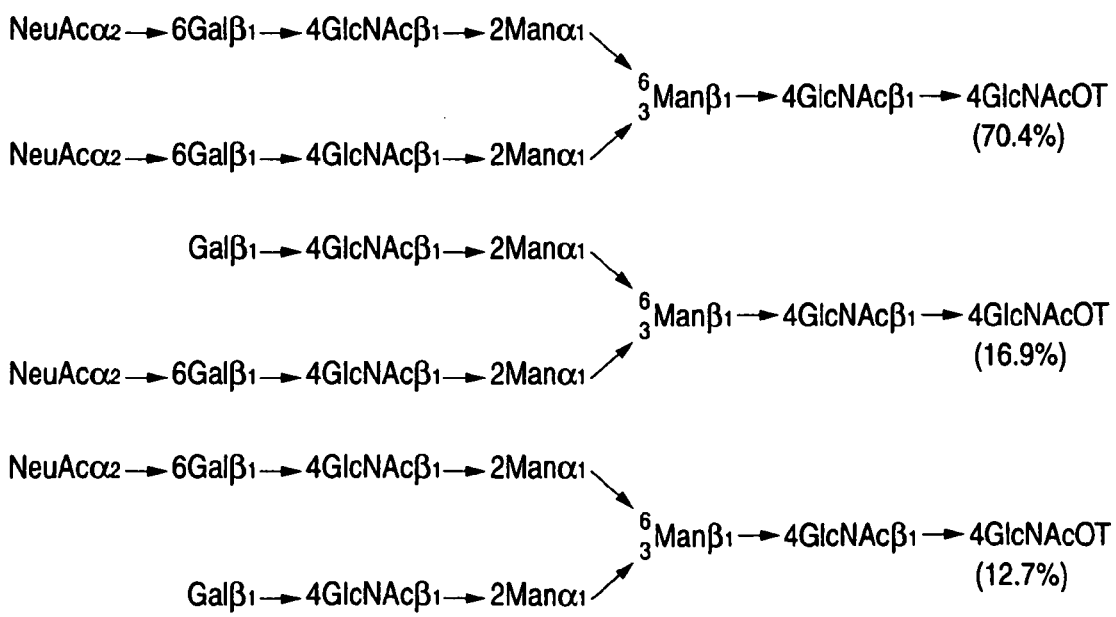
FIG. 2 schematically shows complex type N-glycoside-linked sugar chains added to human plasma-derived antithrombin III.

4. Composition Analysis of Recombinant Antithrombin III Neutral Sugar and Amino Sugar The compositions of neutral sugar and amino sugar were analyzed on the samples for evaluation obtained in Example 4-3. Each of the recombinant antithrombin III evaluation samples was hydrolyzed at 100° C. for 2 hours in the presence of 4.0 mo/l trifluoroacetic acid to release neutral sugars and amino sugars from the protein. The thus released sugars were analyzed using DX-500 sugar analyzer (manufactured by Dionex) with reference to the method described in the literature of Michael Weitzhandler et al. [*Analytical Biochemistry*, 241, 128-134 (1996)] and DIONEX Application Note 92 (The Determination of Sugars in Molasses by High-Performance Anion Exchange with Pulsed Amperometric Detection). It is known that the sugar chain structure of human plasma-derived antithrombin III is a complex type double-strand sugar chain which does not contain fucose [*Arch. Biochem. Biophys.*, 203 458 (1980)] (FIG. 2). In the analysis of the results of neutral sugar and amino sugar composition analysis, compositional ratios of respective monosaccharide components (fucose, galactose and mannose) were calculated by regarding the compositional ratio of N-acetylglucosamine as 4. As a result of the analysis, fucose was detected in the sugar chain components of ATIII DG44, while the fucose content in the sugar chain components of ATIII MS705 was the detection limit or less, similar to the case of Neuart which is a human plasma-derived antithrombin III. In addition, based on the compositional ratios of respective monosaccharide components, it was suggested that the main sugar chain structure of all samples is not a high mannose type or hybrid type but a complex type double-strand sugar chain.

5. Hydroxyapatite Chromatography Analysis

The α type and β type compositional ratio of the samples for evaluation obtained in Example 4-3 was analyzed by hydroxyapatite chromatography, with reference to the method of Goran Karlsson and Stefan Winge [*Protein Expression and Purification*, 28, 196-201 (2003)]. As a result, similar to the case of the human plasma-derived Neuart, the α type was mainly contained in the ATIII MS705 peak (2) fraction and ATIII DG44 peak (1) fraction. Also, the α type and β type were contained in the ATIII DG44 peak (2) fraction at almost the same ratio. Results of the neutral sugar and amino sugar analysis and hydroxyapatite chromatography analysis are summarized in Table 1.

TABLE 1

|  | Sugar chain structure | Fucose | Main molecular type |
|---|---|---|---|
| ATIII MS705 peak (2) | complex type double-strand | − | α |
| ATIII MS705 peak (3) | complex type double-strand | − | β |
| ATIII DG44 peak (1) | complex type double-strand | + | α |
| ATIII DG44 peak (2) | complex type double-strand | + | α & β |
| Neuart | complex type double-strand | − | α |

Since ATIII DG44 contained fucose in the sugar chain, its sugar chain structure was different from that of the human plasma-derived antithrombin III. On the other hand, it was found that sugar chain structures of the ATIII MS705 peak (2) fraction and ATIII MS705 peak (3) fraction are sugar chain structures close to the human plasma-derived α type and β type antithrombin III, respectively In addition, it was able to separate the α type and β type of ATIII MS705 by a heparin affinity-aided purification method as reported in a reference [*J. Biol. Chem.*, 268, 17588 (1993)] on human plasma-derived antithrombin III. However, it was not able to separate the ATIII DG44 peak (2) fraction when the same purification was carried out. Based on the above, it was revealed that the ATIII MS705 has properties equivalent to those of the human plasma-derived antithrombin III.

EXAMPLE 5

Comparison of Biological Activities of Purified Recombinant Antithrombin III Samples:

1. Measurement of Heparin Dissociation Constant

Since the three-dimensional structure of antithrombin III molecule changes by the binding of antithrombin III with heparin, the heparin dissociation constant can be measured making use of the change in fluorescence intensity of the tryptophan residue constituting the antithrombin III protein. The following equation 1) is formed between the antithrombin III concentration and the thrombin concentration (*Meth. Enzymol.*, 222, 525, 1993).

$$\frac{\Delta F}{F_0} = \frac{\Delta F\max}{F_0} \times \frac{[AT]_0 + n[H]_0 + Kd - \{([AT]_0 + n[H]_0 + Kd)^2 - 4n[AT]_0[H]_0\}^{1/2}}{2[AT]_0} \quad \text{Equation 1)}$$

ΔF: change in quantity of fluorescence
ΔFmax: maximum change in quantity of fluorescence
$F_0$: fluorescence intensity at the time of no heparin addition
$[AT]_0$: antithrombin III concentration
$[H]_0$: heparin concentration
Kd: dissociation constant
n: stoichiometry The heparin dissociation constant of each of the heparin affinity-fractionated samples for antithrombin III evaluation use obtained in Example 4-3 was measured by the following method. First, a buffer solution (pH 7.4) comprising 20 mM $Na_2HPO_4$, 0.1 M NaCl, 0.1 mM EDTA.2$H_2O$ and 0.1% PEG 6000 was prepared. This buffer solution was used in diluting the samples. From 0 to 20 equivalents of heparin (manufactured by SIGMA) was added to 50 nM of antithrombin III, and the fluorescence intensity of each solution was measured at an excitation wavelength of 280 nm and a fluorescence wavelength of 340 nm. The dissociation constant was analyzed by an analyzing software GraphPad prism 4 (manufactured by Graphpad) using the equation 1). Results of the measurement of heparin dissociation constant (Kd value, unit nM) of samples for evaluation obtained in Example 4-3 are shown in Table 2. The binding strength of ATIII to heparin becomes strong as the Kd value becomes small. Thus, the ATIII MS705 peak (3) fraction showed the largest binding strength, followed by the ATIII MS705 peak (2) fraction and the ATIII DG44 peak (2) fraction, and the ATIII DG44 peak (1) fraction showed the weakest binding strength.

TABLE 2

| | Kd (nM) |
|---|---|
| ATIII MS705 peak (2) | 9.87 ± 1.09 |
| ATIII MS705 peak (3) | 3.06 ± 0.07 |
| ATIII DG44 peak (1) | 59.71 ± 2.11 |
| ATIII DG44 peak (2) | 9.84 ± 0.97 |
| Neuart | 20.09 ± 3.60 |

2. Measurement of Heparin Cofactor Activity

It is known that thrombin inhibition rate of antithrombin III considerably increases in the presence of heparin. Also, the binding reaction of thrombin with antithrombin III occurs at a molar ratio of 1:1, and they mutually lose their activities after the reaction, so that antithrombin reaction of the antithrombin completes within a markedly short period of time in the presence of heparin. The heparin cofactor activity is represented by the residual thrombin activity at the time of the completion of the antithrombin reaction, or in other words, the heparin cofactor activity can measure the amount of the activated antithrombin III at the time of the completion of the antithrombin reaction [*Zoku Iyakuhin No Kaihatsu (A Sequel to Medicines, Continued)*, 20, 185 (1992)].

Figure 8:
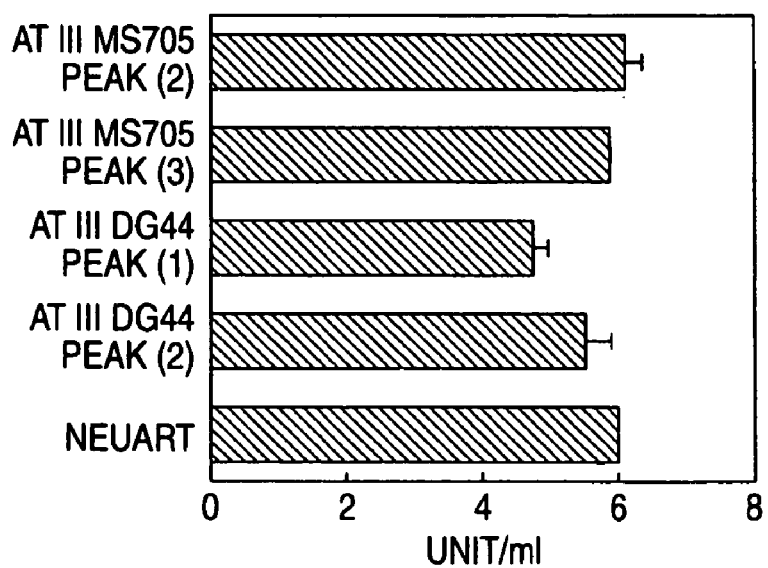
FIG. 8 shows heparin cofactor activity of antithrombin III.

In order to measure the heparin cofactor activity, a buffer solution (pH 8.3) consisting of 0.15 M NaCl, 0 05 M Tris-HCl and 0.2% albumin was firstly prepared. This buffer solution was used in diluting samples and preparing an enzyme solution. To an antithrombin III solution, 1.0 ml of an enzyme solution comprising 2.5 units/ml of thrombin (manufactured by Enzyme Research Laboratories) and 0.6 unit/ml of heparin (manufactured by SIGMA) was added, followed by reaction at 37° C. for 5 minutes. Subsequently, 100 μl of 2.0 mM S-2238 (manufactured by Dauichi Pure Chemicals) as a specific substrate of thrombin was added thereto and allowed to develop color for 2 minutes, and then the reaction was stopped with 50% acetic acid. The residual thrombin activity was calculated from the absorbance (A405 nm) of p-nitroaniline formed by the degradation of S-2238 in the reaction mixture. In this case, antithrombin III was used in the measurement by diluting it within the range of 0.15 to 4 μg/ml. Neuart was used as the standard substance for the preparation of a calibration curve, and the heparin cofactor activity was calculated as the activity (unit/ml) per unit volume (liquid volume). The heparin cofactor activity in each of the samples for evaluation obtained in Example 4-3 was measured, and the obtained activity values were expressed by the activity (unit/g) per unit mass, with the results shown in FIG. 8. The peak fraction (2) of ATIII MS705 and peak fraction (3) of ATIII MS705 showed similar activity to that of the human plasma-derived preparation Neuart (manufactured by Mitsubishi Pharma Corporation), but the ATIII DG44 peak fraction (1) and ATIII DG44 peak fraction (2) showed lower values than that of Neuart.

3. Measurement of Thrombin Inhibition Secondary Rate Constant in the Absence of Heparin The thrombin inhibition secondary rate constant was measured in accordance with a reference (*J. Biol. Chem.*, 277, 24460 (2002)).

Thrombin inhibition reaction of ATIII in the absence of heparin can be considered by approximating to a pseudo-primary reaction under conditions in which antithrombin III is present in an excess amount based on the amount of thrombin, so that the following equation 2) is formed.

$$\ln [T]_t = -kobs \cdot t + \ln [T]_0 \quad \text{Equation 2)}$$

$[T]_t$: thrombin concentration after t hour
$[T]_0$: initial concentration of thrombin
kobs: pseudo-primary rate constant
t: time $$kobs = k[AT] \quad \text{Equation 3)}$$

k: secondary rate constant
[AT]: antithrombin III concentration

Accordingly, in order to measure the thrombin inhibition secondary rate constant, a buffer solution (pH 7.4) comprising 20 mM $Na_2HPO_4$, 0.1 M NaCl, 0.1 mM EDTA.2$H_2O$ and 0.1% PEG 8000 was firstly prepared. This buffer solution was used in diluting samples and preparing an enzyme solution. An enzyme solution comprising 100 nM antithrombin III and 10 nM thrombin was prepared and allowed to react at 25° C. for a period of 1 to 40 minutes. At each period, 100 μl of 0.15 mM S-2238 (manufactured by Dauichi Pure Chemicals) as a specific substrate of thrombin was added thereto, and the absorbance (A405 nm) for approximately 2 minutes was measured. The residual thrombin concentration was calculated from the change in absorbance at each period, and the pseudo-primary rate constant was calculated using the above-described equation 2). In addition, thrombin inhibition secondary rate constant (unit/M/second) in the absence of heparin was calculated using the above-described formula 3). The secondary rate constant of the samples for evaluation obtained in Example 4-3 is shown in Table 3. S.D. represents standard deviation.

Regarding the thrombin inhibition secondary rate constant in the absence of heparin, the ATIII DG44 peak (1) fraction showed a slightly low value, but all of the other samples for evaluation showed similar activity to that of the human plasma-derived antithrombin III Neuart.

TABLE 3

|  | Secondary rate constant (−hep) | |
| --- | --- | --- |
|  | /M/sec | S.D. |
| ATIII MS705 peak (2) | 8.5E+03 | 1.9E+02 |
| ATIII MS705 peak (3) | 8.8E+03 | 3.7E+02 |
| ATIII DG44 peak (1) | 7.7E+03 | 1.8E+02 |
| ATIII DG44 peak (2) | 8.6E+03 | 1.6E+02 |
| Neuart | 8.2E+03 | 8.8E+01 |

4. Measurement of Thrombin Inhibition Secondary Rate Constant in the Presence of Heparin The thrombin inhibition secondary rate constant of the samples for evaluation obtained in Example 4-3, in the presence of heparin, was measured by the following method in accordance with a reference [Biochem. J., 286, 793 (1992)]. Firstly, a buffer solution (pH 7.4) comprising 20 mM $Na_2HPO_4$, 0.1 M NaCl, 0.1 mM $EDTA \cdot 2H_2O$ and 0.1% PEG 8000 was prepared. This buffer solution was used in diluting samples and preparing an enzyme solution. An enzyme solution comprising 0.5 to 1 nM of thrombin and 5 to 25 pM of heparin (manufactured by SIGMA) was added to 100 nM of antithrombin III, followed by reaction at 25° C. for 1 to 30 minutes, and then 100 μl of 0.15 mM S-2238 (manufactured by Daiichi Pure Chemicals) as a specific substrate of thrombin was added thereto, and the absorbance (A405 nm) for approximately 2 minutes was measured. The residual thrombin concentration was calculated from the change in absorbance at each period, and the pseudo-primary rate constant was calculated using the above-described equation 2). In addition, the thrombin inhibition secondary rate constant in the presence of heparin was calculated using the following equation 4).

$$k_{obs} = k * [H]_0 * \frac{[AT]_0}{Kd + [AT]_0} + k_{uncot} * [AT]_0 \quad \text{Equation 4)}$$

kobs: pseudo-primary rate constant
k: secondary rate constant
$[H]_0$: concentration of heparin
Kd: heparin dissociation constant
$[AT]_0$: antithrombin III concentration
$k_{uncal}$: secondary rate constant in the absence of heparin The thrombin inhibition secondary rate constant (unit/M/sec) of the samples for evaluation obtained in Example 4-3, in the presence of heparin, was measured, with the results shown in Table 4. Regarding the numerical values, for example, 2.5 E+07 means $2.5 \times 10^7$. Also, S.D. means standard deviation. Regarding the secondary rate constant, the peak (2) fraction of ATIII MS705 and peak (3) fraction of ATIII MS705 showed similar activity to that of Neuart, but the ATIII DG44 peak (1) fraction showed a considerably low value, and the ATIII DG44 peak (2) fraction also showed a slightly lower value. Based on this result, it was found that a fraction having low antithrombin activity in the presence of heparin is contained in the recombinant antithrombin III produced by using the CHO/DG44 cell line. On the other hand, it was found that a fraction mainly showing similar activity to that of the human plasma-derived antithrombin III is obtained from the recombinant antithrombin III produced by using the FUT8 gene-double-knockout cell line.

TABLE 4

|  | Secondary rate constant (+hep) | |
| --- | --- | --- |
|  | /M/sec | S.D. |
| ATIII MS705 peak (2) | 2.5E+07 | 1.6E+06 |
| ATIII MS705 peak (3) | 2.6E+07 | 8.7E+05 |
| ATIII DG44 peak (1) | 8.7E+06 | 1.1E+04 |
| ATIII DG44 peak (2) | 2.0E+07 | 8.1E+05 |
| Neuart | 2.3E+07 | 2.9E+05 |

As a result of the analyses in Examples 4 and 5, it was shown that the recombinant antithrombin III produced by the FUT8 gene-double-knockout cell line is a protein having similar properties to those of the human plasma-derived antithrombin III, in terms of the sugar chain structures and biological activities, in comparison with the recombinant antithrombin III produced by the CHO/DG44 cell line. From this result, it was shown that the recombinant antithrombin III produced by the FUT8 gene-double-knockout cell line is suitable as a substitute for the human plasma-derived antithrombin III.

EXAMPLE 6

Expression of Amino Acid-Modified Recombinant Antithrombin III in FUT8 Gene-Double-Knockout Cell:

An FUT8 gene-double-knockout cell capable of expressing a mutation type human antithrombin III (hereinafter referred to as "ATIIIN135Q"), in which asparagine residue at the 135th position counting from the N-terminal of mature type human antithrombin III was substituted with a glutamine residue, was prepared by the method shown below. In this connection, since the ATIIIN135Q composition has 3 addition sites for N-binding type sugar chains, all of the expressed recombinant antithrombin III become the β-type.

1. Preparation of Plasmid pBS-ATIIIN135Q

Figure 6:
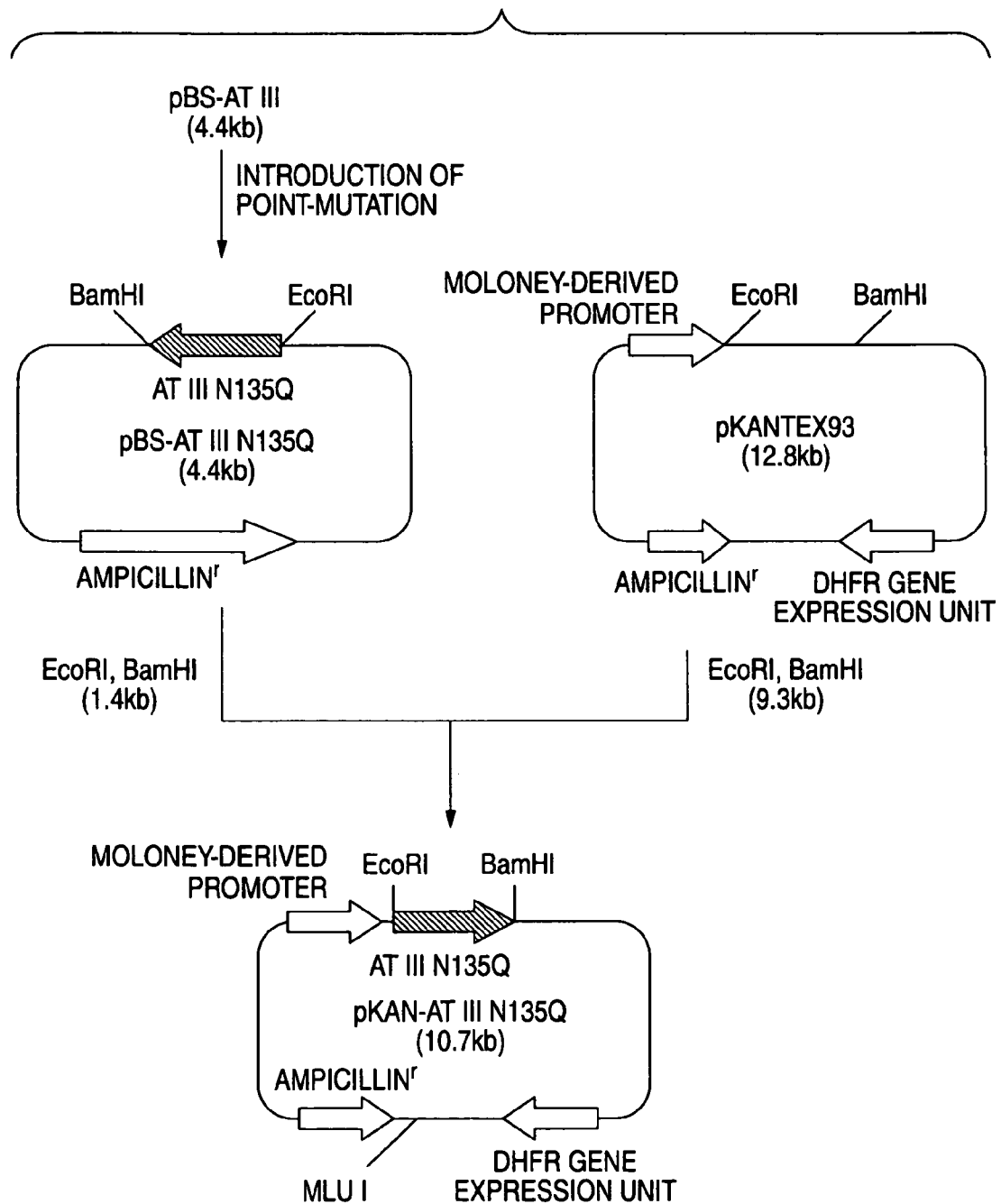
FIG. 6 shows the steps for constructing plasmid pKAN-ATIIIN135Q.

Firstly, two oligo DNA primers for site-directed mutagenesis (SEQ ID NOs:30 and 31) for replacing the 167th asparagine residue counting from the N-terminal to a glutamine residue were prepared for the antithrombin III gene sequence (UniGene: Hs.75599, SEQ ID NO:1). Using the pBS-ATIII prepared in Example 2-2 as the template, site-directed mutagenesis was applied to the antithrombin III cDNA sequence using the above-described primers and Quick Change® Site-Directed Mutagenesis Kit (manufactured by STRATAGENE). The method was carried out in accordance with the manual attached to the hit. Plasmid DNA samples were prepared front the thus obtained transformants using QIAprep® Spin Miniprep Kit (manufactured by QIAGEN), and their nucleotide sequences were analyzed using BigDye Terminator Cycle Sequencing Ready Reaction Kit v2.0 (manufactured by Applied Biosystems) and a DNA sequencer ABI PRISM 377 (manufactured by Applied Biosystems). As a result, a plasmid pBS-ATIIIN135Q comprising a cDNA sequence of a full translation region of a mutation type antithrombin III (ATIIIN135Q) was obtained (FIG. 6).

2. Preparation of Expression Vector pKAN-ATIIIN135Q

In 17 μl of sterile water, 3 μg of the pBS-ATIIIN135Q prepared in the above was dissolved, 10 units of EcoRI (manufactured by Takara Bio), 10 units of BamHI (manufactured by Takara Bio) and 2 μl of 10× H buffer were added thereto to prepare 20 μl of a reaction mixture, and then the digestion reaction was carried out at 37° C. for 16 hours. Next, 3 μg of a plasmid pKANTEX93 (described in WO97/10354) was dissolved in 17.5 μl of sterile water. By adding 10 units of EcoRI and 2 μl of 10× H buffer to the solution, 20 μl of a reaction mixture was prepared to carry out the digestion reaction at 37° C. for 16 hours. After the reaction, phenol/chloroform extraction treatment and ethanol precipitation were carried out, and the recovered plasmid was dissolved in 17.5 μl of sterile water. By further adding 10 units of BamHI and 2 μl of 10× K buffer to the solution, 20 μl of a reaction mixture was prepared to carry out the digestion reaction at 37° C. for 16 hours. The pBS-ATIIIN135Q fragment (EcoRI-BamHI) and pKANTEX93 fragment (EcoRI-BamHI) obtained in the above were subjected to 1.5% (w/v) agarose gel electrophoresis, and approximately 1.4 kbp and 9.0 kbp of DNA fragments were respectively purified using QIAquick Gel Extraction Kit (manufactured by QIAGEN). Next, 20 μl of a reaction mixture containing 50 ng of the purified pBS-ATIIIN135Q fragment (EcoRI-BamHI), 30 ng of the purified pKANTEX93 fragment (EcoRI-BamHI) and Ligation High (manufactured by Toyobo Co., Ltd.) was prepared, and the ligation reaction was carried out at 16° C. for 16 hours. Using the thus obtained plasmid DNA, an *E. coli* strain DH5α (manufactured by Toyobo Co., Ltd.) was transformed. By preparing a plasmid DNA from the resulting transformant using QIAprep® Spin Miniprep Kit (manufactured by QIAGEN), a mutation type AT antithrombin III expression plasmid for animal cell, pKAN-ATIIIN135Q, was obtained (FIG. 6).

3. Introduction of ATIIIN135Q Expression Plasmid into FUT8 Gene-double-knockout Cell The plasmid pKAN-ATIIIN135Q prepared in Example 6-2 was stably introduced into the FUT8 gene-double-knockout cell prepared in Example 1. The gene introduction was carried out by the following procedure in accordance with the electroporation method [*Cytotechnology*, 3, 133 (1990)]. Firstly, 30 μg of the plasmid pKAN-ATIIIN135Q was linearized by preparing 200 μl of a reaction mixture containing 20 μl of NEBuffer 3 (manufactured by New England Biolabs) and 100 unites of a restriction enzyme MluI (manufactured by New England Biolabs) and the digestion reaction was carried out at 37° C. for 16 hours. After the reaction, the reaction mixture was purified by phenol/chloroform extraction treatment and ethanol precipitation to thereby recover the linear plasmid. Next, the FUT8 gene-double-knockout cell obtained in Example 1 was suspended in a K-PBS buffer (137 mmol/l KCl, 2.7 mmol/l NaCl, 8.1 mmol/l $Na_2HPO_4$, 1.5 mmol/l $KH_2PO_4$, 4.0 mmol/l $MgCl_2$) to prepare a suspension of $8 \times 10^7$ cells/ml. After 200 μl of the cell suspension (1.6×106 cells) was mixed with 9 μg of the above-described linear plasmid, a full volume of the cell-DNA mixture was transferred into Gene Pulser Cuvette (2 mm in inter-electrode distance, manufactured by BIO-RAD), and gene introduction was carried out using an electroporation device Gene Pulser II (manufactured by BIO-RAD) under conditions of 350 V in pulse voltage and 250 μF in electric capacity. After carrying out the gene introduction, the cell suspension was suspended in 30 ml of IMDM medium (manufactured by Life Technologies) supplemented with 10% (v/v) fetal bovine serum (manufactured by Life Technologies) and 50 μg/ml of gentamicin (manufactured by Nacalai Tesque) and inoculated at 100 μl/well into 96-well 3 plates for adherent cells (manufactured by Greiner). The culturing was carried out under conditions of 5% $CO_2$ and 37° C.

4. Obtaining of MTX-Resistant Cell Line

The pKAN-ATIIIN135Q-introduced cells obtained in the above item were cultured for 6 days, and then the culture supernatants were discarded and the IMDM medium supplemented with 10% dialyzed fetal bovine serum, 50 μg/ml gentamicin and 50 nM methotrexate (MTX) (manufactured by SIGMA) was dispensed at 100 μl/well. The culturing was continued for 9 days while repeating this medium exchanging work at an interval of 3 to 4 days. Next, the culturing was continued for 18 days while repeating the medium exchanging work using the IMDM medium supplemented with 10% dialyzed fetal bovine serum, 50 μg/ml gentamicin and 200 nM MTX at an interval of 3 to 4 days, and the finally formed colonies were inoculated into a 24 well plate (manufactured by SIGMA). Subsequently, the culturing was continued for 19 days while repeating the medium exchanging work using the IMDM medium supplemented with 10% dialyzed fetal bovine serum, 50 μg/md gentamicin and 500 nM MTX at an interval of 3 to 4 days, optionally expanding the process, thereby obtaining transformants resistant to 500 nM MTX.

5. Selection of Cell Line Highly Producing ATIIIN135Q

From each of the several 500 nm MTX-resistant cell lines obtained in the above item, $1.0 \times 10^6$ cells were collected, suspended in 5 ml of the IMDM medium supplemented with 10% dialyzed fetal bovine serum, 50 μg/ml gentamicin and 500 nM MTX, and then cultured by inoculating into a tissue culture flask (manufactured by Greiner). Three days after the culturing, the culture supernatant was recovered, and the amount of ATIIIN135Q contained in the supernatant was measured using ELISA for antithrombin (ATIII) kit (manufactured by Affinity Biological), to select a highly producing cell line. The method was carried out in accordance with the manual attached to the ELISA kit, and Neuart (manufactured by Mitsubishi Pharma Corporation) was used as the standard preparation.

6. Naturalization to Serum-Free Medium

The ATIIIN135Q-expressing FUT8 gene-double-knockout cell line prepared in the above item was naturalized to a serum-free medium in the same manner as in Example 4-1. The cell line was suspended in 15 ml of the serum-free medium described in Example 4-1 to give a density of $5 \times 10^5$ cells/ml and inoculated into a 125 ml-conical flask (manufactured by Coming) to carry out batch culturing The culturing was carried out at 35° C. and at a rotation speed of 90 to 100 rpm, and when sub-culturing was carried out, the air in the conical flask was replaced by blowing air containing 5% $CO_2$ onto the medium surface, in a volume of 4-folds or more of the culture vessel volume. The medium was exchanged 3 days thereafter, and sub-culturing was carried out at an inoculation density of $5 \times 10^5$ cells/ml on the 6th day Thereafter, the sub-culturing was repeated at an interval of 3 to 4 days for 2 weeks to neutralize the cells to the serum-free medium. By this culturing, a cell line pKAN-ATIIIN135Q AFMS705 which can grow in the serum-free medium and does not cause aggregation was obtained. The thus obtained cell line was suspended in 15 ml of the serum-free medium to give a density of $3.0 \times 10^5$ cells/ml and cultured by inoculating into a 125 ml capacity flask. Three days after the culturing, the culture supernatant was recovered, and the amount of recombinant antithrombin III contained in the supernatant was measured using ELISA for antithrombin (ATIII) kit (manufactured by Affinity Biological) to confirm that it was expressed in a concentration of 6 μg/ml in the culture supernatant. In this connection, the cell line pKAN-ATIIIN135Q AFMS705 was deposited as a cell line name pKAN-ATIIIN135Q AFMS705 on Aug. 10, 2004, as FERM BP-10089 in International Patent Organism Depositary, National Institute of Advanced Industrial Science and Technology (Central 6, 1-1, Higashi 1-chome, Tsukuba-shi, Ibaraki, Japan).

Thereafter, a mutation type recombinant antithrombin III having a complex type sugar chain in which fucose is not bound to N-acetylglucosamine in the reducing end was obtained by the method described in Example 4, and it was confirmed that the number of the complex type N-glycoside-linked sugar chains was three. In addition, as a result of measuring biological activities of the antithrombin III by the method described in Example 5, it was confirmed that the heparin dissociation constant is significantly smaller and that the heparin cofactor activity and the thrombin inhibition secondary rate constant are significantly higher, than those of the mutation type recombinant antithrombin III expressed by the CHO/DG44 cell.

EXAMPLE 7

Obtaining of Cell Line which Does Not Express Gene of an Enzyme Capable of Catalyzing Dehydrogenation to Convert GDP-mannose into GDP-4-keto,6-deoxy-GDP-mannose:

1. Obtaining of Lectin-Resistant CHO/DG44 Cell Line

The CHO/DG44 cell (*Proc. Natl. Acad. Sci. USA*, 77, 4216 (1980)) was cultured in an IMDM-FBS(10)-HT(1) medium [IMDM medium (manufactured by Invitrogen) containing 10% fetal bovine serum (FBS) (manufactured by Invitrogen) and 1× concentration of HT supplement (manufactured by Invitrogen)] using a 75 $cm^2$ flask for adherent culture (manufactured by Greiner), and allowed to proliferate until reaching just before the confluent stage. After washing the cells with 5 ml of Dulbecco PBS (hereinafter referred to as PBS) (manufactured by Invitrogen), 1.5 ml of 0.05% trypsin (manufactured by Invitrogen) diluted with PBS was added thereto and the cells were allowed to stand at 37° C. for 5 minutes to peal off them from the culture container bottom. The pealed cells were recovered by a centrifugation operation generally carried out in cell culturing and suspended to give a density of $1\times10^5$ cells/ml by adding the IMDM-FBS(10)-HT(1) medium, and then 0.1 μg/ml of an alkylation agent, MNNG (manufactured by SIGMA), was added or not added thereto. After allowing the cells to stand at 37° C. for 3 days in a $CO_2$ incubator (manufactured by TABAI), the culture supernatant was discarded, and the cells were washed, peeled off, recovered and suspended in the IMDM-FBS(10)-HT(1) medium, in the similar manner as described above, and then inoculated into a 96-well plate for adherent culture (manufactured by Asahi Techno Glass) at a density of 1,000 cells/well. To each well, 1 mg/ml of *Lens culinaris* agglutinin (hereinafter referred to as LCA, manufactured by Vector) was added as a final concentration in the medium. After culturing at 37° C. for 2 weeks in a $CO_2$ incubator, the thus formed colonies were obtained as lectin-resistant CHO/DG44 cell lines.

2. Determination of GDP-mannose 4,6-dehydratase mRNA of the Obtained Lectin-Resistant CHO/DG44 Cell Lines The expressed amount of GDP-mannose 4,6-dehydratase as an enzyme capable of catalyzing dehydrogenation to convert GDP-mannose into GDP-4-keto,6-deoxy-GDP-mannose in each of the lectin-resistant CHO/DG44 cell lines obtained in the above item was analyzed in the following manner using RT-PCR method.

(1) Preparation of RNA from Lectin-Resistant CHO/DG44 Cell Line and Preparation of Single-Stranded cDNA RNA samples were prepared respectively from $1\times10^7$ cells of the parent cell line CHO/DG44 cell and each of the lectin-resistant CHO/DG44 cell lines obtained in item 1 of this Example, using RNeasy Protect Mini Kit (manufactured by QIAGEN) in accordance with the instructions attached thereto. Subsequently, single-stranded cDNA was synthesized from 5 μg of each RNA in 20 μl of a reaction mixture using SUPER SCRIPT First-Strand synthesis system for RT-PCR (manufactured by Invitrogen) in accordance with the instructions attached thereto.

(2) Analysis of Expression Quantity of β-Actin Gene Using RT-PCR

In order to verify quality of each of the respective cell line-derived single-stranded cDNA samples prepared in the above item (1), amplification of β-actin cDNA by PCR was examined in the following manner.

After 20 μl of a reaction mixture [1× EX Taq Buffer (manufactured by Takara Shuzo), 0.2 mM of dNTPs, 0.5 unit of EX Taq polymerase (manufactured by Takara Shuzo) and 0.5 μM of the synthetic oligo DNA primers of SEQ ID NOs:32 and 33] containing, as the template, 0.5 μl of each of the respective cell line-derived single-stranded cDNA samples prepared in the above (1) was prepared, the reaction mixture was heated at 94° C. for 5 minutes and then 14 cycles of the reaction, one cycle consisting of reaction at 94° C. for one minute and reaction at 68° C. for 2 minutes, were carried out using DNA Thermal Cycler 480 (manufactured by Perkin Elmer). After 10 μl of the resulting PCR reaction mixture was subjected to agarose electrophoresis, the DNA fragments were stained using Cyber Green (manufactured by BMA), and then the amount of the expected DNA fragment of approximately 800 bp was measured using Fluor Imager SI (manufactured by Molecular Dynamics). As a result, it was able to detect the expression of β-actin at a similar level by using every cell line-derived single-stranded cDNA.

(3) Analysis of the Expressed Amount of GDP-mannose 4,6-dehydratase Gene Using RT-PCT Method Next, the expressed amount of GDP-mannose 4,6-dehydratase gene in the respective lectin-resistant CHO/DG44 cell lines obtained in the above item (1) was analyzed. In order to amplify cDNA of GDP-mannose 4,6-dehydratase gene by PCR, a synthetic oligo DNA primer of 26 mer having the nucleotide sequence represented by SEQ ID NO:34 and a synthetic oligo DNA primer of 28 mer having the nucleotide sequence represented by SEQ ID NO:35 were prepared from the cDNA sequence of CHO cell-derived GDP-mannose 4,6-dehydratase represented by SEQ ID NO:38. Subsequently, 20 μl of a reaction mixture [1× EX Taq Buffer (manufactured by Takara Shuzo), 0.2 mM of dNTP mixture, 0.5 unit of EX Taq polymerase (manufactured by Takara Shuzo) and 0.5 μM of the synthetic oligo DNA primers of SEQ ID NOs:34 and 35] containing, as the template, 0.5 ηl of each of the respective cell line-derived single-stranded cDNA samples prepared in the above item (1) was prepared, the reaction mixture was heated at 94° C. for 5 minutes, and then 30 cycles of the reaction, one cycle consisting of reaction at 94° C. for one minute and reaction at 68° C. for 2 minutes, were carried out by using DNA Thermal Cycler 480 (manufactured by Perkin Elmer). After 10 μl of the resulting PCR reaction mixture was subjected to agarose electrophoresis, the DNA fragments were stained using Cyber Green (manufactured by BMA), and then amount of the expected DNA fragment of approximately 430 bp was measured using Fluor Imager SI (manufactured by Molecular Dynamics) As a result, it was confirmed that a cell line in which expression of GDP-mannose 4,6-dehydratase gene is not observed is present in the obtained lectin-resistant CHO/DG44 cell lines. The cell line in which no expression of GDP-mannose 4,6-dehydratase gene was observed was named cell line CHO SM. In this connection, when resistance of the thus obtained cell line CHO SM to various species of lectin was examined, the cell line CHO SM showed a resistance also to a lectin which recognizes the same sugar chain structure as the sugar chain structure which is recognized by LCA, namely other lectin which recognizes a sugar chain structure in which 1-position of fucose is bound to 6-position of N-acetylglucosamine residue in the reducing end through α-bond in the N-glycoside-linked sugar chain. Specifically, it showed resistance to a medium supplemented with 1 mg/ml in final concentration of *Pisum sativum* agglutinin (hereinafter referred to as PSA, manufactured by Vector) or to a medium supplemented with 1 mg/ml in final concentration of *Aleuria aurantia* lectin (hereinafter referred to as AAL, manufactured by Vector).

3. Genomic Analysis of Cell Line in which the Gene of an Enzyme Capable of Catalyzing Dehydrogenation to Convert GDP-mannose into GDP-4-keto,6-deoxy-GDP-mannose is Not Expressed Using a T75 flask for adherent culture (manufactured by Greiner), each of CHO/DG44 cell and the CHO SM cell line obtained in the above was cultured in IMDM-FBS(10)-HT(1) medium until it reached just before the confluent stage, and then genomic DNA was prepared in accordance with the method described in a literature [*Nucleic Acid Research*, 3, 2303 (1976)], and the thus obtained genomic DNA was dissolved overnight in 300 µl of TE-RNase buffer solution (pH 8.0) [10 mmol/l Tris-HCl, 1 mmol/l EDTA, 200 µg/l RNase A]. After 12 µg of the genomic DNA prepared in the above was digested with three different restriction enzymes EcoRI (manufactured by Takara Shuzo), HindIII (manufactured by Takara Shuzo) and BglII (manufactured by Takara Shuzo), respectively, the DNA fragments were recovered using the ethanol precipitation method and then dissolved in 20 µl of TE buffer (pH 8.0) [10 mmol/l Tris-HCl, 1 mmol/l EDTA] and subjected to 0.8% (w/v) agarose gel electrophoresis. After the electrophoresis, the genomic DNA fragments were transferred onto a nylon membrane in accordance with the method described in a literature [*Proc. Natl. Acad. Sci. USA*, 76, 3683 (1979)]. After the transfer, heat treatment of the nylon membrane was carried out at 80° C. for 2 hours. Next, in order to examine the quality of the genomic DNA transferred onto the nylon membrane, Southern hybridization was carried out using, as the probe, α1,6-fucosyltransferase (FUT8) gene which is considered to be present uniformly in the genome of every cell line. The probe for detecting the FUT8 gene was prepared in the following manner. Firstly, 10 µg of a plasmid mfFUT8-pCR2.1 containing mouse FUT8 cDNA as described in Example 11 of WO02/31140, was dissolved in 50 µl of M buffer (manufactured by Takara Shuzo), digested overnight with a restriction enzyme HindIII (manufactured by Takara Shuzo), and then the reaction mixture was replaced with H buffer (manufactured by Takara Shuzo) and digestion reaction with a restriction enzyme EcoRI (manufactured by Takara Shuzo) was further carried out overnight. After completion of the reaction, the reaction mixture was subjected to 2% agarose electrophoresis, and an EcoRI-HindIII fragment of 156 bp containing exon 2 of FUT8 gene was purified. A 25 ng portion of the thus obtained DNA fragment was radiation-labeled using 1.75 MBq of [α-$^{32}$P]dCTP and Megaprime DNA labeling system, dCTP (manufactured by Amersham Bioscience). Next, hybridization was carried out in the following manner. Firstly, the above-described nylon membrane was sealed in a roller bottle, and pre-hybridization was carried out at 65° C. for 3 hours by adding 15 ml of a hybridization solution [4×SSPE, 5× Denhaldt's solution, 0.5% (w/v) SDS, 0.1 mg/ml sermon sperm DNA]. Next, the $^{32}$P-labeled probe DNA was denatured with heat, charged into the bottle and heated overnight at 65° C. After the hybridization, the nylon membrane was soaked in 50 ml of 2×SSC-0.1% (w/v) SDS and heated at 65° C. for 15 minutes. After repeating the above washing step twice, the nylon membrane was soaked in 50 ml of 0.2×SSC-0.1% (w/v) SDS and heated at 65° C. for 15 minutes. After washing, the nylon membrane was exposed to an X-ray film at 80° C. two nights for development. After the development, the nylon membrane was boiled in a stripping solution [1% SDS, 0.1×SSC) to release the probe and again subjected to hybridization with different probe. By the above-described method, a fragment specific to exon 2 of FUT8 gene was detected in the genomic DNA of each of the cell line CHO/DG44 and cell line CHO SM Based on the above results, it was shown that the genomic DNA samples transferred onto the nylon membrane, derived from the cell line CHO SM and cell line CHO/DG44, have the identical quality.

On the other hand, a probe specific to exon 5 of GMD gene was prepared in the following manner. Firstly, oligo DNA primers (SEQ ID NOs:36 and 37) which specifically bind to the exon 5 were designed based on a conventionally known human GMD genomic DNA sequence (NCBI accession No. NT-034880). The region corresponds to a region of the nucleotide number 346 to the nucleotide number 538 of the human GMD cDNA sequence represented by SEQ ID NO:39. Next, polymerase chain reaction (PCR) was carried out by preparing 100 µl of a reaction mixture [ExTaq buffer (manufactured by Takara Shuzo), 0.2 mmol/l of dNTPs and 2.5 µmol/l of the above-described gene-specific primers (SEQ ID NOs:36 and 37)] containing 10 ng of the plasmid pAGE249GMD described in Example 15 of WO02/31140. The PCR was carried out by heating at 94° C. for 5 minutes and 30 cycles, one cycle consisting of reaction at 94° C. for one minute, reaction at 58° C. for 2 minutes and reaction at 72° C. for 3 minutes. After the PCR, the reaction mixture was subjected to 2% agarose electrophoresis, and a DNA fragment of approximately 200 bp was purified Next, 25 ng of the thus obtained DNA fragment was radiation-labeled using 1.75 MBq of [α-$^{32}$P]dCTP and Megaprime DNA labeling system, dCTP (manufactured by Amersham Bioscience). Using the probe, hybridization was carried out on the above-described nylon membrane. As a result, a fragment specific to exon 5 of GMD gene was found in the genomic DNA derived from the CHO/DG44 cell, while a fragment specific to exon 5 of GMD gene was not detected in the genomic DNA derived from the cell line CHO SM. Based on the above results, it was shown that the cell line CHO SM is a GMD-knockout cell in which at least an exon 5-containing region among the GMD-encoding genomic region was deleted.

EXAMPLE 8

Expression of Recombinant Antithrombin III in Cell Line CHO SM:

1. Introduction of ATIII Expression Plasmid into Cell Line CHO SM

The plasmid pKAN-ATIII prepared in Example 2-3 was stably introduced into the cell line CHO SM prepared in Example 7. The gene introduction was carried out by the following procedure in accordance with the conventionally known electroporation method [*Cytotechnology*, 3, 133 (1990)1. Firstly, 30 µg of the plasmid pKAN-ATIII was linearized by preparing 200 µl of a reaction mixture containing 20 µl of NEBuffer 3 (manufactured by New England Biolabs)

and 100 units of a restriction enzyme MluI (manufactured by New England Biolabs) and digesting at 37° C. for 16 hours. After the reaction, the reaction mixture was purified by phenol/chloroform extraction treatment and ethanol precipitation to thereby recover the linear plasmid Next, the cell line CHO SM obtained in Example 7 was suspended in a K-PBS buffer (137 mmol/l KCl, 2.7 mmol/l NaCl, 8.1 mmol/l $Na_2HPO_4$, 1.5 mmol/l $KH_2PO_4$, 4.0 mmol/1 $MgCl_2$) to prepare a suspension of $8×10^7$ cells/ml. After 200 µl of the cell suspension ($1.6×10^6$ cells) was mixed with 9 µg of the above-described linear plasmid, a full volume of the cell-DNA mixture was transferred into Gene Pulser Cuvette (2 mm in inter-electrode distance, manufactured by BIO-RAD), and gene introduction was carried out using an electroporation device Gene Pulser (manufactured by BIO-RAD) under conditions of 350 V in pulse voltage and 250 µF in electric capacity. After carrying out the gene introduction, the cell suspension was suspended in 30 ml of IMDM medium (manufactured by Life Technologies) supplemented with 10% fetal bovine serum (manufactured by Life Technologies) and 50 µg/ml of gentamicin (manufactured by Nacalai Tesque) and inoculated at 100 µl/well into 96-well 3 plates for adherent cells (manufactured by Greiner). The culturing was carried out under conditions of 5% $CO_2$ and 37° C.

2. Obtaining of MTX-Resistant Cell Line

The pKAN-ATIII-introduced cells obtained in the above were cultured for 6 days, and then the culture supernatants were discarded and the IMDM medium supplemented with 10% dialyzed fetal bovine serum, 50 µg/ml gentamicin and 50 nM MTX (manufactured by SIGMA) was dispensed at 100 µl/well. The culturing was continued for 9 days while repeating this medium exchanging work at an interval of 3 to 4 days. Next, the culturing was continued for 18 days while repeating the medium exchanging work using the IMDM medium supplemented with 10% dialyzed fetal bovine serum, 50 µg/ml gentamicin and 200 nM MTX at an interval of 3 to 4 days, and the finally formed colonies were inoculated into a 24 well plate (manufactured by SIGMA). Subsequently, the culturing was continued for 19 days while repeating the medium exchanging work using the IMDM medium supplemented with 10% dialyzed fetal bovine serum, 50 µg/ml gentamicin and 500 nM MTX at an interval of 3 to 4 days, optionally expanding the process to thereby obtain cell lines resistant to 500 nM MTX.

3. Selection of Cell Line Highly Producing Antithrombin III

From each of the several 500 nm MTX-resistant cell lines obtained in the above item, $1.0×10^6$ cells were collected, suspended in 5 ml of the IMDM medium supplemented with 10% dialyzed fetal bovine serum, 50 µg/ml gentamicin and 500 nM MTX, and then cultured by inoculating into a T25 flask. Three days after the culturing, the culture supernatant was recovered, and the amount of ATIII contained in the supernatant was measured using ELISA for antithrombin (ATIII) kit (manufactured by Affinity Biological). As a result, it was confirmed that the recombinant human antithrombin III is expressed in the culture supernatant at a concentration of 513 ng/ml, and this transformant was named cell line pKAN-ATIII1 GMDKO.

Thereafter, a recombinant antithrombin III having a sugar chain in which fucose is not bound to N-acetylglucosamine in the reducing end was obtained by the method described in Example 4. In addition, by measuring biological activities of the antithrombin III by the method described in Example 5, it was confirmed that the recombinant antithrombin expressed in the GMD knockout cell has significantly smaller heparin dissociation constant and significantly higher heparin cofactor activity and thrombin inhibition secondary rate constant, than the recombinant antithrombin III expressed in the CHO/DG44 cell.

EXAMPLE 9

Expression of Amino Acid-modified Recombinant Antithrombin III in Cell Line CHO SM:

1. Introduction of ATIIIN135Q Expression Plasmid into Cell Line CHO SM

The plasmid pKAN-ATIIIN135Q prepared in Example 6-2 was introduced into the cell line CHO SM prepared in Example 7. The gene introduction was carried out by the following procedure in accordance with the conventionally known electroporation method [*Cytotechnology*, 3, 133 (1990)]. Firstly, 30 µg of the plasmid pKAN-ATIIIN135Q was linearized by preparing 200 µl of a reaction mixture containing 20 µl of NEBuffer 3 (manufactured by New England Biolabs) and 100 unites of a restriction enzyme MluI (manufactured by New England Biolabs) and digesting at 37° C. for 16 hours. After the reaction, the reaction mixture was purified by phenol/chloroform extraction treatment and ethanol precipitation to thereby recover the linear plasmid. Next, the cell line CHO SM obtained in Example 7 was suspended in a K-PBS buffer (137 mmol/l KCl, 2.7 mmol/l NaCl, 8.1 mmol/l $Na_2HPO_4$, 1.5 mmol/l $KH_2PO_4$, 4.0 mmol/l $MgCl_2$) to prepare a suspension of $8×10^7$ cells/ml. After 200 µl of the cell suspension ($1.6×10^6$ cells) was mixed with 9 µg of the above-described linear plasmid, a full volume of the cell-DNA mixture was transferred into Gene Pulser Cuvette (2 mm in inter-electrode distance, manufactured by BIO-RAD), and gene introduction was carried out using an electroporation device Gene Pulser (manufactured by BIO-RAD) under conditions of 350 V in pulse voltage and 250 µF in electric capacity. After carrying out the gene introduction, the cell suspension was suspended in 30 ml of IMDM medium (manufactured by Life Technologies) supplemented with 10% fetal bovine serum (manufactured by Life Technologies) and 50 µg/ml of gentamicin (manufactured by Nacalai Tesque) and inoculated at 100 µl/well into 3 plates of 96-wells for adherent cells (manufactured by Greiner). The culturing was carried out under conditions of 5% $CO_2$ and 37° C.

2. Obtaining of MTX-resistant Cell Line

The pKAN-ATIIIN135Q-introduced cells obtained in the above item were cultured for 6 days, and then the culture supernatants were discarded and the IMDM medium supplemented with 10% dialyzed fetal bovine serum, 50 µg/ml gentamicin and 50 nM MTX (manufactured by SIGMA) was dispensed at 100 µl/well. The culturing was continued for 9 days while repeating this medium exchanging work at an interval of 3 to 4 days. Next, the culturing was continued for 18 days while repeating the medium exchanging work using the IMDM medium supplemented with 10% dialyzed fetal bovine serum, 50 µg/ml gentamicin and 200 nM MTX at an interval of 3 to 4 days, and the finally formed colonies were inoculated into a 24 well plate (manufactured by Greiner). Subsequently, the culturing was continued for 19 days while repeating the medium exchanging work using the IMDM medium supplemented with 10% dialyzed fetal bovine serum, 50 µg/ml gentamicin and 500 nM MTX at an interval of 3 to 4 days, optionally expanding the process to thereby obtain cell lines resistant to 500 nM MTX.

3. Selection of Cell Line Highly Producing ATIIIN135Q

From each of the several 500 nm MTX-resistant cell lines obtained in the above item, $1.0×10^6$ cells were collected, suspended in 5 ml of the IMDM medium supplemented with 10% dialyzed fetal bovine serum, 50 μg/ml gentamicin and 500 nM MTX, and then cultured by inoculating into a T25 flask. Three days after the culture supernatant was recovered, and the amount of ATIIIN[135Q] contained in the supernatant was measured using ELISA for antithrombin (ATIII) kit (manufactured by Affinity Biological), to establish a highly producing cell line, The method was carried out in accordance with the manual attached hereto, and Neuart (manufactured by Mitsubishi Pharma Corporation) was used as the standard preparation. As a result, it was confirmed that antithrombin III is expressed in the culture supernatant of the thus obtained antithrombin III expressing cell line, at a concentration of 45.4 ng/ml, and this transformant was named cell line pKAN-ATIIIN135Q GMDKO Thereafter, a mutation type recombinant antithrombin III having a sugar chain in which fucose is not bound to N-acetylglucosamine in the reducing end was obtained by the method described in Example 4, and it was confirmed that the number of the N-linked type sugar chains was three. In addition, by measuring the biological activity of the antithrombin III by the method described in Example 5, it was confirmed that the mutation type recombinant antithrombin III expressed in the GMDKO cell has significantly smaller heparin dissociation constant and significantly higher heparin cofactor activity and thrombin inhibition secondary rate constant, than the mutation type recombinant antithrombin III expressed in the CHO/DG44 cell.

EXAMPLE 10

Expression of Recombinant Antithrombin III in Yeast:

Although many kinds of yeast are known, yeasts belonging to the genus *Pichia* and the genus *Saccharomyces* can be exemplified as typical yeasts frequently used as the hosts for expressing recombinant proteins. In general, it is known that the principal structure of N-linked type sugar chains to be added to the recombinant proteins expressed by these yeasts is a high mannose type sugar chain which has 2 N-acetylglucosamine residues in the core residue of the reducing end, and has 9 to several tens of mannose residues and a few to over 10 mannose 6-phosphate residues in the branched region in the non-reducing end (*Yeast,* 12, 1191 (2002)). In addition, a high mannose type sugar chain having such a structure is often called hyper mannose type sugar chain.

In Examples described below, firstly described are preparation methods of *Pichia* strains and *Saccharomyces* strains capable of expressing an antithrombin III to which a hybrid type sugar chain, having an intermediate structure of high mannose type sugar chain and complex type sugar chain, is mainly added as the N-linked type sugar chain.

1. Preparation of a *Pichia* Yeast Strain in which Genomic PNO 1 Enzyme Gene is Disrupted Using genomic DNA of a *Pichia* yeast strain, such as *Pichia pastoris* strain GTS 115 (manufactured by Invitrogen) as the template, a full sequence of the translation region of PNO 1 (phosphomannosylation of N-linked oligosaccharides 1) gene (GenBank accession number: AB099514) of the *Pichia* yeast is amplified by PCR. The thus amplified PNO 1 gene sequence of approximately 3,200 bp, after replacing its 5'-terminal half sequence by a yeast-derived orotidine-5'-phosphate decarboxylase (URA 3) gene (GenBank accession number: AF321098), is inserted into a vector such as pCR2.1-TOPO vector (manufactured by Invitrogen) to prepare a plasmid for PNO 1 gene disruption use. Next, 100 μg of this plasmid is linearized by using a restriction enzyme, and then stably introduced into the *Pichia* yeast such as GTS 115 by the electroporation method described in *Pichia* Expression Kit (manufactured by Invitrogen). Next, the gene-introduced yeast is cultured at room temperature using uracil-deleted YPD medium (manufactured by Invitrogen), and genomic DNA is extracted from each of the grown colonies. Subsequently, by amplifying the sequence of yeast PNO 1 locus by PCR using this genomic DNA as the template, a yeast clone in which the PNO 1 locus is disrupted by homologous recombination is selected. By the above method, the principal structure of N-linked type sugar chain expressed by the *Pichia* yeast can be modified into a high mannose type sugar chain which has 2 N-acetylglucosamine residues in the core residue of the reducing end, and has a structure in which 9 to several tens of mannose residues are bound to the non-reducing end.

2. Preparation of a *Pichia* Yeast Strain in which Genomic α-1,6-mannosyltransferase Gene is Disrupted Using genomic DNA of a *Pichia* yeast strain, such as *Pichia pastoris* strain X-33 (manufactured by Invitrogen) as the template, α-1,6mannosyltransferase (OCH 1) gene (GenBank accession number: AF540063) of the *Pichia* yeast is amplified by PCR. The thus amplified OCH 1 gene sequence of approximately 2,800 bp, after replacing its 5'-terminal half sequence by a yeast-derived orotidine-5'-phosphate decarboxylase (URA 3) gene (GenBank accession number: AF321098), is inserted into a vector such as pCR2.1-TOPO vector (manufactured by Invitrogen) to prepare a vector for disruption of OCH 1 gene. Next, 100 μg of this vector is linearized by using a restriction enzyme SfiI (manufactured by New England Biolabs), and then stably introduced into a *Pichia* strain, such as the PNO 1 gene-disrupted strain described in the above item or *Pichia pastoris* strain JC308, by the electroporation method described in *Pichia* Expression Kit (manufactured by Invitrogen). Next, the gene-introduced yeast is cultured at room temperature using uracil-deleted YPD medium (manufactured by Invitrogen), and genomic DNA is extracted from each of the grown colonies. Subsequently, by amplifying the sequence of yeast OCH 1 locus by PCR using this genomic DNA as the template, a yeast clone strain in which the OCH 1 locus is disrupted by homologous recombination is selected. By the above method, the principal structure of N-linked type sugar chain expressed by the *Pichia* yeast can be modified into a Man8 type high mannose type sugar chain which has 2 N-acetylglucosamine residues in the core part of the reducing end, and has a structure in which 8 mannose residues are bound to the non-reducing end.

3. Preparation of *Pichia* Yeast Strain into which Recombinant Chimeric α-1,2-mannosidase Gene is Introduced Total RNA is extracted from a round worm (*Caenorhabditis elegans*) using RNeasy Mini Kit (manufactured by QIAGEN), and then first-strand cDNA is prepared using this RNA as the template and using Superscript™ first-strand cDNA synthesis kit (manufactured by Invitrogen). Next, by carrying out PCR using this cDNA as the template and using specific primers and KOD polymerase (manufactured by Toyobo Co., Ltd.), a cDNA encoding the active domain of round worm α-1,2-mannosidase (GenBank accession number: NM-073594) is specifically amplified. The thus amplified cDNA, after ligating a cDNA sequence encoding the leader peptide of a yeast α-mannosidase (MNS 1) gene (GenBank accession number: M63598) to its 5'-terminal, is inserted into a vector such as expression vector PPICZ for yeast (manufactured by Invitrogen) to thereby prepare a vector for expressing α-1,2-mannosidase in the yeast endoplasmic reticulum. Next, this vector is stably introduced by electroporation into the above-described *Pichia* yeast strain in which both of the PNO 1 gene and OCH 1 gene are disrupted by homologous recombination. The yeast after the gene introduction is cultured at room temperature using YPD medium (manufactured by Invitrogen) lacking uracil and containing zeosine (manufactured by Invitrogen), and total RNA is extracted from each of the grown colonies. Next, a yeast clone strain in which expression of the recombinant chimeric α-1,2-mannosidase is found is selected by PCR using a first-strand cDNA prepared from this total RNA as the template. By the above method, the principal structure of N-linked type sugar chain expressed by the *Pichia* yeast can be modified into a Man8 type high mannose type sugar chain which has 2 N-acetylglucosamine residues in the core residue of the reducing end, and has a structure in which 5 mannose residues are bound to the non-reducing end.

4. Preparation of *Pichia* Yeast Strain into which a Recombinant UDP-N-acetylglucosamine Transporter Gene is Introduced Total RNA is extracted from a yeast (*Kluyveromyces lactis*) using RNeasy Mini Kit (manufactured by QIAGEN), and then cDNA is prepared using this RNA as the template and using Superscript™ first-strand cDNA synthesis kit (manufactured by Invitrogen). Next, by carrying out PCR using this cDNA as the template and using specific primers and KOD polymerase (manufactured by Toyobo Co., Ltd.), a cDNA encoding a full translation region of yeast UDP-N-acetylglucosamine transporter (GenBank accession number: AF106080) is specifically amplified. Next, the thus amplified cDNA of approximately 3,700 bp is inserted between restriction enzymes EcoRI cleavage site and NotI cleavage site positioned at the downstream of the alcohol oxygenase promoter sequence of a vector such as an expression vector pPIC3.5K for yeast (manufactured by Invitrogen) to thereby prepare a vector which expresses UDP-N-acetylglucosamine transporter in the yeast Golgi body. Next, this vector is stably introduced by electroporation into the α-1,2-mannosidase gene-introduced *Pichia* yeast strain described in the above item. The yeast after the gene introduction is cultured at room temperature using YPD medium containing an agent G418 (manufactured by Nacalai Tesque), and total RNA is extracted from each of the grown colonies. Thereafter, a yeast clone strain in which expression of recombinant UDP-N-acetylglucosamine transporter is found is selected by PCR using cDNA prepared from this total RNA as the template.

5. Preparation of *Pichia* Yeast Strain into which Recombinant Chimeric N-acetylglucosaminyltransferase-I Gene is Introduced By carrying out PCR using a human liver cDNA (manufactured by Clontech) as the template and using specific primers and KOD polymerase (manufactured by Toyobo Co., Ltd.), a cDNA encoding the active domain of N-acetylglucosaminyltransferase-I (GenBank accession number: M55621) is specifically amplified. The thus amplified cDNA, after ligating a cDNA sequence encoding the leader peptide of a yeast mannosyltransferase (NM 9) gene (GenBank accession number: L23752) to its 5'-terminal, is inserted between restriction enzymes KpnI cleavage site and XbaI cleavage site positioned at the downstream of the alcohol dehydrogenase promoter sequence of a vector such as an expression vector pAUR123 for yeast (manufactured by Takara Bio), to thereby prepare a vector which expresses N-acetylglucosaminyltransferase-I in the yeast Golgi body. Next, this vector is introduced into the UDP-N-acetylglucosamine transporter gene-introduced *Pichia* yeast strain described in the above, by the lithium acetate method described in the manual attached to the expression vector pAUR123. The yeast after the gene introduction is cultured at room temperature using YPD medium containing an agent aurobrassidin A (manufactured by Takara Bio), and total RNA is extracted from each of the grown colonies. Next, a yeast clone strain in which expression of the recombinant N-acetylglucosaminyltransferase-I is found is selected by PCR using a cDNA prepared from this total RNA as the template. By the above method, the principal structure of N-linked type sugar chain expressed by the *Pichia* yeast can be modified into a hybrid type sugar chain having a structure in which one N-acetylglucosamine residue is added to the non-reducing end of a Man8 type high mannose type sugar chain which has 2 N-acetylglucosamine residues in the core residue of the reducing end, and has 5 mannose residues bound to the non-reducing end.

Thus, preparation methods of *Pichia* yeast strains which mainly express a hybrid type sugar chain, namely an intermediate structure of high mannose type sugar chain and complex type sugar chain, as the N-linked type sugar chain have been described. In addition to the above-described Pichia strains, yeasts belonging to the genus *Saccharomyces* can be exemplified as the yeast frequently used as the host for expressing recombinant proteins. Preparation methods of a *Saccharomyces* yeast strain which mainly expresses a hybrid type sugar chain as the N-linked type sugar chain are described below.

6. Preparation of *Saccharomyces* Yeast Strain in which α-1,6-mannosyltransferase Gene and α-1,3-mannosyltransferase Gene on the Genome are Disrupted In accordance with the method of Nakayama et al. (*EMBO Journal*, 11, 2511 (1992)), a yeast clone in which the OCH 1 locus is disrupted by homologous recombination is selected. Haploid cells are induced in accordance with the method of Sherman et al. (*Methods in Enzymology*, 194, 21 (1991)) from the *Saccharomyces* yeast strain in which the OCH 1 gene locus is disrupted, and then mixed with haploid cells of a mutant yeast strain LB1-10B in which the α-1,3-mannosyltransferase (MNN 1) gene is disrupted (University of California), followed by culturing under nitrogen-deficient conditions to form diploid zygotes. Next, the thus obtained zygotes are cultured at room temperature using YPD medium lacking uracil and leucine, and genomic DNA is extracted from each of the grown colonies. Subsequently, a yeast clone strain in which both of the OCH 1 gene locus and MNN 1 gene locus are disrupted is selected by respectively amplifying sequence of the yeast OCH 1 locus (GenBank accession number: AF540063) and sequence of the MNN 1 locus (GenBank accession number: AF540063L23753) through PCR using this genomic DNA as the template. By the above method, the principal structure of N-linked type sugar chain expressed by the *Saccharomyces* yeast can be modified into a Man8 type high mannose type sugar chain which has 2 N-acetylglucosamine residues in the core residue of the reducing end, and has a structure in which 8 mannose residues are bound to the non-reducing end.

7. Preparation of *Saccharomyces* Yeast Strain into which Recombinant Chimeric α-1,2-mannosidase Gene is Introduced Total RNA is extracted from a fungus (*Aspergillus saitoi*) using RNeasy Mini Kit (manufactured by QIAGEN), and then cDNA is prepared using this RNA as the template and using Superscript™ first-strand cDNA synthesis kit (manufactured by Invitrogen). Next, by carrying out PCR using this cDNA as the template and using specific primers and KOD polymerase (manufactured by Toyobo Co., Ltd.), a cDNA encoding the full translation region of fungal α-1,2-mannosidase (GenBank accession number. D49827) is specifically amplified. After ligating a yeast endoplasmic reticulum-specific signal peptide (*EMBO Journal*, 7, 913 (1988)), namely a cDNA sequence encoding histidine-aspartic acid-glutamic acid-leucine and a translation termination codon, to the 3'-terminal of the thus amplified cDNA of approximately 1,500 bp, from which its translation termination codon have been eliminated, is inserted into a vector such as expression vector pPICZ for yeast (manufactured by Invitrogen) or the like, to thereby prepare a vector for expressing α-1,2-mannosidase in the yeast endoplasmic reticulum. Next, this vector is stably introduced by electroporation into the above-described *Saccharomyces* yeast strain in which the α-1,6-mannosyltransferase gene and the α-1,3-mannosyltransferase gene are disrupted. The yeast after the gene introduction is cultured at room temperature using YPD medium (manufactured by Invitrogen) lacking uracil and containing zeosine (manufactured by Invitrogen), and total RNA is extracted from each of the grown colonies. Subsequently, a yeast clone strain in which expression of the recombinant chimeric α-1,2-mannosidase is found is selected by PCR using a cDNA prepared from this total RNA as the template. By the above method, the principal structure of N-linked type sugar chain expressed by the *Saccharomyces* yeast can be modified into a Man8 type high mannose type sugar chain which has 2 N-acetylglucosamine residues in the core residue of the reducing end, and has a structure in which 5 mannose residues are bound to the non-reducing end.

8. Preparation of *Saccharomyces* Yeast Strain into which a Recombinant UDP-N-acetylglucosamine Transporter Gene is Introduced Total RNA is extracted from a yeast (*Kluyveromyces lactis*) using RNeasy Mini Kit (manufactured by QIAGEN), and then cDNA is prepared using this RNA as the template and using Superscript™ first-strand cDNA synthesis kit (manufactured by Invitrogen). Next, by carrying out PCR using this cDNA as the template and using specific primers and KOD polymerase (manufactured by Toyobo Co., Ltd.), a cDNA encoding a full translation region of yeast UDP-N-acetylglucosamine transporter (GenBank accession number: AF106080) is specifically amplified. Next, the thus amplified cDNA of approximately 3,700 bp is inserted between restriction enzymes EcoRI cleavage site and NotI cleavage site positioned at the downstream of the alcohol oxygenase promoter sequence of a vector such as an expression vector pPIC3.5K for yeast (manufactured by Invitrogen), to thereby prepare a vector which expresses UDP-N-acetylglucosamine transporter in the yeast Golgi body. Next, this vector is stably introduced by electroporation into the α-1,2-mannosidase gene-introduced *Saccharomyces* strain described in the above item. The yeast after the gene introduction is cultured at room temperature using YPD medium containing an agent G41g (manufactured by Nacalai Tesque), and total RNA is extracted from each of the grown colonies. Thereafter, a yeast clone strain in which expression of recombinant UDP-N-acetylglucosamine transporter is found is selected by PCR using cDNA prepared from this total RNA as the template.

9. Preparation of *Saccharomyces* Yeast Strain into which Recombinant Chimeric N-acetylglucosaminyltransferase-I Gene is Introduced By carrying out PCR using a human liver cDNA (manufactured by Clontech) as the template and using specific primers and KOD polymerase (manufactured by Toyobo Co., Ltd.), a cDNA encoding the active domain of N-acetylglucosaminyltransferase-I (GenBank accession number: M55621) is specifically amplified. The thus amplified cDNA, after ligating a cDNA sequence encoding the leader peptide of a yeast mannosyltransferase (MNN 9) gene (GenBank accession number. L23752) to its 5'-terminal, is inserted between restriction enzymes KpnI cleavage site and XbaI cleavage site positioned at the downstream of the alcohol dehydrogenase promoter sequence of a vector such as an expression vector pAUR123 for yeast (manufactured by Takara Bio), to thereby prepare a vector which expresses N-acetylglucosaminyltransferase-I in the yeast Golgi body. Next, this vector is introduced into the UDP-N-acetylglucosamine transporter gene-introduced *Saccharomyces* yeast strain described in the above item, by the lithium acetate method described in the manual attached to the expression vector pAUR123. The yeast after the gene introduction is cultured at room temperature using YPD medium containing an agent aurobrassidin A (manufactured by Takara Bio), and total RNA is extracted from each of the grown colonies. Next, a yeast clone strain in which expression of the recombinant N-acetylglucosaminyltransferase-I is found is selected by PCR using a cDNA prepared from this total RNA as the template. By the above method, the principal structure of N-linked type sugar chain expressed by the *Saccharomyces* yeast can be modified into a hybrid type sugar chain having a structure in which one N-acetylglucosamine residue is added to the non-reducing end of a Man8 type high mannose type sugar chain which has 2 N-acetylglucosamine residues in the core residue of the reducing end, and has 5 mannose residues bound to the non-reducing end.

Thus, preparation methods of *Pichia* yeast strains or *Saccharomyces* yeast strains which mainly express a hybrid type sugar chain in which one N-acetylglucosamine residue is added to the non-reducing end of a Man8 type high mannose type sugar chain, as the N-linked type sugar chain have been described. The preparation methods of a recombinant human antithrombin III mainly having a hybrid type sugar chain as the N-linked type sugar chain are described below.

10. Preparation of Recombinant Human Antithrombin III Expression Vector

In accordance with the method of Yamauchi et al. (*Bioscience, Biotechnology and Biochemistry*, 56, 600 (1992)), a cDNA encoding the full length mature type human antithrombin III is specifically amplified by PCR using a human liver cDNA (manufactured by Clontech) as the template and KOD polymerase (manufactured by Toyobo Co., Ltd.) as the enzyme for amplification. Thereafter, the thus obtained cDNA is inserted between restriction enzymes ClaI cleavage site and XbaI cleavage site positioned at the downstream of the alcohol oxygenase promoter sequence of a vector such as an expression vector pPIC6α for yeast (manufactured by Invitrogen), to thereby prepare a vector pPIC6α/hATIII which expresses and secretes the mature type human antithrombin III.

11. Preparation of Yeast Strain into which Recombinant Human Antithrombin III Gene is Introduced A linearized vector is prepared from 100 μg of the vector pPIC6α/hATIII which expresses and secretes the mature type human antithrombin III described in the above, by digesting inside of the HIS4 gene with a restriction enzyme SalI (manufactured by New England Biolabs) and subjecting the resulting fragments to phenol/chloroform extraction and ethanol precipitation. Next, in accordance with the method of Mochizuki et al. (*Protein Expression and Purification*, 23, 55 (2001)), this linearized antithrombin III expression vector is introduced by the lithium acetate method into the *Pichia* yeast strain capable of expressing mainly a hybrid type sugar chain as the N-linked type sugar chain described in the above-described item 5 of this Example or the *Saccharomyces* yeast strain capable of expressing mainly a hybrid type sugar chain as the N-linked type sugar chain described in the above 9 of this Example. The yeast after the gene introduction is cultured at room temperature using YPD medium (manufactured by Invitrogen) containing an agent blasticidin (manufactured by Invitrogen) to obtain blasticidin-resistant colonies. Next, each of the blasticidin-resistant colonies is inoculated into liquid YPD medium (manufactured by Invitrogen) to carry out batch culturing at 30° C. for 24 hours or more. The culture supernatant obtained after the culturing is analyzed using a human plasma-derived antithrombin III medical preparation Neuart (manufactured by Mitsubishi Pharma Corporation) or the like as the standard substance and using Human Antithrombin III ELISA Kit (manufactured by Affinity Biologicals). By this analysis, it is possible to detect the recombinant human antithrombin in contained in culture supernatant and to measure its concentration. This recombinant antithrombin III having a hybrid type sugar chain which does not contain fucose as the N-linked type sugar chain, secreted into the yeast culture supernatant, can be purified by the method described in Example 4. In addition, the sugar chain structure of the purified antithrombin in protein can be analyzed by the method described in Example 4.

Thus, it has been described that a recombinant human antithrombin III mainly having a hybrid type sugar chain which does not contain fucose as the N-linked type sugar chain can be prepared by using, as the host, a *Pichia* yeast strain which mainly expresses a hybrid type sugar chain in which one N-acetylglucosamine residue is added to the non-reducing end of a Man8 type high mannose type sugar chain, as the N-linked type sugar chain, or a *Saccharomyces* yeast strain modified in the same manner. Next, methods for preparing yeast strains expressing a recombinant human antithrombin III mainly having a complex type double-strand sugar chain as the N-linked type sugar chain which does not contain fucose, using this yeast strain expressing a recombinant human antithrombin III mainly having a hybrid type sugar chain as the N-linked type sugar chain are described below.

12. Preparation of Yeast Strain into which a Recombinant Chimeric α-mannosidase II Gene is Introduced By carrying out PCR using a cDNA derived from a human tissue, for example, derived from the liver (manufactured by Clontech) as the template and using specific primers and KOD polymerase (manufactured by Toyobo Co., Ltd.), a cDNA encoding the active domain of α-mannosidase II (GenBank accession number: U31520) is specifically amplified. The thus amplified cDNA, after ligating a cDNA sequence encoding the leader peptide of a yeast mannosyltransferase (MNN 9) gene (GenBank accession number: L23752) to its 5'-terminal, is inserted into downstream of the promoter sequence of an expression vector for yeast, to thereby prepare a vector which expresses α-mannosidase II in the yeast Golgi body. Next, this vector is stably introduced into the yeast strain described in the above item 11 of this Example, which expresses a recombinant human antithrombin III mainly having a hybrid type sugar chain as the N-linked type sugar chain. A clone of the yeast after the gene introduction is selected based on its auxotrophy and drug resistance, and then expression of the chimeric α-mannosidase II is confirmed by RT-PCR.

13. Preparation of Yeast Strain into which Recombinant Chimeric N-acetylglucosaminyltransferase-II Gene is Introduced By carrying out PCR using a cDNA derived from a human tissue, for example, derived from the liver (manufactured by Clontech) as the template and using specific primers and KOD polymerase (manufactured by Toyobo Co., Ltd.), a cDNA encoding the active domain of N-acetylglucosaminyltransferase-II (GenBank accession number: U15128) is specifically amplified. The thus amplified cDNA, after ligating a cDNA sequence encoding the leader peptide of a yeast mannosyltransferase (MNN 9) gene (GenBank accession number: L23752) to its 5'-terminal, is inserted into downstream of the promoter sequence of an expression vector for yeast, to thereby prepare a vector which expresses N-acetylglucosaminyltransferase-II in the yeast Golgi body. Next, this vector is stably introduced into the yeast strain described in the above item in which a chimeric α-mannosidase II have been stably introduced into a yeast strain expressing a recombinant human antithrombin III mainly having a hybrid type sugar chain as the N-linked type sugar chain. A clone of the yeast after the gene introduction is selected based on its auxotrophy and drug resistance, and then expression of the chimeric N-acetylglucosaminyltransferase-II is confirmed by RT-PCR. By the above method, the principal structure of N-linked type sugar chain possessed by the gene recombinant antithrombin III expressed by the yeast strain into which the chimeric N-acetylglucosaminyltransferase-II is stably introduced can be modified into a complex type double-strand sugar chain which does not contain fucose, having two N-acetylglucosamine residues in the core region of the reducing end and having a structure in which three mannose residues are bound to its non-reducing end through a bi-branched structure, and one N-acetylglucosamine residue is added to each of the two non-reducing termini.

14. Preparation of Yeast Strain into which a Recombinant UDP-galactose Transporter Gene is Introduced By carrying out PCR using a cDNA derived from a human tissue, for example, derived from the liver (manufactured by Clontech) as the template and using specific primers and KOD polymerase (manufactured by Toyobo Co., Ltd.), a cDNA encoding the full translation region of UDP-galactose transporter (GenBank accession number: AB042425) is specifically amplified. The thus amplified cDNA is inserted into downstream of the promoter sequence of an expression vector for yeast, to thereby prepare a vector which expresses UDP-galactose transporter in the yeast Golgi body. Next, this vector is stably introduced into the yeast strain described in the above, which expresses a recombinant human antithrombin III mainly having an immature complex type biantennary sugar chain. A clone of the yeast after the gene introduction is selected based on its auxotrophy and drug resistance, and then expression of the UDP-galactose transporter is confirmed by RT-PCR.

15. Preparation of Yeast Strain into which Recombinant Chimeric α-1,4-galactosyltransferase Gene is Introduced By carrying out PCR using a cDNA derived from a human tissue, for example, derived from the liver (manufactured by Clontech) as the template and using specific primers and KOD polymerase (manufactured by Toyobo Co., Ltd.), a cDNA encoding β-1,4-galactosyltransferase (GenBank accession number: M22921) is specifically amplified. The thus amplified cDNA, after ligating a cDNA sequence encoding the leader peptide of a yeast mannosyltransferase (MNN 9) gene (GenBank accession number- L23752) to its 5'-terminal, is inserted into downstream of the promoter sequence of an expression vector for yeast, to thereby prepare a vector which expresses β-1,4-galactosyltransferase in the yeast Golgi body. Next, this vector is stably introduced into the yeast strain described in the above item in which a chimeric β-1,4-galactosyltransferase has been stably introduced into a yeast strain expressing a recombinant human antithrombin III mainly having an immature complex type biantennary sugar chain as the N-linked type sugar chain. A clone of the yeast after the gene introduction is selected based on its auxotrophy and drug resistance, and then expression of the chimeric β-1,4-galactosyltransferase is confirmed by RT-PCR. By the above method, the principal structure of N-linked type sugar chain possessed by the gene recombinant antithrombin III expressed by the yeast strain into which the chimeric β-1,4-galactosyltransferase is introduced can be modified into an immature complex type double-strand sugar chain having two N-acetylglucosamine residues in the core region of the reducing end and having a structure in which three mannose residues are bound to its non-reducing end through a bi-branched structure, and one N-acetylglucosamine residue is added to each of the two non-reducing termini.

16. Preparation of Yeast Strain into which a Recombinant CMP-Sialic Acid Transporter Gene is Introduced By carrying out PCR using a cDNA derived from a human tissue, for example, derived from the liver (manufactured by Clontech) as the template and using specific primers and KOD polymerase (manufactured by Toyobo Co., Ltd.), a cDNA encoding the full translation region of CMP-sialic acid transporter (GenBank accession number: D87969) is specifically amplified. The thus amplified cDNA is inserted into downstream of the promoter sequence of an expression vector for yeast, to thereby prepare a vector which expresses CMP-sialic acid transporter in the yeast Golgi body. Next, this vector is stably introduced into the yeast strain described in the above-described item, which expresses a recombinant human antithrombin III mainly having an immature biantennary sugar chain as the N-linked type sugar chain. A clone of the yeast after the gene introduction is selected based on its auxotrophy and drug resistance, and then expression of the CMP-sialic acid transporter is confirmed by RT-PCR.

17. Preparation of Yeast Strain into which Recombinant Chimeric Sialyltransferase Gene is Introduced By carrying out PCR using a cDNA derived from a human tissue, for example, derived from the liver (manufactured by Clontech) as the template and using specific primers and KOD polymerase (manufactured by Toyobo Co., Ltd.), a cDNA encoding the active domain of α2,3-sialyltransferase (GenBank accession number: L23768) or α2,6-sialyltransferase (GenBank accession number: X62822) is specifically amplified. The thus amplified cDNA, after ligating a cDNA sequence encoding the leader peptide of a yeast mannosyltransferase (MNN 9) gene (GenBank accession number: L23752) to its 5'-terminal, is inserted into downstream of the promoter sequence of an expression vector for yeast, to thereby prepare a vector which expresses sialyltransferase in the yeast Golgi body. Next, this vector is stably introduced into the yeast strain described in the above item in which a chimeric sialyltransferase has been stably introduced into a yeast strain expressing a recombinant human antithrombin III mainly having an immature complex type double-strand sugar chain as the N-linked type sugar chain. A clone of the yeast after the gene introduction is selected based on its auxotrophy and drug resistance, and then expression of the chimeric sialyltransferase is confirmed by RT-PCR. By the above method, the principal structure of N-linked type sugar chain possessed by the gene recombinant antithrombin III expressed by the yeast strain into which the chimeric sialyltransferase is stably integrated can be modified into a mature complex type biantennary sugar chain having two N-acetylglucosamine residues in the core region of the reducing end and having a structure in which three mannose residues are bound to its non-reducing end through a bi-branched structure, and one N-acetylglucosamine residue, one galactose residue and one sialic acid are respectively added to each of the two non-reducing termini.

18. Preparation of Recombinant Antithrombin III Protein Using Yeast

The yeast strain expressing a recombinant antithrombin III mainly having a complex type double-strand sugar chain in which no fucose residue is bound to the reducing end and sialic acid is added to the non-reducing end, prepared in the above item, is inoculated into liquid YPD medium (manufactured by Invitrogen) and subjected to batch culturing at 30° C. for 24 hours or more to secret the recombinant antithrombin m into the culture supernatant. The culture supernatant obtained after the culturing is analyzed by Human Antithrombin III ELISA Kit (manufactured by Affinity Biologicals) using a human plasma-derived antithrombin III Neuart (manufactured by Mitsubishi Pharma Corporation) or the like as the standard substance. By this analysis, it is able to detect recombinant antithrombin III contained in the culture supernatant and to measure its concentration. In addition, the recombinant antithrombin III mainly having a complex type biantennary sugar chain as the N-linked sugar chain which does not contain fucose, secreted into this yeast culture supernatant can be purified by the method described in Example 4. Also, the sugar chain structure of the purified antithrombin III protein can be analyzed by the method described in Example 4.

Thus, it is shown that a recombinant antithrombin III mainly having a complex type sugar chain as the N-glycoside-linked sugar chain which does not contain fucose can be prepared by preparing a yeast strain expressing a recombinant antithrombin III mainly having a complex type sugar chain as the N-glycoside-linked sugar chain which does not contain fucose, and culturing the yeast. In this connection, the antithrombin III expressed by the yeast in this Example is a protein having equivalent biological activities in comparison with those of the antithrombin III expressed by the FUT8 double knockout cell and the antithrombin III derived from human plasma.

While the invention has been described in detail and with reference to specific embodiments thereof, it will be apparent to one skill in the art that various changes and modifications can be made therein without departing from the spirit and scope thereof All references cited herein are incorporated in their entirety.

What is claimed is:

1. An isolated, recombinant antithrombin III in which an amino acid sequence of the recombinant antithrombin III consists of the amino acid sequence at positions from 33 to 464 of SEQ ID NO:4;
   wherein the recombinant antithrombin III comprises four complex type N-glycoside-linked carbohydrate chains each at asparagines residues at positions 128, 167, 187 and 224 in the amino acid sequence of SEQ ID NO:4, wherein each of said carbohydrate chains lacks fucose bound to N-acetylglucosamine in the reducing end of said carbohydrate chains,
   wherein the recombinant antithrombin III is expressed in a CHO cell into which a DNA encoding the amino acid sequence at positions from 33 to 464 of SEQ ID NO:4 is introduced, wherein the genome of the CHO cell is modified so as to have deleted activity of an enzyme relating to synthesis of an intracellular carbohydrate nucleotide, GDP-fucose, or an enzyme relating to the modification of a carbohydrate chain in which 1-position of fucose is bound to 6-position of N-acetylglucosamine in the reducing end through α-bond in a complex type N-glycoside-linked carbohydrate chain.

2. A medicament which comprises the antithrombin III according to claim 1 as an active ingredient and a pharmaceutically acceptable carrier.

3. The medicament according to claim 2 which has an activity of inhibiting blood coagulation.

* * * * *